(12) United States Patent
Nikolau et al.

(10) Patent No.: US 8,951,762 B2
(45) Date of Patent: Feb. 10, 2015

(54) MATERIALS AND METHODS FOR USING AN ACYL—ACYL CARRIER PROTEIN THIOESTERASE AND MUTANTS AND CHIMERAS THEREOF IN FATTY ACID SYNTHESIS

(75) Inventors: Basil J. Nikolau, Ames, IA (US); Marna Yandeau-Nelson, Ames, IA (US); Fuyuan Jing, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 13/558,323

(22) Filed: Jul. 25, 2012

(65) Prior Publication Data

US 2013/0029387 A1 Jan. 31, 2013

Related U.S. Application Data

(60) Provisional application No. 61/512,373, filed on Jul. 27, 2011.

(51) Int. Cl.
| | | |
|---|---|---|
| C12P 7/64 | (2006.01) |
| C12N 9/16 | (2006.01) |
| C12N 1/20 | (2006.01) |
| C12N 1/00 | (2006.01) |
| C12N 1/12 | (2006.01) |
| C07H 21/04 | (2006.01) |

(52) U.S. Cl.
CPC ........... *C12N 9/16* (2013.01); *C12Y 301/02014* (2013.01); *C12P 7/6409* (2013.01); *C07K 2319/00* (2013.01)
USPC ..... 435/134; 435/196; 435/252.3; 435/254.2; 435/257.2; 536/23.2

(58) Field of Classification Search
None
See application file for complete search history.

(56) References Cited

U.S. PATENT DOCUMENTS

| | | |
|---|---|---|
| 5,147,792 A | 9/1992 | Perchorowicz et al. |
| 5,910,631 A | 6/1999 | Topfer et al. |
| 5,955,329 A | 9/1999 | Yuan et al. |
| 6,150,512 A | 11/2000 | Yuan |
| 7,504,563 B1 | 3/2009 | Kridl |
| 7,855,321 B2 | 12/2010 | Renz et al. |
| 7,935,515 B2 | 5/2011 | Franklin et al. |
| 2008/0148434 A1 | 6/2008 | Dehesh et al. |
| 2009/0061493 A1 | 3/2009 | Trimbur et al. |
| 2009/0214744 A1 | 8/2009 | Kridl |
| 2009/0298143 A1 | 12/2009 | Roessler et al. |
| 2010/0154293 A1 | 6/2010 | Hom et al. |
| 2011/0020883 A1 | 1/2011 | Roessler et al. |
| 2011/0072714 A1 | 3/2011 | Gaertner |
| 2011/0146142 A1 | 6/2011 | Lee et al. |
| 2011/0162259 A1 | 7/2011 | Gaertner |
| 2011/0250659 A1 | 10/2011 | Roberts et al. |
| 2011/0294174 A1 | 12/2011 | Franklin et al. |
| 2012/0115195 A1 | 5/2012 | Keasling et al. |
| 2012/0164700 A1 | 6/2012 | Watts et al. |

OTHER PUBLICATIONS

Steen et al. Microbial production of fatty-acid-derived fuels and chemicals from plant biomass, Nature (Jan. 2010), 463: 559-562.*
UniProt Accession No. C6LDQ9, created Sep. 22, 2009.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Dehesh et al., Two Novel Thioesterases Are Key Determinants of the Bimodal Distribution of Acyl Chain Length of *Cuphea palustris* Seed Oil, *Plant Physiol.*, 110:203-210 (1996).
Families—TE, "ThYme: Thioester-active Enzymes," NSF Engineering Res. Cent. Biorenewable Chem., (1995) retrieved online at: http://www.enzyme.cbirc.iastate.edu/?a=viewfamilies&class=TE on Jun. 20, 2011.
Liu et al., "Fatty acid production in genetically modified cyanobacteria," *PNAS*, retrieved online at: www.pnas.org/cgi/doi/10.1073/pnas.1103014108 (2011).
Mayer et al., "Identification of amino acid residues involved in substrate specificity of plant acyl-ACP thioesterases using a bioinformatics-guided approach," *BMC Plant Biology*, 7(1): 1-11 (2007).
BLAST Sequence 40 from pre-grant Patent Publication No. US20110020883.
BLAST Sequence 45 from pre-grant Patent Publication No. US20110020883.
BLAST Sequence 43 from pre-grant Patent Publication No. US20110020883.
BLAST Sequence 61 from pre-grant Patent Publication No. US20100151539.
BLAST Sequence 138 from pre-grant Patent Publication No. US20100151539.
BLAST Sequence 57790 from pre-grant Patent Publication No. US20070283460.
BLAST Sequence 57790 from pre-grant Patent Publication No. US20040034888.
BLAST Sequence 182057 from pre-grant Patent Publication No. US20040031072.

(Continued)

*Primary Examiner* — Iqbal H Chowdhury
(74) *Attorney, Agent, or Firm* — Carol Larcher; Larcher & Chao Law Group

(57) ABSTRACT

A method of increasing production of fatty acids comprising introducing into a host cell or organism and expressing therein an acyl-acyl carrier protein (ACP) thioesterase (TE) from *Bryantella formatexigens* or a mutant thereof; a method of making a mutant *B. formatexigens* acyl-ACP TE; a method of making a chimeric *Cuphea viscosissima* acyl-ACP TE; a nucleic acid encoding a mutant acyl-ACP TE or a chimeric *C. viscosissima* acyl-ACP TE; a host cell or organism comprising the nucleic acid; a mutant acyl-ACP TE or chimeric *C. viscosissima* acyl-ACP TE; a method of altering the specificity of a plant acyl-ACP TE; and a method of altering the level of activity of a plant acyl-ACP TE.

3 Claims, 11 Drawing Sheets

(56) References Cited

OTHER PUBLICATIONS

BLAST Sequence 62889 from pre-grant Patent Publication No. US20070061916.
BLAST Sequence 182054 from pre-grant Patent Publication No. US20040031072.
BLAST Sequence 55416 from pre-grant Patent Publication No. US20070283460.
BLAST Sequence 55416 from pre-grant Patent Publication No. US20040034888.
BLAST Sequence 43584 from pre-grant Patent Publication No. US20070283460.
BLAST Sequence 43584 from pre-grant Patent Publication No. US20040034888.
BLAST Sequence 127 from pre-grant Patent Publication No. US20090293154.
BLAST Sequence 46539 from pre-grant Patent Publication No. US20060123505.
BLAST Sequence 164709 from pre-grant Patent Publication No. US20110131679.
BLAST Sequence 50930 from pre-grant Patent Publication No. US20060123505.
BLAST Sequence 164709 from pre-grant Patent Publication No. US20040123343.
BLAST Sequence 191821 from pre-grant Patent Publication No. US20110131679.
BLAST Sequence 191821 from pre-grant Patent Publication No. US20040123343.
BLAST Sequence 366754 from pre-grant Patent Publication No. US20090087878.
BLAST Sequence 366754 from pre-grant Patent Publication No. US20040214272.
BLAST Sequence 188364 from pre-grant Patent Publication No. US20110131679.
BLAST Sequence 188364 from pre-grant Patent Publication No. US20040123343.
BLAST Sequence 191819 from pre-grant Patent Publication No. US20110131679.
BLAST Sequence 191819 from pre-grant Patent Publication No. US20040123343.
BLAST Sequence 52665 from pre-grant Patent Publication No. US20070283460.
BLAST Sequence 52665 from pre-grant Patent Publication No. US20040034888.
BLAST Sequence 339361 from pre-grant Patent Publication No. US20090087878.
BLAST Sequence 339361 from pre-grant Patent Publication No. US20040214272.
BLAST Sequence 52516 from pre-grant Patent Publication No. US20070283460.
BLAST Sequence 52516 from pre-grant Patent Publication No. US20040034888.
BLAST Sequence 51871 from pre-grant Patent Publication No. US20070283460.
BLAST Sequence 51871 from pre-grant Patent Publication No. US20040034888.
BLAST Sequence 68212 from pre-grant Patent Publication No. US20070283460.
BLAST Sequence 68212 from pre-grant Patent Publication No. US20040034888.
BLAST Sequence 63 from pre-grant Patent Publication No. US20100151539.
BLAST Sequence 139 from pre-grant Patent Publication No. US20100151539.
BLAST Sequence 59 from pre-grant Patent Publication No. US20100151539.
BLAST Sequence 140 from pre-grant Patent Publication No. US20100151539.
BLAST Sequence 69747 from pre-grant Patent Publication No. US20070283460.
BLAST Sequence 69747 from pre-grant Patent Publication No. US20040034888.
BLAST Sequence 41073 from pre-grant Patent Publication No. US20070283460.
BLAST Sequence 41073 from pre-grant Patent Publication No. US20040034888.
BLAST Sequence 55067 from pre-grant Patent Publication No. US20060123505.
BLAST Sequence 50206 from pre-grant Patent Publication No. US20070283460.
BLAST Sequence 50206 from pre-grant Patent Publication No. US20040034888.
BLAST Sequence 184933 from pre-grant Patent Publication No. US20070044171.
BLAST Sequence 125 from pre-grant Patent Publication No. US20090293154.

* cited by examiner

```
CvFatB3    1  MVAAAASS-AFFSPETPGTSPKPGKFGNWPSS-------LSLPFNPKSNHNGGKQVKANA
CvFatB1    1  MVAAAATS-AFFPVDAPGTSPKPGKSGNWPSS-------LSPTFKPKSIPNGGFQVKANA
CvFatB2    1  ---SAASS-AFFPVESADTSSRPGKLGNGPSS-------FSP-LKPKSIPNGGKQVKASA
CnFatB2    1  MVASIAAS-AFFPTPSGSSSGAASAKASKTIGEGPGSLDVRGIVAKPTS-SSAKMQFKVKV
CnFatB1    1  MVASVAAS-AFFPTP-SFSSTASAKASKTIGEGSESLDVRGIVAKPTS-SSAAMQGKVKA
CnFatB3    1  MVASVAASSSFFPVD-SSSSSASAKASRGIPDG---LDVRGIVAKPAS-SSQWMQAKASA

CvFatB3   53  SAHPKANGSAVSLKAGSLEGQEDTSSPSPPRTFISQLPDWSMLYSAITTVFVAAEKQWT
CvFatB1   53  SAHPKANGSAVMLKEGSLMGQEDTSS-SPPPRAFLNQLPDWSMLLAITTVFVAAEKQWT
CvFatB2   49  SAPPKINGSSVGLKSGGLKTHEDAPS-APPPRTFINQLPDWSMLLAAITTAFLAAEKQWM
CnFatB2   59  QPVPKINGAKVGLKVETQLADLESSP-SSAPRTFYNQLPDWSVLLAAVTTIFLAAEKQWT
CnFatB1   58  QAVPKINGTKVGLKTESQLAEEDAAP-SSAPRTFYNQLPDWSLLLAAVTTIFLAAEKQWT
CnFatB3   56  RATPKIDDTKVGLRTD----VSEDAA-STARRTSYNQLPDWSMLLAAIRTIFSAAEKQWT

CvFatB3  113  MLDRKSKRPDVLVKPE-----VQDGVSFRQSFSIRSYEIGVDRTASIETLMNLFQETSLN
CvFatB1  112  MLDRKSKRPDMLVDSVGLKSIVRDGLVSRHSFSIRSYEIGADRTASIETLMNHLQETTTN
CvFatB2  108  MLDRKPKRLDMLEDPFGLGKIVQDGLVFRQNFSIRSYEIGADRTASIETVMNHLQETALN
CnFatB2  118  ILLWKPKRPDMLADAFGLGKIVQDGLVFKQNFSIRSYEIGADRTASIETLMNHLQETALN
CnFatB1  117  LLLWKEKRPDMLTDAFSLGKIVQDGLSFRQNFSIRSYEIGADRTASIETLMNHLQETALN
CnFatB3  111  LLLSKKKGALAVADASGVGKIVKNQLVSRQNFSIRSYEIGVDKFASVEALMNEFQETSLN

CvFatB3  168  HCKSLGLKNDGFGRTPEMCKRDLIWVVTKMQIEVNRYPTWGDTIEVTTWVSESGKNGMSR
CvFatB1  172  HCKSLGLHNDGFGRTPGMCKNDLIWVITKMQIMVNRYPTWGDTVEKNTWFSQSGKIGMAS
CvFatB2  168  HVKSAGLSNDGFGRTPEMYKRDLIWVVAKMQVVVNRYPTWGDTVEVNTWVAKSGKNGMRR
CnFatB2  178  HVKSAGIMGDGFGATPEMSKRNLIWVVTKMQVVIERYPSWGDVVEVDTWVGPIGKNGMRR
CnFatB1  177  HVRNAGLLGDGFGATPEMSKRNLIWVVTKMQVSVERYPSWGDVDTWVGASGKNGMRR
CnFatB3  171  HCKCIGLMHGGFGCTPEMTRRNLIWVVAKMLVHVERYPSWGDVVQINTWISSSGKNGMGR

CvFatB3  228  DWLISDCHSGEILIRATSVWAMMNQKTRSLSKLPDEVRQEIVPYFVDSAPVISD-DRKLH
CvFatB1  232  DWLISDCMTGEILLRATSVWAMMNQKTRSFSKLPTEVRQELTPHFVDSPHVIEDNDQKIR
CvFatB2  228  DWLISDCNTGEIETRASSVWMMMNQKTRKLSKKPDEVREIEPHFVDSAPVIEDDDRKLP
CnFatB2  238  DWHYRDHRSGQTIIRATSVWVMMNKNTRKLSKVPEEVRAEIGPYFVERAAIVDEDSRKLP
CnFatB1  237  DWHYRDYRTGQTIIRATSVWVMMNKETRKLSKMPEEVRAEIGPYFVEBAAIVDEDSRKLP
CnFatB3  231  DWHYEDCGTGLPISKGTSVWVKMDKETRKLSKLPEEVRAEITPFFSERDAVLDDNGRKLP

CvFatB3  287  KLDVKTGDSIRNGLTPRWNDFDVNQKRYIIQWLLKSVPTEVFETQELCGLTLEYRRE
CvFatB1  292  KFDVKTGDSIRKGLTPRWNDLDVNQKVSNVKYIGWILESSPIEVLETQKLCSLTYEYRRE
CvFatB2  288  KLDEKSADSIRKGLTPRWNDLDVNQKVNNAKYIGWILESTPPEVLETQKLCSLTLEYRRE
CnFatB2  298  KLEEDTTLYIRKGLTPRWGDLDVNQHVNNVKYIGWILESAPISNLSNHELASMSLEYRRE
CnFatB1  297  KLDDTALYIKKGLTPRWSDLDVNQHVNNVKYIGWILESAPISLSNHELASMTLEYRRE
CnFatB3  291  KFDDDSAAHVRKGLTPRWHDFDVNQHVNNVKYVGWILESVPVWMEDGYEVATMSLEYRRE

CvFatB3  347  CRRDSVIESVTANDDSKEG----DRSLYQHLLRLENGAEHALGRTEWRPKNAGATGAVST
CvFatB1  352  CGMDSVLESVTAVDPSENG----GRSQYKHLLRLKDGTEIVKSRTEWRPKNAGTNCAIST
CvFatB2  348  CGREDSVLESLTAVDPSGEG----YGSQFQHLLRLEDGGKIVKGRTEWRPKNACINGVVPS
CnFatB2  358  CGRDSVLQSLTAVSNDLTDCLVESGIECQHLLQLECGTESVKGRTEWRPKH--SPALGNM
CnFatB1  357  CGRDSVLQSLTAISNDCTGGLPEASIECQHLLQLEGGAEIVKGRTQWRPKR--NS----
CnFatB3  351  CRMDSVLQSLTAVSSDHADC---SPIVCQHLLRLEDGTEIVKCQTEWRPKQQ-QRDLGNM

CvFatB3  403  G--KTENCNSVS  (SEQ ID NO: 1)
CvFatB1  408  STAKTGNCNSVS (SEQ ID NO: 2)
CvFatB2  404  E--ESSPGDYS- (SEQ ID NO: 3)
CnFatB2  416  G--PTPGGSA-- (SEQ ID NO: 4)
CnFatB1  410  G--PTSAGSA-- (SEQ ID NO: 5)
CnFatB3  407  G--LHPTESK-- (SEQ ID NO: 6)
```

FIG. 1

| Sample name | total | 4:0 | 6:0 | 8:0 | 10:0 | 10:1 | 12:0 | 12:1 | 14:0 | 14:1 | 16:0 | 16:1 |
|---|---|---|---|---|---|---|---|---|---|---|---|---|
| CvB1 | 543 | 0.03 | 3.47 | 45.21 | 26.09 | 8.90 | 4.10 | 9.65 | 0.81 | 1.00 | 0.37 | 0.37 |
| rTE4 | 493 | 0.06 | 1.08 | 24.24 | 35.86 | 11.87 | 4.28 | 12.15 | 3.31 | 3.89 | 0.50 | 2.76 |
| rTE8 | 88 | 0.34 | 4.67 | 17.79 | 10.18 | 2.00 | 4.70 | 5.44 | 29.73 | 7.04 | 1.58 | 16.53 |
| rTE16 | 823 | 0.41 | 1.33 | 38.75 | 15.23 | 6.56 | 9.36 | 16.18 | 2.56 | 7.51 | 0.44 | 1.67 |
| rTE20 | 387 | 0.21 | 0.66 | 16.10 | 19.96 | 8.14 | 12.72 | 24.34 | 2.42 | 13.40 | 0.09 | 1.96 |
| rTE24 | 279 | 1.15 | 1.08 | 19.58 | 4.10 | 1.30 | 6.58 | 7.31 | 27.02 | 6.30 | 2.31 | 23.28 |
| rTE28 | 283 | 0.25 | 0.32 | 4.77 | 1.06 | 0.18 | 1.65 | 1.72 | 40.46 | 1.99 | 3.60 | 44.00 |
| rTE32 | 490 | 0.11 | 1.24 | 25.50 | 24.54 | 8.13 | 11.18 | 16.09 | 4.53 | 4.33 | 0.32 | 4.03 |
| rTE36 | 193 | 0.47 | 0.82 | 6.88 | 18.46 | 4.23 | 13.63 | 17.69 | 10.88 | 17.71 | 0.59 | 8.64 |
| rTE40 | 138 | 0.62 | 5.51 | 16.50 | 3.16 | 0.31 | 6.75 | 4.82 | 30.51 | 10.92 | 1.81 | 19.10 |
| rTE44 | 46 | 1.40 | 3.78 | 6.94 | 1.87 | 0.00 | 3.71 | 1.53 | 43.81 | 7.10 | 0.43 | 29.42 |
| rTE52 | 874 | 7.23 | 17.35 | 31.04 | 11.36 | 8.10 | 5.45 | 12.34 | 1.42 | 4.70 | 0.10 | 0.90 |
| rTE56 | 408 | 2.77 | 2.12 | 24.70 | 5.59 | 2.37 | 7.69 | 8.22 | 25.68 | 4.74 | 1.68 | 14.45 |
| rTE60 | 75 | 0.19 | 0.22 | 3.96 | 1.77 | 0.40 | 1.82 | 2.57 | 54.10 | 1.29 | 4.99 | 28.68 |

FIG. 8B

| Position | 110 | 133 | 139 | 173 | 176 | 184 | 192 | 198 | 205 |
|---:|:---:|:---:|:---:|:---:|:---:|:---:|:---:|:---:|:---:|
| AAC49784.1\|Cuphea.wrightii | L | F | I | F | L | I | P | N | F |
| AAC49269.1\|Cuphea.hookeriana | V | F | I | L | L | I | P | S | F |
| AAC49179.1\|Cuphea.palustris | V | L | I | F | L | F | P | N | F |
| CAB60830.1\|Cuphea.lanceolata | L | F | I | F | L | L | P | N | F |
| AEM72522.1\|Cuphea.viscosissima | L | F | I | F | L | L | P | N | F |
| XP_002453522.1\|Sorghum.bicolor | V | V | N | L | I | I | T | D | L |
| NP_001151366.1\|Zea.mays | V | V | N | L | I | I | S | D | L |
| XP_002437226.1\|Sorghum.bicolor | V | V | N | L | I | I | S | D | L |
| NP_001147887.1\|Zea.mays | V | V | N | L | I | I | S | D | L |
| AAG43861.1\|Iris.tectorum | V | A | N | L | F | I | V | D | L |
| AAG43860.1\|Iris.tectorum | V | A | N | L | F | I | A | D | L |
| AAG43858.1\|Iris.germanica | V | A | N | L | F | I | A | D | L |
| AAG43857.1\|Iris.germanica | V | A | N | L | F | I | V | D | L |
| AEM72520.1\|Cocos.nucifera | V | V | N | L | V | I | A | D | L |
| AAL15645.1\|Elaeis.guineensis | V | V | N | L | V | L | A | D | L |
| ABD83939.1\|Elaeis.guineensis | V | V | N | L | V | I | A | D | L |
| AAM09524.1\|Elaeis.oleifera | V | V | N | L | M | I | A | D | L |
| AEM72519.1\|Cocos.nucifera | V | V | N | L | M | I | A | D | L |
| AAD42220.2\|Elaeis.guineensis | V | V | N | L | M | I | A | D | L |
| AAN17328.1\|Elaeis.oleifera | V | V | N | L | M | I | A | D | L |
| CAA54060.1\|Cuphea.lanceolata | V | V | N | L | I | I | A | D | L |
| CAC19933.1\|Cuphea.lanceolata | V | V | N | L | I | I | A | D | L |
| AAC72882.1\|Cuphea.hookeriana | V | V | N | L | I | I | P | D | L |
| ABB71581.1\|Cuphea.calophylla | V | V | N | L | I | I | A | D | L |
| AEM72523.1\|Cuphea.viscosissima | V | V | N | L | I | I | A | D | L |
| Q39513.1\|Cuphea.hookeriana | V | V | N | L | I | I | P | D | L |
| Q9SQI3.1\|Gossypium.hirsutum | V | V | N | L | I | I | D | D | L |
| AAD01982.1\|Gossypium.hirsutum | V | V | N | L | I | I | D | D | L |
| ABH11710.1\|Brassica.napus | V | V | N | L | I | I | D | D | L |
| XP_002892461.1\|Arabidopsis.lyrata | V | V | N | L | I | I | D | D | L |
| NP_172327.1\|Arabidopsis.thaliana | V | V | N | L | I | I | D | D | I |
| CAA85387.1\|Arabidopsis.thaliana | V | V | N | L | I | I | D | D | I |
| CAA85388.1\|Arabidopsis.thaliana | V | V | N | L | I | I | D | D | I |

FIG. 9

MATERIALS AND METHODS FOR USING AN ACYL—ACYL CARRIER PROTEIN THIOESTERASE AND MUTANTS AND CHIMERAS THEREOF IN FATTY ACID SYNTHESIS

CROSS-REFERENCE TO RELATED APPLICATION

This application claims priority to U.S. provisional patent application No. 61/512,373, which was filed on Jul. 27, 2011, and is hereby incorporated by reference in its entirety.

STATEMENT REGARDING FEDERALLY SPONSORED RESEARCH OR DEVELOPMENT

The work described herein was supported, at least in part, by The National Science Foundation under contract no. EEC0813570. Therefore, the Government of the United States of America has certain rights in the invention.

TECHNICAL FIELD

The present disclosure relates to enzymes, mutants and chimeras thereof, fatty acid synthesis, nucleic acids, proteins and host cells and organisms.

BACKGROUND

De novo fatty acid biosynthesis can be considered an iterative "polymerization" process, commonly primed with the acetyl moiety from acetyl-CoA and with iterative chain extension occurring by reaction with malonyl-acyl carrier protein (ACP). In most organisms this process optimally produces 16- and 18-carbon (C16 and C18) fatty acids. The enzyme that determines fatty acid chain length is acyl-ACP thioesterase (TE). This enzyme catalyzes the terminal reaction of fatty acid biosynthesis, acyl-ACP thioester bond hydrolysis (i.e., the hydrolysis of the thioester bond between the acyl chain and the sulfhydryl group of the phosphopantetheine prosthetic group of ACP), to release a free fatty acid and ACP. This reaction terminates acyl-chain elongation of fatty acid biosynthesis and, therefore, determines fatty acid chain length. It is also the biochemical determinant of the fatty acid composition of storage lipids in plant seeds.

In discrete phyla and/or tissues of specific organisms (primarily higher plant seeds), thioester hydrolysis optimally produces medium-chain (C8-C14) fatty acids (MCFAs), which have wide industrial applications (e.g., producing detergents, lubricants, cosmetics, and pharmaceuticals) (Dehesh et al., Plant Physiol. 110: 203-210 (1996)). TEs that specifically hydrolyze medium-chain acyl-ACP substrates have been studied widely (Dehesh et al. (1996), supra; Voelker et al., Science 257: 72-74 (1992)); and Yuan et al., PNAS USA 92: 10639-10643 (1995)). Short-chain fatty acids (SCFAs; e.g., butanoic acid and hexanoic acid) have more recently gained importance as potential bio-renewable chemicals that could be derived from the fatty acid biosynthesis pathway (Nikolau et al., Plant J. 54: 536-545 (2008)). As a critical acyl chain termination enzyme, acyl-ACP TEs with desired substrate specificities are, therefore, important for engineering this pathway.

To date, dozens of acyl-ACP TEs have been functionally characterized and sorted into two classes, FatA and FatB (Jones et al., Plant Cell 7: 359-371 (1995)). FatA-class TEs act on long-chain acyl-ACPs, preferentially on oleoyl-ACP (Jones et al. (1995), supra; Hawkins et al., Plant J. 13: 743-752 (1998); Serrano-Vega et al., Planta 221: 868-880 (2005); and Sanchez-Garcia et al., Phytochemistry 71: 860-869 (2010)), while FatB-class TEs preferably hydrolyze acyl-ACPs with saturated fatty acyl chains (Jones et al. (1995), supra). The archetypical FatB-class TE was isolated from the developing seeds of California bay (*Umbellularia californica*). This enzyme is specific for 12:0-ACP, and it plays a critical role in MCFA production (Voelker et al. (1992), supra; and Pollard et al., Arch Biochem. Biophys. 284: 306-312 (1991)). This discovery spurred isolation of additional MCFA-specific TEs from *Cuphea* (Dehesh et al. (1996), supra; Dehesh et al. Plant J. 9: 167-172 (1996); and Leonard et al., Plant Mol. Biol. 34: 669-679 (1997)), *Arabidopsis thaliana* (Dormann et al., Arch Biochem. Biophys. 316: 612-618 (1995)), *Myristica fragrans* (nutmeg) (Voelker et al., Plant Physiol. 114: 669-677 (1997)), and *Ulmus americana* (elm) (Voelker et al. (1997), supra).

Recently, TEs obtained from public databases were classified into 23 families based on sequence and three-dimensional structure similarity (Cantu et al., Protein Sci. 19: 1281-1295 (2010)). These TEs were defined as enzymes that can hydrolyze any thioester bond irrespective of the chemical nature of the carboxylic acid and thiol molecules that constitute the substrates of these enzymes. The TE sequences are collected in the constantly updated ThYme database (www.enzyme.cbirc.iastate.edu; Cantu et al., Nucleic Acids Res. 39: D342-346 (2011), which is hereby incorporated by reference). Of these 23 families, Family TE14 contains plant and bacterial acyl-ACP TEs involved in Type II fatty acid synthesis, the reactions of which are catalyzed by discrete monofunctional enzymes. Family TE14 contained 360 unique sequences as of late 2010, but only ~7% of these sequences had been functionally characterized, and all of those were FatA and FatB TEs from higher plants. The remaining ~220 bacterial acyl-ACP TEs were mostly generated from genomic sequencing projects and had not been functionally characterized.

Alteration of the substrate specificity of plant TEs has been described by Yuan et al. (U.S. Pat. Nos. 5,955,329 and 6,150,512, which are incorporated herein by reference for their teachings regarding same) and Roessler et al. (U.S. Pat. App. Pub. No. 2011/0020883, which is hereby incorporated by reference for its teachings regarding same). Yuan et al. identifies the C-terminal two-thirds portion of plant TEs as desirable for modification. Roessler et al. discloses a plant acyl-ACP thioesterase of a specified sequence (sequence identification no. 29) in which amino acid 174, alone or in further combination with amino acid 103, is mutated.

In view of the foregoing, the present disclosure seeks to provide methods of using acyl-ACP TE and mutants and chimeras thereof, in particular bacterial and plant acyl-ACP TE and mutants and chimeras thereof, to alter substrate specificity and/or alter activity (e.g., increase production of fatty acids) in a host cell or organism. These and other objects and advantages, as well as additional inventive features, will become apparent from the detailed description provided herein.

SUMMARY

A method of increasing production of fatty acids, such as short-chain fatty acids and/or fatty acids having from about six carbons to about 12 carbons, such as from about 10 carbons to about 12 carbons (e.g., fatty acids having less than about 10 carbons or fatty acids having less than about 12 carbons) in a host cell or organism is provided. The method comprises introducing into the host cell or organism and expressing therein a nucleic acid molecule comprising a nucleotide sequence encoding an acyl-acyl carrier protein (ACP) thioesterase (TE) from *Bryantella formatexigens*.

Another method of increasing production of fatty acids, such as short-chain fatty acids and/or fatty acids having from about six carbons to about 12 carbons, such as from about 10 carbons to about 12 carbons (e.g., fatty acids having less than about 10 carbons or fatty acids having less than about 12 carbons) in a host cell or organism is also provided. The method comprises introducing into the host cell or organism and expressing therein a nucleic acid molecule comprising a nucleotide sequence encoding a mutant acyl-ACP TE derived from wild-type *Bryantella formatexigens* acyl-ACP TE, wherein the mutant acyl-ACP TE produces more fatty acids, such as short-chain fatty acids, in the host cell or organism that the corresponding wild-type acyl-ACP TE.

Also provided is a method of making a mutant *Bryantella formatexigens* acyl-ACP TE. The method comprises making a mutant *Bryantella formatexigens* acyl-ACP TE comprising two or more amino acid mutations comprising N169Y and S222I.

An isolated or purified nucleic acid molecule is also provided. The nucleic acid molecule comprises a nucleotide sequence encoding a mutant acyl-ACP TE, which is derived from wild-type *Bryantella formatexigens* acyl-ACP TE, comprises two or more amino acid mutations comprising N169Y and S222I, and has increased thioesterase activity compared to wild-type *Bryantella formatexigens* acyl-ACP TE. The isolated or purified nucleic acid molecule can be a vector.

Also provided is a host cell or organism. The host cell or organism comprises the above-described nucleic acid molecule comprising a nucleotide sequence encoding a mutant acyl-ACP TE.

Further provided is an isolated or purified mutant acyl-ACP TE. The mutant acyl-ACP TE is derived from wild-type *Bryantella formatexigens* acyl-ACP TE, comprises two or more amino acid mutations comprising N169Y and S222I, and has increased thioesterase activity compared to wild-type *Bryantella formatexigens* acyl-ACP TE.

A method of making a chimeric *Cuphea viscosissima* acyl-ACP TE gene is also provided. The method comprises replacing a segment of a wild-type *Cuphea viscosissima* acyl-ACP TE with a segment of another acyl-ACP TE.

Further provided is another isolated or purified nucleic acid molecule. The nucleic acid molecule comprises a nucleotide sequence encoding a chimeric *Cuphea viscosissima* acyl-ACP TE gene, which comprises a segment of another acyl-ACP TE gene. The isolated or purified nucleic acid molecule can be a vector.

Still further provided is another host cell or organism. The host cell or organism comprises the above-described isolated or purified nucleic acid molecule comprising a nucleotide sequence encoding a chimeric *Cuphea viscosissima* acyl-ACP TE gene.

Even still further provided is an isolated or purified chimeric *Cuphea viscosissima* acyl-ACP TE. The chimera comprises a segment of another acyl-ACP TE.

A method of altering the specificity of a plant acyl-ACP TE for at least one of its substrates is also provided. The method comprises introducing into the plant acyl-ACP TE a substrate specificity-altering mutation in the region corresponding to amino acids 118-167 of the mature amino acid sequence of the *Cuphea viscosissima* acyl-ACP TE encoded by FatB2. The method can comprise mutating at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The method can further comprise mutating at least one amino acid corresponding to an amino acid selected from the group consisting of amino acid 110 and amino acid 184 of the mature amino acid sequence of the *Cuphea viscosissima* acyl-ACP TE encoded by FatB2. The method can further comprise altering the level of activity of the plant acyl-ACP TE by a method comprising mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

In view of the foregoing, a method of altering the level of activity of a plant acyl-ACP TE is also provided. The method comprises mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2. The method can further comprise altering the specificity of the plant acyl-ACP TE by a method comprising introducing into the plant acyl-ACP TE a substrate specificity-altering mutation in the region corresponding to amino acids 118-167 of the mature amino acid of the *Cuphea viscosissima* acyl-ACP TE encoded by FatB2. The method can comprise mutating at least one amino acid corresponding to an amino selected from the group consisting of amino acid 133, amino acid 142, and amino acid 143 of the mature amino acid sequence of the *Cuphea viscosissima* acyl-ACP TE encoded by FatB2. The method can further comprise mutating at least one amino acid corresponding to an amino acid selected from the group consisting of amino acid 110 and amino acid 184 of the mature amino acid sequence of the *Cuphea viscosissima* acyl-ACP TE encoded by FatB2.

Yet another isolated or purified nucleic acid molecule is provided. The isolated or purified nucleic acid molecule comprises a nucleotide sequence encoding a mutant plant acyl-ACP TE, which comprises a substrate specificity-altering mutation in the region corresponding to amino acids 118-167 of the mature amino acid sequence of the *Cuphea viscosissima* acyl-ACP TE encoded by FatB2. The isolated or purified nucleic acid molecule can be a vector. The encoded mutant plant acyl-ACP TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The encoded mutant plant acyl-ACP TE can further comprise a mutation of at least one amino acid corresponding to an amino acid selected from the group consisting of amino acid 110 and amino acid 184 of the mature amino acid sequence of the *Cuphea viscosissima* acyl-ACP TE encoded by FatB2. The encoded mutant plant acyl-ACP TE can further comprise a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

Still yet another isolated or purified nucleic acid molecule is provided. The isolated or purified nucleic acid molecule comprises a nucleotide sequence encoding a mutant plant acyl-ACP TE, which comprises a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2. The isolated or purified nucleic acid molecule can be a vector. The encoded mutant plant acyl-ACP TE can further comprise a substrate specificity-altering mutation in the region corresponding to amino acids 118-167 of the mature amino acid of the *Cuphea viscosissima* acyl-ACP TE encoded by FatB2. The encoded mutant plant acyl-ACP TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The encoded mutant plant acyl-ACP TE can further comprise a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2.

Another host cell or organism is provided. The host cell or organism comprises the above-described isolated or purified nucleic acid molecule comprising a nucleotide sequence encoding a mutant plant acyl-ACP TE, which comprises a substrate specificity-altering mutation in the region corresponding to amino acids 118-167 of the mature amino acid sequence of the *Cuphea viscosissima* acyl-ACP TE encoded by FatB2.

An isolated or purified mutant plant acyl-ACP TE is also provided. The isolated or purified mutant plant acyl-ACP TE comprises a substrate specificity-altering mutation in the region corresponding to amino acids 118-167 of the mature amino acid sequence of the *Cuphea viscosissima* acyl-ACP TE encoded by FatB2. The mutant TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The mutant TE can further comprise a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2. The mutant TE can further comprise a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

Yet another isolated or purified mutant plant acyl-ACP TE is provided. The isolated or purified mutant plant acyl-ACP TE comprises a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2. The mutant TE can further comprise a substrate specificity-altering mutation in the region corresponding to amino acids 118-167 of the mature amino acid of the *Cuphea viscosissima* acyl-ACP TE encoded by FatB2. The mutant TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The mutant TE can further comprise a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2.

BRIEF DESCRIPTION OF THE FIGURES

FIG. 1 is a sequence alignment of deduced amino acid sequences of *C. nucifera* (Cn) (CnFatB2 [SEQ ID NO: 4], CnFatB1 [SEQ ID NO: 5], and CnFatB3 [SEQ ID NO: 6]) and *C. viscosissima* (Cv) (CvFatB1 [SEQ ID NO: 2], CvFatB2 [SEQ ID NO: 3], and CvFatB3 [SEQ ID NO: 1]) acyl-ACP TEs. The putative N-terminal amino acid residue of the mature protein is leucine (▼). Two arrows indicate the conserved regions from which the degenerated primers were designed. The N-terminal sequence of CvFatB2 is incomplete (*).

FIG. 8b shows the mole percentage of individual fatty acids (FAs) from 4:0 to 16:1 as well as the total FAs (μM) for each of 13 chimeric TEs (i.e., rTE4, rTE8, rTE16, rTE20, rTE24, rTE28, rTE32, rTE36, rTE40, rTE44, rTE52, rTE56 and rTE60) and *C. viscosissima* FatB1 (CvB1).

FIG. 9 lists the amino acid (single letter code) present at a given position in TE for the indicated organism.

DETAILED DESCRIPTION

Figure 2:
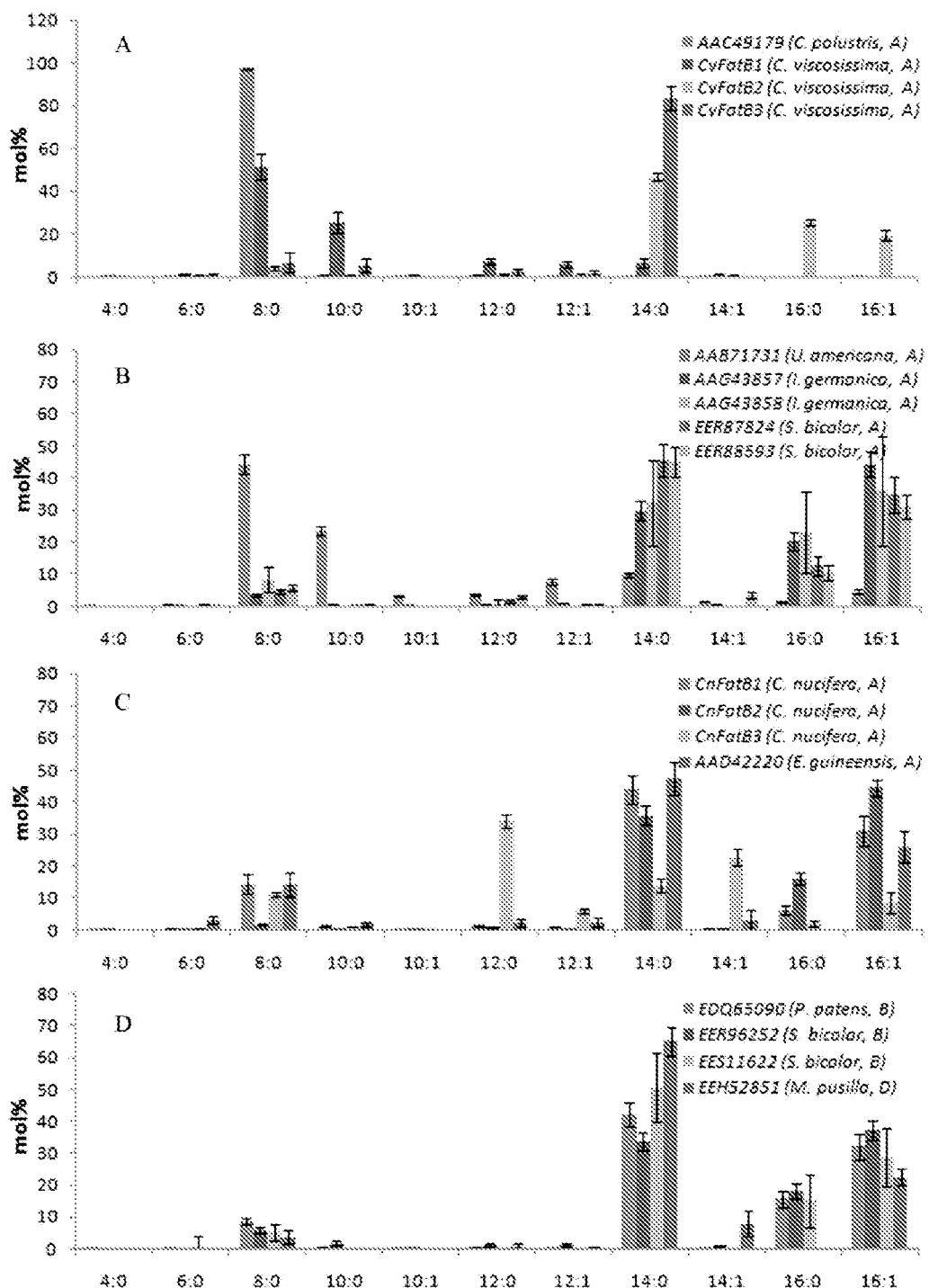
FIG. 2a is a bar graph showing the fatty acid composition of *E. coli* K27 cultures expressing acyl-ACP TE from *C. viscosissima* or *Cuphea palustris* (Subfamily A). In parentheses are the organism and the subfamily to which each sequence belongs. Error bars represent standard errors.
FIG. 2b is a bar graph showing the fatty acid composition of *E. coli* K27 cultures expressing acyl-ACP TE from *U. Americana, I. germanica*, or *S. bicolor* (Subfamily A). In parentheses are the organism and the subfamily to which each sequence belongs. Error bars represent standard errors.
FIG. 2c is a bar graph showing the fatty acid composition of *E. coli* K27 cultures expressing acyl-ACP TEs from *C. nucifera* or *E. guineensis* (Subfamily A). In parentheses is the organism and the subfamily to which each sequence belongs. Error bars represent standard errors.
FIG. 2d is a bar graph showing the fatty acid composition of *E. coli* K27 cultures expressing acyl-ACP TEs from *P. patens* (Subfamily B), *S. bicolor* (Subfamily B), or *M. pusilla* (Subfamily D). In parentheses are the organism and the subfamily to which each sequence belongs. Error bars represent standard errors.

The present disclosure is predicated, at least in part, on the discovery that expression of an acyl-acyl carrier protein (ACP) thioesterase (TE) from *Bryantella formatexigens* (DSM 14469, EET61113.1, ZP_05345975.3, C6LDQ9; Wolin et al., Appl. Environ. Microbiol. 69(10): 6321-6326 (October 2003); nucleotide sequence is SEQ ID NO: 23; amino acid sequence is SEQ ID NO: 24)) in a host cell or organism, such as *Escherichia coli*, results in an increase in the production of short-chain fatty acids in the host cell or organism. In this regard, it has been surprisingly and unexpectedly discovered that the introduction of two or more point mutations in the acyl-ACP TE of *B. formatexigens* has a synergistic effect on short-chain activity in the host cell or organism. The present disclosure is further predicated on the discovery that the substrate specificity and activity (e.g., total amount of fatty acids produced) of an acyl-ACP TE, such as a plant acyl-ACP TE, can be affected by introducing a substrate specificity-altering mutation in the region corresponding to amino acids 118-167, such as from about amino acid 118 to about amino acid 167, of the mature amino acid sequence of the *Cuphea viscosissima* acyl-ACP TE encoded by FatB2. The materials and methods have application for biofuels, industrial lubricants, food oils, and the like.

In view of the foregoing, a method of increasing production of fatty acids, such as short-chain fatty acids and/or fatty acids having from about six to about 12 carbon atoms (C6-C12), such as fatty acids having from about 10 to about 12 carbon atoms (C10-C12), in a host cell or organism is provided. Thus, the method can be used to increase production of fatty acids having less than about 10 carbon atoms or fatty acids having less than about 12 carbon atoms. The method comprises introducing into the host cell or organism and expressing therein a nucleic acid molecule comprising a nucleotide sequence encoding an acyl-ACP TE, such as an acyl-ACP TE from FIG. 5, FIG. 9, Table 1, Table 2, or www.enzyme.cbirc.iastate.edu (such as family TE14), in particular an acyl-ACP TE from a bacterium, e.g., an acyl-ACP TE from *Bryantella formatexigens*. By "short-chain fatty acids" is meant fatty acids containing six carbons or less. By "increasing production" is meant an increase in the production of fatty acids (such as short-chain fatty acids and/or fatty acids having from about six to about 12 carbon atoms, e.g., fatty acids having from about 10 to about 12 carbon atoms, and the like) such as by at least about 5% (or 10%, 15%, 20%, 25%, 30%, 35%, 40%, 45%, 50%, 55%, 60%, 65%, 70%, 75%, 80%, 85%, 90%, 95%, 100%, or even greater) as compared to the production of fatty acids, such as short-chain fatty acids and/or fatty acids having from about six to about 12 carbon atoms, such as fatty acids having from about 10 to about 12 carbon atoms, and the like, in the wild-type host organism. An increase in the production of one class of fatty acids, such as short-chain fatty acids and/or fatty acids having from about six to about 12 carbon atoms, such as fatty acids having from about 10 to about 12 carbon atoms, may or may not be reflected in an increase in the overall production of fatty acids. For example, an increase in the production of one class of fatty acids, such as short-chain fatty acids, may be accompanied by a decrease in the production of fatty acids of other chain lengths, such as medium chain lengths or long chain lengths. In this regard, the introduction into the host cell or organism and expression therein of a nucleic acid comprising a nucleotide sequence encoding a different TE, such as one described herein (see, e.g., FIG. 5, FIG. 9, Table 1, Table 2, or www.enzyme.cbirc.iastate.edu (e.g., family TE14)), can result in an increase in the production of fatty acids containing, for example, eight, 10, 12, 14, 16, or more carbons.

Another method of increasing production of fatty acids, such as short-chain fatty acids and/or fatty acids having from about six to about 12 carbon atoms (C6-C12), such as fatty acids having from about 10 to about 12 carbon atoms (C10-C12), in a host cell or organism is also provided. The method comprises introducing into the host cell or organism and expressing therein a nucleic acid molecule comprising a nucleotide sequence encoding a mutant acyl-ACP TE derived from a wild-type acyl-ACP TE, such as an acyl-ACP TE from FIG. 5, FIG. 9, Table 1, Table 2, or www.enzyme.cbirc.iastate.edu (e.g., family TE14), in particular an acyl-ACP TE from a bacterium, e.g., an acyl-ACP TE from *Bryantella formatexigens*. The mutant acyl-ACP TE produces more fatty acids, such as short-chain fatty acids, in the host cell or organism than the corresponding wild-type (also referred to as "native") acyl-ACP TE. "Short-chain fatty acids" and "increasing production" are as described above. Preferably, the mutant acyl-ACP TE derived from wild-type *Bryantella formatexigens* acyl-ACP TE differs from wild-type *Bryantella formatexigens* acyl-ACP TE by two or more amino acid mutations comprising N169Y and S222I and has increased thioesterase activity compared to wild-type *Bryantella formatexigens* acyl-ACP TE.

A method of making a mutant *Bryantella formatexigens* acyl-ACP TE is also provided. The method comprises making a mutant *Bryantella formatexigens* acyl-ACP TE comprising two or more amino acid mutations comprising N169Y and S222I. Preferably, and even desirably, the mutant *Bryantella formatexigens* acyl-ACP TE has increased thioesterase activity compared to a corresponding wild-type *Bryantella formatexigens* acyl-ACP TE. Mutant acyl-ACP TEs can be derived from such wild-type acyl-ACP TEs in accordance with methods known in the art and exemplified herein.

Also provided is a method of making a chimeric *Cuphea viscosissima* acyl-ACP TE. Any suitable method of making a chimera as known in the art and exemplified herein can be used. The method can comprise replacing a segment of a wild-type *Cuphea viscosissima* acyl-ACP TE with a segment of another acyl-ACP TE. Examples of wild-type *Cuphea viscosissima* acyl-ACP TEs include those encoded by the FatB1 gene (designated CvFatB1) and the FatB2 gene (designated CvFatB2). Any suitable acyl-ACP TE (see, e.g., FIG. 5, FIG. 9, Table 1, Table 2, and www.enzyme.cbirc.iastate.edu (e.g., family TE14), which website is hereby incorporated by reference for its teachings regarding acyl-ACP TEs) can serve as the source of the segment that is used to replace the segment of the wild-type *Cuphea viscosissima* acyl-ACP TE. Preferably, the acyl-ACP TE gene is another *Cuphea viscosissima* acyl-ACP TE. The method can, and preferably does, comprise replacing a segment of the CvFatB1 gene with a segment of another acyl-ACP TE gene to produce a chimeric CvFatB1 gene or replacing a segment of a CvFatB2 gene with a segment of another acyl-ACP TE gene to produce a chimeric CvFatB2 gene. In this regard, the method can comprise replacing a segment of a wild-type CvFatB1 gene with a segment of a CvFatB2 gene or replacing a segment of a wild-type CvFatB2 gene with a segment of a CvFatB1 gene. Preferably, and even desirably, the chimeric *Cuphea viscosissima* acyl-ACP TE encodes a chimeric acyl-ACP TE, which (i) has a substrate specificity that differs from the corresponding wild-type *Cuphea viscosissima* acyl-ACP TE, (ii) produces a total amount of fatty acids that differs from the total amount of fatty acids produced by the corresponding wild-type *Cuphea viscosissima* acyl-ACP TE, or (iii) has a substrate specificity and produces a total amount of fatty acids, both of which differ from the corresponding wild-type *Cuphea viscosissima* acyl-ACP TE. For example, substrate specificity can be changed from a broad-range specificity, a C8 specificity, or a C14/C16 specificity to one of the others or a specificity for a different chain length, such as C4, C6, C8, C10, C12, C14, or C16 (see, e.g., FIG. 5 and Table 2). A difference in substrate specificity can result in the production of a fatty acid not produced by the wild-type TE or the absence of production of a fatty acid produced by the wild-type TE. Activity levels by the chimeric TE, such as the total amount of fatty acids produced, can be increased or decreased compared to activity levels by the corresponding wild-type TE. Preferably, activity levels are increased.

TABLE 1

Acyl-ACP TEs

| Organism | GenBank ID No. | Ref Seq | Uni Prot |
|---|---|---|---|
| BACTERIA | | | |
| *Acetivibrio cellulolyticus* CD2 | | ZP_09465585.1 | |
| *Acetobacterium woodii* (strain ATCC 29683/DSM 1030/JCM 2381/KCTC 1655) | AFA47597.1 | YP_005268486.1 | H6LB45 |
| *Akkermansia muciniphila* (strain ATCC BAA-835) | ACD05543.1 | YP_001878324.1 | B2UMI7 |
| *Alistipes finegoldii* DSM 17242 | AFL79015.1 | YP_006411700.1 | |
| *Alistipes shahii* WAL 8301 | CBK64996.1 | | D4IPY4 |
| *Alistipes* sp. HGB5 | EFR57355.1 | ZP_08514792.1 | E4MCC6 |
| *Alkaliphilus oremlandii* (strain OhILAs) (*Clostridium oremlandii* strain OhILAs) | ABW18441.1 | YP_001512437.1 | A8MEW2 |
| *Anaeromyxobacter dehalogenans* (strain 2CP-1/ATCC BAA-258) | ACL67544.1 | YP_002494610.1 | B8JAP5 |
| *Anaeromyxobacter* sp. (strain Fw109-5) | ABS24558.1 | YP_001377542.1 | A7H762 |
| *Anaeromyxobacter* sp. (strain K) | ACG75405.1 | YP_002136534.1 | B4UHZ1 |
| *Anaerophaga* sp. HS1 | | ZP_09483366.1 | |
| *Anaerophaga thermohalophila* DSM 12881 | | ZP_08844891.1 | |
| *Anaerostipes* sp. 3_2_56FAA | EFV23220.1 | ZP_07930626.1 | E5VSK1 |
| *Arcobacter nitrofigilis* (strain ATCC 33309/DSM 7299/LMG 7604/NCTC 12251/CI) (*Campylobacter nitrofigilis*) | ADG93695.1 | YP_003656202.1 | D5V083 |
| *Arcobacter* sp. L. | BAK73293.1 | YP_005553610.1 | G2HVZ0 |
| *Atopobium parvulum* (strain ATCC 33793/DSM 20469/JCM 10300/VPI 0546) (*Streptococcus parvulus*) (*Peptostreptococcus parvulus*) | ACV51065.1 | YP_003159656.1 | C8WAC7 |
| *Bacillus coagulans* (strain 2-6) | AEH52240.1 | YP_004567626.1 | F7Z1I0 |
| *Bacteroides clarus* YIT 12056 | EGF49737.1 | ZP_08298226.1 | F3PL79 |
| *Bacteroides coprosuis* DSM 18011 | EGJ70302.1 | ZP_08457284.1 | F3ZP75 |
| *Bacteroides dorei* 5_1_36/D4 | EEB23554.1 | ZP_03302607.1 | B6W3R2 |
| | EEO44480.1 | ZP_08794675.1 | C3R613 |
| *Bacteroides eggerthii* 1_2_48FAA | EFV30016.1 | ZP_07934757.1 | E5WYK7 |
| *Bacteroides faecis* MAJ27 | | ZP_09861604.1 | |
| *Bacteroides fluxus* YIT 12057 | EGF58556.1 | ZP_08299596.1 | F3PR15 |
| *Bacteroides fragilis* (strain YCH46) | BAD50502.1 | YP_101036.1 | Q64PS9 |
| *Bacteroides fragilis* 3_1_12 | EFR55122.1 | ZP_07811188.1 | E4W011 |
| *Bacteroides helcogenes* (strain ATCC 35417/DSM/20613/JCM 6297/P 36-108) | ADV45243.1 | YP_004162829.1 | E6ST39 |
| *Bacteroides ovatus* SD CC 2a | EFF59010.1 | ZP_06721668.1 | D4WRN0 |

TABLE 1-continued

| Acyl-ACP TEs | | | |
|---|---|---|---|
| Organism | GenBank ID No. | Ref Seq | Uni Prot |
| *Bacteroides salanitronis* (strain DSM 18170/JCM 13567/BL78) | ADY35429.1 | YP_004257902.1 | F0R2N4 |
| *Bacteroides* sp. 1_1_14 | EFI05067.1 | ZP_06994617.1 | D7IBR2 |
| *Bacteroides* sp. 20_3 | EEY82391.1 | ZP_05286609.1 | D0TGY7 |
| | EFK61224.1 | ZP_06076697.1 ZP_07217422.1 | E1YZ05 |
| *Bacteroides* sp. 3_1_19 | EFI08712.1 | ZP_06985974.1 | D7IRY5 |
| *Bacteroides* sp. 3_1_23 | EEO56440.1 | ZP_04550578.1 | C3QWV6 |
| | EFI38044.1 | ZP_07041038.1 | D7K661 |
| *Bacteroides* sp. 3_1_33FAA | EEO60747.1 | ZP_04541663.1 | C3PZJ8 |
| | EEZ23120.1 | ZP_06086837.1 | D1JYR1 |
| *Bacteroides* sp. 3_1_40A | EET16328.1 | ZP_07997247.1 | C6Z619 |
| | EFV66622.1 | ZP_08799591.1 | E5UVX5 |
| *Bacteroides* sp. 4_1_36 | EFV26096.1 | ZP_07938734.1 | E5VAR7 |
| *Bacteroides* sp. D22 | EEO50828.1 | ZP_06083560.1 | C3QFU4 |
| | EEZ04805.1 | ZP_06997928.1 | D0TQX4 |
| | EFI15679.1 | ZP_08787276.1 | D7IYC1 |
| *Bacteroides thetaiotaomicron* (strain ATCC 29148/DSM 2079/NCTC 10582/E50/VPI-5482) | AAO77182.1 | NP_810988.1 | Q8A611 |
| *Bacteroides vulgates* (strain ATCC 8482/DSM 1447/NCTC 11154) | ABR40214.1 | YP_001299836.1 | A6L3F0 |
| | EFG15793.1 | ZP_06744316.1 | D4VE79 |
| *Bacteroides xylanisolvens* SD CC 1b. | EFG15675.1 | ZP_06764643.1 | D4VEU2 |
| *Bacteorides xylanisolvens* XB1A | CBK66370.1 | | D6D8M5 |
| *Bilophila wadsworthia* 3_1_6 | EFV45711.1 | ZP_07943134.1 | E5Y2P2 |
| butyrate-producing bacterium SS3/4 | CBL41593.1 | | D7GUV1 |
| butyrate-producing bacterium SSC/2 | CBL38064.1 | | D4MZL9 |
| *Butyrivibrio crossotus* DSM 2876 | EFF67558.1 | ZP_05793158.1 | D4S2V3 |
| *Butyrivibrio fibrisolvens* | CBK73219.1 | | D4IZD0 |
| *Butyrivibrio proteoclasticus* (strain ATCC 51982/DSM 14932/B316) *Clostridium proteoclasticum*) | ADL35342.1 | YP_003831924.1 | E0RY84 |
| *Calditerrivibrio nitroreducens* (strain DSM 19672/NBRC 101217/Yu37-1) | ADR19107.1 | YP_004051270.1 | E4TIX5 |
| *Caldithrix abyssi* DSM 13497 | EHO418883.1 | ZP_09550215.1 | H1XX98 |
| *Capnocytophaga gingivalis* ATCC 33624 | EEK15190.1 | ZP_04057029.1 | C2M393 |
| *Capnocytophaga ochracea* (strain ATCC 27872/DSM 7271/JCM 12966/VPI 2845) (*Bacteroides ochraceus*) | ACU91765.1 | YP_003140326.1 | C7M565 |
| *Capnocytophaga ochracea* F0287 | EFS97621.1 | ZP_07866279.1 | E4MRT3 |
| *Capnocytophaga* sp. oral taxon 329 str. F0087 | EGJ52443.1 | ZP_08450270.1 | F3Y4U4 |
| *Capnocytophaga* sp. oral taxon 329 str. F0087 | EGJ54408.1 | ZP_08448171.1 | F3XZ88 |
| *Capnocytophaga* sp. oral taxon 338 str. F0234 | EGD34946.1 | ZP_08201032.1 | F0IDA8 |
| *Capnocytophaga sputigena* ATCC 33612 | EEB66819.1 | ZP_03389980.1 | E2MZN9 |
| *Carnobacterium maltaromaticum* ATCC 35586 | | ZP_10276496.1 | |
| *Carnobacterium* sp. (strain 17-4) | AEB30554.1 | YP_004375570.1 | F4BN85 |
| *Cellulosilyticum lentocellum* (strain ATCC 49066/DSM 5427/NCIMB 11756/RHM5) (*Clostridum lentocellum*) | ADZ85723.1 | YP_004310921.1 | F2JL78 |
| *Cellulosilyticum lentocellum* (strain ATCC 49066/DSM 5427/NCIMB 11756/RHM5) (*Clostridium lentocellum*) | ADZ84608.1 | YP_004309806.1 | F2JLT2 |
| *Clostridium acetobutylicum* (strain ATCC 824/DSM 792/JCM 1419/LMG 5710/VKM B-1787) | AAK81514.1 | NP_350174.1 | F0KBI3 |
| | ADZ22635.1 | YP_004638245.1 | F7ZTD9 |
| | AEI32944.1 | YP_005672730.1 | Q97D89 |
| *Clostridium beijerinckii* (strain ATCC 51743/NCIMB 8052) (*Clostridium acetobutylicum*) | ABR37178.1 | YP_001312134.1 | A6M3J8 |
| *Clostridium beijerinckii* (strain ATCC 51743/NCIMB 8052) (*Clostridium acetobutylicum*) | ABR32877.1 | YP_001307833.1 | A6LR97 |
| *Clostridium botulinum* (strain 657/Type Ba4) | ACQ55199.1 | YP_002864623.1 | B1QMJ6 |
| | EDT85214.1 | ZP_02618356.1 | C3KWG6 |
| *Clostridium botulinum* (strain Alaska E43/Type E3) | ACD52320.1 | YP_001922691.1 | B2V1S4 |
| *Clostridium botulinum* (strain ATCC 19397/Type A) | ABS34504.1 | YP_001256092.1 | A5I7Y7 |
| | ABS37570.1 | YP_001385928.1 | A7FZF7 |
| | CAL85172.1 | YP_001389335.1 | |

TABLE 1-continued

| Acyl-ACP TEs | | | |
|---|---|---|---|
| Organism | GenBank ID No. | Ref Seq | Uni Prot |
| *Clostridium botulinum* (strain Eklund 17B/Type B) | ACD25059.1 | YP_001887708.1 | B2TRE2 |
| *Clostridium botulinum* (strain H04402 065/Type A5) | ABS42332.1 | YP_001392970.1 | A7GJL0 |
| | ACA45501.1 | YP_001783249.1 | B1IHP0 |
| | ADG01324.1 | YP_005676524.1 | D5VZ84 |
| | CBZ05511.1 | YP_005680239.1 | E8ZRC8 |
| *Clostridium botulinum* (strain Kyoto/Type A2) | ACO86035.1 | YP_002806157.1 | B1QFF4 |
| | EDT80125.1 | ZP_02615745.1 | C1FNL6 |
| *Clostridium botulinum* (strain Loch Maree/Type A3 | ACA57020.1 | YP_001788956.1 | B1KU83 |
| *Clostridium botulinum* BKT015925 | AEB74722.1 | YP_004394719.1 | F4A6R7 |
| *Clostridium botulinum* C str. Eklund | EDS76894.1 | ZP_02621951.1 | B1BC83 |
| *Clostridium botulinum* C str. Stockholm | EGO89051.1 | | F7MJC2 |
| *Clostridium botulinum* D str. 1873 | EES92019.1 | ZP_04862128.1 | C5VPS2 |
| *Clostridium botulinum* E1 str. 'BoNT E Beluga' | EES49023.1 | ZP_04821738.1 | C5UVX9 |
| *Clostridium butyricum* E4 str. BoNT E BL5262 | EDT76365.1 | ZP_02948643.1 | B1QU73 |
| | EEP52456.1 | ZP_04529638.1 | C4IMU3 |
| *Clostridium carboxidivorans* P7 | EET84629.1 | ZP_05394929.1 | C6Q1L2 |
| | EFG87972.1 | ZP_06855226.1 | |
| *Clostridium cellulolyticum* (strain ATCC 35319/DSM 5812/JCM 6584/H10) | ACL76790.1 | YP_002506770.1 | B8I625 |
| *Clostridium cellulovorans* (strain ATCC 35296/DSM 3052/OCM 3/743B) | ADL54009.1 | YP_003845773.1 | D9SPA7 |
| | | ZP_07630281.1 | |
| *Clostridium hahtewayi* DSM 13479 | EFC97397.1 | ZP_06116072.2 | D3ALA6 |
| *Clostridium novyi* (strain NT) | ABK60402.1 | YP_877012.1 | A0PXB0 |
| *Clostridium papyrosolvens* DSM 2782 | EGD46508.1 | ZP_08194021.1 | F1TGE3 |
| *Clostridium perfringens* (strain ATCC 13124/NCTC 8237/Type A) | ABG82470.1 | YP_697308.1 | Q0TM32 |
| *Clostridium perfringens* (strain ATCC 13124/NCTC 8237/Type A) | ABG83514.1 | YP_697307.1 | B1BYH2 |
| | EDT13255.1 | ZP_02634160.1 | B1R6C7 |
| | EDT24316.1 | ZP_02635484.1 | Q0TM33 |
| *Clostridium perfringens* (strain SM101/Type A) | ABG85584.1 | YP_699873.1 | Q0SPT4 |
| *Clostridium perfringens* CPE str. F4969 | EDT25816.1 | ZP_02640550.1 | B1RJP3 |
| *Clostridium perfringens* CPE str. F4969 | EDT25796.1 | ZP_02640551.1 | B1RJP4 |
| *Clostridium perfringens* F262 | EIA15751.1 | | H7CZX6 |
| *Clostridium perfringens* F262 | EDS81696.1 | ZP_02643956.1 | B1BEU6 |
| | EDT77142.1 | ZP_02863338.1 | B1RTS9 |
| | EIA15750.1 | | H7CZX5 |
| *Clostridium phytofermentans* (strain ATCC 700394/DSM 18823/ISDg) | ABX40638.1 | YP_001557377.1 | A9KS07 |
| *Clostridium saccharolyticum* (strain ATCC 35040/DSM 2544/NRCC 2533 WM1) | ADL03414.1 | YP_003821037.1 | D9R5Y0 |
| *Clostridium saccharolyticum* | CBK77093.1 | | D6DHB9 |
| *Clostridium* sp. 7_2_43FAA | EEH99678.1 | ZP_05132784.1 | C1IBG7 |
| *Clostridium* sp. 7_2_43FAA | EEH97843.1 | ZP_05130949.1 | C1I6P2 |
| *Clostridium* sp. BNL1100 | AEY65028.1 | YP_005146833.1 | H2JCC1 |
| *Clostridium* sp. DL-VIII | EHI96936.1 | ZP_09202343.1 | G7MBI0 |
| *Clostridium* sp. M62/1 | EFE13917.1 | ZP_06345069.2 | D4C8T0 |
| *Clostridium sporogenes* PA 3679 | EHN13726.1 | | G9F4F0 |
| *Clostridium tetani* (strain Massachusetts/E88) | AAO34771.1 | NP_780834.1 | Q899Q1 |
| *Clostridium thermocellum* (strain DSM 1313/LMG 6656/LQ8) | ABN54268.1 | YP_001039461.1 | A3DJY9 |
| | ADU73702.1 | YP_005687153.1 | C7HJ46 |
| | EEU00270.1 | ZP_05430844.1 | D1NHY5 |
| | EFB38222.1 | ZP_06247582.1 | E6UU77 |
| | EIC03340.1 | | H8EG82 |
| | EIC10345.1 | | H8ERY8 |
| *Coprococcus catus* GD/7 | CBK80368.1 | | D4J7P7 |
| *Coprococcus* sp. ART55/1 | CBK82356.1 | | D5HHV1 |
| *Cryptobacterium curtum* (strain ATCC 700683/DSM 15641/12-3) | ACU95033.1 | YP_003151715.1 | C7ML86 |
| *Deferribacter desulfuricans* (strain DSM 14783/JCM 11476/NBRC 101012/SSM1) | BAI79538.1 | YP_003495294.1 | D3PAB5 |
| *Denitrovibrio acetiphilus* (strain DSM 12809/N2460) | ADD68769.1 | YP_003504725.1 | D4H1K9 |
| *Desulfatibacillum alkenivorans* (strain AK-01) | ACL04336.1 | YP_002431804.1 | B8FIU5 |
| *Desulfitobacterium dehalogenans* ATCC 51507 | AFM00949.1 | YP_006430742.1 | |

TABLE 1-continued

| Acyl-ACP TEs | | | |
|---|---|---|---|
| Organism | GenBank ID No. | Ref Seq | Uni Prot |
| *Desulfitobacterium hafniense* (strain DCB-2/DSM 10664) | ACL21191.1 | YP_002459627.1 | B8G1D8 |
| *Desulfitobacterium metallireducens* DSM 15288 | EHC09806.1 | ZP_08979048.1 | G6GL79 |
| *Desulfobacterium autotrophicum* (strain ATCC 49314/DSM 3382/HRM2) | ACN14977.1 | YP_002603141.1 | C0QBW5 |
| *Desulfococcus oleovorans* (strain DSM 6200/Hxd3) | ABW68393.1 | YP_001530470.1 | A8ZWR2 |
| *Desulfohalobium retbaense* (strain DSM 5692) | ACV69537.1 | YP_003199115.1 | C8X540 |
| *Desulfomicrobium baculatum* (strain DSM 4028/VKM B-1378) (*Desulfovibrio baculatus*) | ACU90117.1 | YP_003158533.1 | C7LNE8 |
| *Desulfonatronospira thiodismutans* ASO3-1 | EFI34439.1 | ZP_07016503.1 | D6SNW3 |
| *Desulfosporosinus meridiei* DSM 13257 | EHC14266.1 | ZP_08981281.1 | G6G6K3 |
| *Desulfosporosinus orientis* (strain ATCC 19365/DSM 765/NCIMB 8382/VKM B-1628) (*Desulfotomaculum orientis*) | AET66411.1 | YP_004968926.1 | G7W7Y5 |
| *Desulfosporosinus youngiae* DSM 17734 | EHQ87820.1 | ZP_09652397.1 | H5Y1R7 |
| *Desulfotomaculum carboxydivorans* (strain DSM 14880/VKM B-2319/CO-1-SRB) | AEF93400.1 | YP_004496312.1 | F6B7F0 |
| *Desulfotomaculum nigrificans* DSM 574 | EGB20954.1 | ZP_08115620.1 | F0DQC6 |
| *Desulfovibrio aespoeensis* (strain ATCC 700646/DSM 10631/Aspo-2) | ADU63859.1 | YP_004122605.1 | E6VY45 |
| *Desulfovibrio africanus* str. Walvis Bay | EGJ50649.1 | YP_005052308.1 | F3YXU7 |
| *Desulfovibrio desulfuricans* (strain G20) | ABB38135.2 | YP_387830.2 | Q312L1 |
| *Desulfovibrio desulfuricans* ND132 | EGB14659.1 | YP_005167463.1 | F0JE50 |
| *Desulfovibrio salexigens* (strain ATCC 14822/DSM 2638/NCIB 8403/VKM B-1763) | ACS79414.1 | YP_002990953.1 | C6BRH4 |
| *Desulfovibrio* sp. A2 | EGY25981.1 | ZP_08865364.1 | G2H7B6 |
| *Desulfovibrio vulgaris* (strain Miyazaki F/DSM 19637) | ACL08376.1 | YP_002435844.1 | B8DRT9 |
| *Dethiosulfovibrio peptidovorans* DSM 11002 | EFC90467.1 | ZP_06391526.1 | D2Z4D8 |
| *Elusimicrobium minutum* (strain Pei191) | ACC98705.1 | YP_001876042.1 | B2KDV9 |
| *Enterococcus casseliflavus* ATCC 12755 | EGC68270.1 | ZP_08147098.1 | F0EPP5 |
| *Enterococcus casseliflavus* EC10 | EEV28127.1 | ZP_05644794.1 | C9ATN7 |
| | EEV34451.1 | ZP_05651118.1 | C9CHB4 |
| *Enterococcus casseliflavus* EC20 | EEV37743.1 | ZP_05654410.1 | C9A551 |
| *Enterococcus faecalis* (strain 62) | ADX78961.1 | YP_005704694.1 | C7CPH3 |
| | EET94418.1 | ZP_05421510.1 | C7U457 |
| | EEU22239.1 | ZP_05501873.1 | C7UJZ9 |
| | EEU64872.1 | ZP_05561915.1 | C7USW8 |
| | EEU70266.1 | ZP_05567309.1 | C7V886 |
| | EEU75370.1 | ZP_05574399.1 | C7VHP9 |
| | EEU76113.1 | ZP_05575142.1 | C7VYJ9 |
| | EEU81059.1 | ZP_05580088.1 | C7WCN3 |
| | EEU84199.1 | ZP_05583228.1 | C7WH64 |
| | EEU86888.1 | ZP_05592094.1 | C7WSC9 |
| | EEU92436.1 | ZP_05597642.1 | D4V053 |
| | EFG20655.1 | ZP_06745965.1 | F0PFE4 |
| *Enterococcus faecalis* (strain ATCC 47077/OG1RF) | AEA92939.1 | YP_005707309.1 | F2MNV7 |
| *Enterococcus faecalis* ATCC 29200 | EEN72504.1 | ZP_04437017.1 | C2H016 |
| *Enterococcus faecalis* DAPTO 512 | EFE15755.1 | ZP_06630131.1 | D4EIL1 |
| | EFE20531.1 | ZP_06631594.1 | D4EX30 |
| | EFQ10983.1 | ZP_07765336.1 | E2YB09 |
| | EFQ68629.1 | ZP_07768525.1 | E2YJM4 |
| *Enterococcus faecalis* Merz96 | EEU66704.1 | ZP_05563747.1 | C7VQU1 |
| | EEU78784.1 | ZP_05577813.1 | C7WV73 |
| *Enterococcus faecalis* T11 | EEU89934.1 | ZP_05595140.1 | C7V0W5 |
| *Enterococcus faecalis* T2 | EET97613.1 | ZP_05424705.1 | C7CYL8 |
| *Enterococcus faecalis* T8 | EEU15993.1 | ZP_05475136.1 | C7UCD7 |
| | EEU27232.1 | ZP_05557722.1 | C7Y8I5 |
| *Enterococcus faecalis* TUSoD Ef11 | EFK76243.1 | ZP_07108041.1 | E1EUM8 |

TABLE 1-continued

| Acyl-ACP TEs | | | |
|---|---|---|---|
| Organism | GenBank ID No. | Ref Seq | Uni Prot |
| *Enterococcus faecalis* TX0012 | EFT94231.1 | | E6I3I6 |
| *Enterococcus faecalis* TX0104 | EEI11131.1 | ZP_03949391.1 | C0X740 |
| *Enterococcus faecalis* TX0309B | EFU87020.1 | | E6GSL8 |
| | EFU94467.1 | | E6H424 |
| *Enterococcus faecalis* TX1467 | EFM69547.1 | ZP_07551346.1 | E0G5A0 |
| | EFM72961.1 | ZP_07553437.1 | E0GB90 |
| | EFM80076.1 | ZP_07562578.1 | E0GWQ0 |
| | EFM82210.1 | ZP_07568717.1 | E0H6A2 |
| | EFQ13284.1 | ZP_07759854.1 | E2Y3Z3 |
| | EFQ15104.1 | ZP_07764076.1 | E2YZ82 |
| | EFQ70935.1 | ZP_07770885.1 | E2Z4S5 |
| | EFT38179.1 | | E6F2Y1 |
| | EFT44150.1 | | E6F559 |
| | EFT47364.1 | | E6FHC7 |
| | EFT90826.1 | | E6FQ99 |
| | EFT97839.1 | | E6FWN8 |
| | EFU00982.1 | | E6G0U5 |
| | EFU02883.1 | | E6G9N2 |
| | EFU05122.1 | | E6GLN8 |
| | EFU10142.1 | | E6HEB6 |
| | EFU11766.1 | | E6HN77 |
| | EFU14622.1 | | E6HUS1 |
| | EFU16821.1 | | E6IDJ0 |
| | EFU88613.1 | | E6IKL5 |
| | EGG56243.1 | | F3R4H1 |
| *Enterococcus faecalis* TX2141 | EFT88049.1 | | E6IVY9 |
| *Enterococcus faecalis* TX4000 | EEN73225.1 | ZP_04436471.1 | C2DIA3 |
| | EFM65997.1 | ZP_07556393.1 | E0GJP6 |
| | EFM77239.1 | ZP_07572356.1 | E0HGP1 |
| | EFT40437.1 | | E6ESI6 |
| *Enterococcus faecium* (strain Aus0004) | AFC64296.1 | YP_005355414.1 | C9B6S0 |
| | EAN09806.1 | ZP_00603869.1 | C9BR75 |
| | EEV42502.1 | ZP_05659169.1 | C9BZH1 |
| | EEV46437.1 | ZP_05663104.1 | C9C309 |
| | EEV47997.1 | ZP_05664664.1 | C9CD36 |
| | EEV53223.1 | ZP_05669890.1 | D0AP61 |
| | EEV57800.1 | ZP_05674467.1 | D4QR52 |
| | EEW62756.1 | ZP_05831946.1 | D4QYX5 |
| | EFF21534.1 | ZP_06675770.1 | D4RSJ8 |
| | EFF29090.1 | ZP_06676257.1 | D4SPZ7 |
| | EFF30890.1 | ZP_06678973.1 | G9SNG7 |
| | EFF35697.1 | ZP_06701551.1 | G9SWE6 |
| | EHM36206.1 | | H8L8C1 |
| | EHM36898.1 | | Q3Y000 |
| *Enterococcus faecium* Com15 | EEV62230.1 | ZP_05678897.1 | C9AQE0 |
| *Enterococcus faecium* E1636 | EEW64692.1 | ZP_05923461.1 | D0AHZ9 |
| | EFD09525.1 | ZP_06446970.1 | D3LH99 |
| | EFF23086.1 | ZP_06695563.1 | D4RAG0 |
| *Enterococcus faecium* E1679 | EFF25207.1 | ZP_06699424.1 | D4RLH1 |
| *Enterococcus faecium* E980 | EFF38835.1 | ZP_06681449.1 | D4QHC6 |
| *Enterococcus faecium* PC4.1 | EEV51369.1 | ZP_05668036.1 | C9AJN9 |
| | EEV60229.1 | ZP_05676896.1 | C9BGE2 |
| | EFF61513.1 | ZP_06624194.1 | D4VWH8 |
| *Enterococcus faecium* TX0133a01 | AFK59819.1 | YP_006376801.1 | E4I8N4 |
| | EFR68006.1 | ZP_07846162.1 | E4IJA4 |
| | EFR70537.1 | ZP_07849882.1 | E4INZ4 |
| | EFR75054.1 | ZP_07851522.1 | EVIXY0 |
| | EFR77028.1 | ZP_07854658.1 | EVJAY8 |
| | EFS06349.1 | ZP_07859216.1 | EVJI68 |
| | EFS10037.1 | ZP_07861746.1 | |
| *Enterococcus faecium* TX1330 | EEI61496.1 | ZP_03980399.1 | C2H7W0 |
| *Enterococcus gallinarum* EG2 | EEV32970.1 | ZP_05649637.1 | C9A053 |
| *Enterococcus italicus* DSM 15952 | EFU73343.1 | ZP_07896506.1 | E6LHJ1 |
| *Ethanoligenens harbinense* (strain DSM 18485/JCM 12961/CGMCC 1.5033 YUAN-3) | ADU28280.1 | YP_004093011.1 | E6U8G1 |
| *Eubacterium cellulosolvens* 6 | EIM57815.1 | ZP_10167425.1 | |
| *Eubacterium limosum* (strain KIST612) | ADO35661.1 | YP_003958624.1 | E3GJ26 |
| *Eubacterium rectale* DSM 17629 | CBK89551.1 | | D6E2B1 |
| *Eubacterium rectal* M104/1 | CBK94159.1 | | D4JKL2 |
| *Eubacterium saburreum* DSM 3986 | EFU75440.1 | ZP_07905804.1 | E6LS63 |
| *Eubacterium siraeum* 70/3 | CBK97519.1 | | D4JWQ0 |
| *Eubacterium siraeum* V10Sc8a | CBL35446.1 | | D4MNW3 |
| *Faecalibacterium prausnitzii* L2-6 | CBK98400.1 | | D4K4F7 |
| *Fibrella aestuarina* BUZ 2 | CCG99613.1 | | I0K660 |
| *Fibrisoma limi* BUZ 3 | CCH55838.1 | | |

TABLE 1-continued

| Acyl-ACP TEs | | | |
|---|---|---|---|
| Organism | GenBank ID No. | Ref Seq | Uni Prot |
| *Fibrobacter succinogenes* (strain ATCC 19169/S85) | ACX75214.1 ADL24713.1 | YP_003249696.1 YP_005822012.1 | C9RRM8 |
| *Finegoldia magna* (strain ATCC 29328) (*Peptostreptococcus magnus*) | BAG08537.1 | YP_001692427.1 | B0S2E7 |
| *Finegoldia magna* SY403409CC001050417 | EFL54101.1 EGS34728.1 | ZP_07321135.1 | E1KXS7 F9MZ32 |
| *Flavobacterium columnare* (strain ATCC 49512/CIP 103533/TG 44/87) | AEW86359.1 | YP_004942152.1 | G8X6Z8 |
| *Flavobacterium frigoris* PS1 | EIA08417.1 | ZP_09895618.1 | H7FRY9 |
| *Flavobacterium johnsoniae* (Strain ATCC 17061/DSM 2064/UW101) *Cytophaga johnsonae* | ABQ06468.1 | YP_001195787.1 | A5FE97 |
| *Flavonifractor plautii* ATCC 29863 | EHM53486.1 | ZP_09383254.1 | G9YNF5 |
| *Flexistipes sinusarabici* (strain DSM 4947/MAS 10) | AEI14379.1 | YP_004602947.1 | F8E426 |
| *Fructobacillus fructosus* KCTC 3544 | | ZP_08660317.1 | |
| *Geobacillus* sp. (strain Y412MC10) | ACX63219.1 | YP_003241026.1 | D3EF08 |
| *Geobacter lovleyi* (Strain ATCC BAA-1151/DSM 17278/SZ) | ACD96083.1 | YP_001952603.1 | B3E596 |
| *Geobacter metallireducens* (strain GS-15/ATCC 53774/DSM 7210) | ABB31963.1 EHP86324.1 | YP_384688.1 | H1L7J4 Q39UW1 |
| *Geobacter* sp. (strain FRC-32) | ACM20973.1 | YP_002538074.1 | B9M0X0 |
| *Granulicatella adiacens* ATCC 49175 | EEW37696.1 | ZP_05737219.1 | C8NEY7 |
| *Granulicatella elegans* ATCC 700633 | EEW93633.1 | ZP_05851687.1 | D0BKN0 |
| *Haliscomenobacter hydrossis* (strain ATCC 27775/DSM 1100/LMG 10767 O) | AEE52567.1 | YP_004449440.1 | F4KWT4 |
| *Haloplasma contractile* SSD-17B | EGM25295.1 EGM26151.1 | ZP_08557504.1 ZP_08558128.1 | F7Q2G6 |
| *Jonquetella anthropi* DSM 22815 | EHM12447.1 | | H0ULI2 |
| *Jonquetella anthropi* E3_33 E1 | EEX49185.1 | ZP_05859848.1 | C9M5Q8 |
| *Lachnospiraceae bacterium* 5_1_63FAA | EFV17918.1 | ZP_07955084.1 | E5VG94 |
| *Lachnospiraceae bacterium* oral taxon 082 str. F0431 | EHO50163.1 | ZP_09561948.1 | H1LYH8 |
| *Lactobacillus acidipiscis* KCTC 13900 | | ZP_09456326.1 | |
| *Lactobacillus acidophilus* (strain 30SC) | ADZ06571.1 | YP_004286708.1 | F0TIR4 |
| *Lactobacillus aciophilus* (strain ATCC 700396/NCK56/N2/NCFM) | AAV42277.1 | YP_193308.1 | Q5FLZ7 |
| *Lactobacillus acidophilus* ATCC 4796 | EEJ76335.1 | ZP_04021090.1 | C2HMJ5 |
| *Lactobacillus amylolyticus* DSM 11664 | EFG55410.1 | ZP_06818559.1 | D4YTY9 |
| *Lactobacillus amylovorus* (strain GRL 1118) | ADQ58392.1 AEA31360.1 | YP_004031187.1 YP_005853365.1 | E4SLD4 F2M221 |
| *Lactobacillus animalis* KCTC 3501 | | ZP_08549496.1 | |
| *Lactobacillus brevis* (strain ATCC 367/JCM 1170) | ABJ63754.1 | YP_794785.1 | Q03SR8 |
| *Lactobacillus brevis* subsp. *gravesensis* ATCC 27305 | EEI69866.1 | ZP_03940727.1 | C2D5L9 |
| *Lactobacillus buchneri* (strain NRRL B-30929) | AEB73621.1 | YP_004398684.1 | F4FX93 |
| *Lactabacillus buchneri* ATCC 11577 | EEI18325.1 | ZP_03943743.1 | C0WUL3 |
| *Lactobacillus casei* (strain ATCC 334) | ABJ70998.1 ADK19433.1 AEA54746.1 AEA57928.1 | YP_003789283.1 YP_005857330.1 YP_005860469.1 YP_807440.1 | D8GB52 F2MA80 F2MJ21 Q035X4 |
| *Lactobacillus coleohominis* 101-4-CHN | EEU30164.1 | ZP_05553571.1 | C7XWA4 |
| *Lactobacillus crispatus* (strain ST1) | CBL49834.1 | YP_003600859.1 | D5H1E9 |
| *Lactobacillus crispatus* 125-2-CHN | EEU18812.1 | ZP_05550017.1 | C7XLF9 |
| *Lactobacillus crispatus* CTV-05 | EEJ70241.1 EEX28703.1 EFE00376.1 EFQ44288.1 | ZP_03995680.1 ZP_06020517.1 ZP_06626062.1 ZP_07789659.1 | C2KCV6 D0DJR2 D4FBS4 E3R4N0 |
| *Lactobacillus crispatus* MV-1A-US | EEU28844.1 | ZP_05554513.1 | C7Y3T1 |
| *Lactobacillus delbrueckii* subsp. *bulgaricus* (strain 2038) | ADY85572.1 | YP_005852596.1 | F0JZ70 |
| *Lactobacillus delbrueckii* subsp. *bulgaricus* (strain ATCC BAA-365) | ABJ58999.1 | YP_813437.1 | Q048X3 |
| *Lactobacillus delbrueckii* subsp. *bulgaricus* (strain ND02) | ADQ61561.1 | YP_004034538.1 | E4SWA3 |
| *Lactobacillus delbrueckii* subsp. *bulgaricus* PB2003/044-T3-4 | EFK32863.1 | ZP_07091661.1 | D8FL81 |
| *Lactobacillus delbrueckii* subsp. *lactis* DSM 20072 | EGD27772.1 | | F0HUG7 |
| *Lactobacillus farciminis* KCTC 3681 | | ZP_08576095.1 | |

TABLE 1-continued

| Acyl-ACP TEs | | | |
|---|---|---|---|
| Organism | GenBank ID No. | Ref Seq | Uni Prot |
| *Lactobacillus fermentum* (strain CECT 5716) | ADJ40858.1 | YP_005848352.1 | D8IGS7 |
| *Lactobacillus fructivorans* KCTC 3543 | | ZP_08652157.1 | |
| *Lactobacillus gasseri* (strain ATCC 33323/DSM 20243) | ABJ59782.1 | YP_814220.1 | Q045U0 |
| *Lactobacillus gasseri* 202-4 | EEQ26038.1 | ZP_04643995.1 | C4VSR8 |
| *Lactobacillus gasseri* 224-1 | EFB62115.1 | ZP_06262095.1 | D1YK76 |
| *Lactobacillus gasseri* JV-V03 | EFJ69165.1 | ZP_07058478.1 | D7V535 |
| *Lactobacillus gastricus* PS3 | EHS87218.1 | ZP_09786106.1 | H4GIM3 |
| *Lactobacillus helveticus* (strain H10) | ADX69593.1 | YP_005849580.1 | F0NV99 |
| *Lactobacillus helveticus* MTCC 5463 | EEW67886.1 EGF34731.1 | ZP_05752683.1 | C9M2C2 F3MQC6 |
| *Lactobacillus hilgardii* ATCC 8290 | EEI25650.1 | ZP_03952565.1 | C0XG64 |
| *Lactobacillus iners* AB-1 | | ZP-07267176.1 | |
| *Lactobacillus iners* ATCC 55195 | EEW51705.1 | ZP_05744259.1 | C8PCP7 |
| | EFO66686.1 | ZP_07697641.1 | E1NFD0 |
| | EFQ50621.1 | ZP_07732239.1 | E3BYM9 |
| | EFU79110.1 | ZP_07906033.1 | E6LSU2 |
| *Lactobacillus iners* LactinV 09V1-c | EFO67514.1 | ZP_07699507.1 | E1NKQ9 |
| *Lactobacillus iners* LEAF 3008A-a | EFQ51957.1 | ZP_07731033.1 | E3C233 |
| *Lactobacillus iners* SPIN 1401G | EFO69137.1 EGG31776.1 | ZP_07700645.1 ZP_08277548.1 | E1NP18 F3M0Y4 |
| *Lactobacillus iners* SPIN 2503V10-D | EFO71603.1 | ZP_07703903.1 | E1NYD0 |
| *Lactobacillus iners* UPII 143-D | EFQ47178.1 | ZP_07733650.1 | E3BU75 |
| | EFQ49253.1 | ZP_07735732.1 | E3BVE7 |
| | EGC79722.1 | ZP_08173986.1 | F0GLZ3 |
| *Lactobacillus iners* UPII 60-B | EGC80907.1 | ZP_08175329.1 | F0GQU0 |
| *Lactobacillus jensenii* 208-1 | EEQ24340.1 | ZP_04645666.1 | C4VMZ1 |
| | EEX27386.1 | ZP_05865781.1 | D0DNZ9 |
| | EFA93633.1 | ZP_06339831.1 | D1WHH0 |
| *Lactobacillus johnsonii* DPC 6026 | AEB92746.1 | YP_005861696.1 | F4AEU9 |
| *Lactobacillus johnsonii* pf01 | EGP13921.1 | | F7SCN1 |
| *Lactobacillus kefiranofaciens* (strain ZW3) | AEG39778.1 | YP_004561880.1 | F6CD69 |
| *Lactobacillus kisonensis* F0435 | EHO52285.1 | ZP_09555400.1 | H1LET0 |
| *Lactobacillus malefermentans* KCTC 3548 | | ZP_09441303.1 | |
| *Lactobacillus mali* KCTC 3596 = DSM 20444 | | ZP_09447064.1 | |
| *Lactobacillus mucosae* LM1 | EHT15844.1 | ZP_09815086.1 | H3RQN4 |
| *Lactobacillus oris* F0423 | EGS36091.1 | | F9JK82 |
| *Lactobacillus oris* PB013-T2-3 | EFQ53035.1 | ZP_07729836.1 | E3C864 |
| *Lactobacillus paracasei* subsp. *paracasei* 8700:2 | EEI68786.1 EEQ66724.1 | ZP_03963784.1 ZP_04673142.1 | C2FBR3 C5F8Y0 |
| *Lactobacillus parafarraginis* F0439 | EHL96655.1 | ZP_09393527.1 | G9ZRF4 |
| *Lactobacillus plantarum* (strain ATCC BAA-793/NCIMB 8826/WCFS1) | ADN97761.1 CCC78182.1 EFK27869.1 EHS83236.1 | YP_003923855.1 YP_004888696.1 ZP_07079657.1 | D7VG69 E1TKY4 F9ULU3 H3P172 |
| *Lactobacillus reuteri* (strain ATCC 55730/SD2112) | AEI57752.1 EEI64955.1 | YP_004650042.1 ZP_03975201.1 | C2GRC8 F8DLS3 |
| *Lactobacillus reuteri* 100-23 | EDX41870.1 | ZP_03074105.1 | B3XQR9 |
| *Lactobacillus rhamnosus* (strain ATCC 53103/GG) | BAI42696.1 CAR88152.1 EDY98171.1 EHJ21134.1 EHJ36340.1 | YP_003172003.1 YP_005866661.1 ZP_03212443.1 | B5QQB5 C7TEV9 G6AK63 G6JOH2 |
| *Lactobacillus rhamnosus* (strain Lc 705) | AER64996.1 CAR91083.1 EEN79670.1 | YP_003174934.1 YP_005873849.1 ZP_04441678.1 | C2JZ75 C7TLJ9 G7UXI5 |
| *Lactobacillus ruminis* (strain ATCC 27782/RF3) | AEN77890.1 | YP_004831826.1 | G2SMB8 |
| *Lactobacillus ruminis* SPM0211 | EFZ34938.1 EGM50173.1 EGX99156.1 | ZP_08080403.1 ZP_08564070.1 | E7FPK7 F7R2D3 |
| *Lactobacillus salivarius* (strain CECT 5713) | ADJ79282.1 | YP_005864069.1 | D8ILY0 |
| *Lactobacillus salivarius* (strain UCC118) | ABE00028.1 EEJ74495.1 | YP_536111.1 ZP_04009005.1 | C2EGC7 Q1WSV1 |
| *Lactobacillus salivarius* ACS-116-V-Col5a | EFK79641.1 | ZP_07206660.1 | E1JN74 |
| *Lactobacillus salvarius* GJ-24 | EGL99750.1 EGM52363.1 | | F5VCC4 F7QU96 |
| *Lactobacillus salivarius* SMXD51 | EIA32146.1 | | H7G0I9 |
| *Lactobacillus vaginalis* ATCC 49540 | EEJ40900.1 | ZP_03959573.1 | C2ETB7 |

TABLE 1-continued

| Acyl-ACP TEs | | | |
|---|---|---|---|
| Organism | GenBank ID No. | Ref Seq | Uni Prot |
| *Lactobacillus versmoldensis* KCTC 3814 | | ZP_09443147.1 | |
| *Lactobacillus zeae* KCTC 3804 | | ZP_09454130.1 | |
| *Lactococcus garvieae* IPLA 31405 | EIT66252.1 | | |
| *Lactococcus garvieae* (strain Lg2) | BAK58395.1 | YP_004779059.1 | F9V8F4 |
| (*Enterococcus seriolicida*) | BAK60363.1 | YP_005870647.1 | F9VDG2 |
| *Lactococcus lactis* subsp. *cremoris* (strain SK11) | ABJ72781.1 | YP_809203.1 | Q02Z41 |
| *Lactococcus lactis* subsp. *cremoris* A76 | AEU40439.1 | YP_005875862.1 | G8P2V5 |
| *Lactococcus lactis* subsp. *lactis* (strain CV56) | ADZ63759.1 | YP_005868493.1 | F2HJJ6 |
| | EHE92562.1 | | G6FES7 |
| *Lactococcus lactis* subsp. *lactis* IO-1 | BAL51042.1 | | H5SYX8 |
| *Leuconostoc citreum* (strain KM20) | ACA83334.1 | YP_001728778.1 | B1MVT0 |
| | CCF27846.1 | | H1WZU7 |
| *Leuconostoc citreum* LBAE C10 | CCF23736.1 | | H1WN37 |
| *Leuconostoc citreum* LBAE C11 | CCF26033.1 | | H1WUN4 |
| *Leuconostoc fallax* KCTC 3537 | | ZP_08313133.1 | |
| *Leuconostoc mesenteroides* subsp. *mesenteroides* (strain ATCC 8293/NCDO 523) | ABJ61410.1 | YP_005173661.1 | G7VJW8 |
| | AET29695.1 | YP_817783.1 | Q03ZG2 |
| *Leuconostoc pseudomesenteroides* KCTC 3652 | | ZP_08658910.1 | |
| *Leuconostoc pseudomesenteroides* KCTC 3652 | | ZP_08657880.1 | |
| *Marvinbryantia formatexigens* DSM 14469 | EET58368.1 | ZP_05348824.1 | C6LLV8 |
| *Melissococcus plutonius* (strain ATCC 35311/CIP 104052/LMG 20360/NCIMB 702443) | BAK22205.1 | YP_004457014.1 | F3YCH7 |
| *Melissococcus plutonius* (strain DAT561) | BAL61565.1 | YP_005319060.1 | H5T322 |
| *Mesotoga prima* MesG1.Ag.4.2 | AFK07784.1 | YP_006347027.1 | |
| *Microscilla marina* ATCC 23134 | EAY28464.1 | ZP_01690629.1 | A1ZMT4 |
| *Moorella thermoacetica* (strain ATCC 39073) | ABC20493.1 | YP_431036.1 | Q2RGE6 |
| *Myroides odoratus* DSM 2801 | EHQ43781.1 | ZP_09673466.1 | H1ZDF8 |
| *Odoribacter splanchnicus* (strain ATCC 29572/DSM 20712/JCM 15291/NCTC 10825/1651/6) (*Bacteroides splanchnicus*) | ADY34476.1 | YP_004254656.1 | F9ZBU7 |
| *Oenococcus kitaharae* DSM 17330 | EHN59872.1 | | G9WGP5 |
| *Olsenella uli* (strain ATCC 49627/DSM 7084/CIP 109912/JCM 12494/VPI D76D-27C) (*Lactobacillus uli*) | ADK67921.1 | YP_003800801.1 | E1QZV7 |
| *Opitutus terrae* (strain DSM 11246/PB90-1) | ACB75273.1 | YP_001817873.1 | B1ZXQ1 |
| *Ornithinibacillus scapharcae* TW25 | | ZP_08784004.1 | |
| *Paenibacillus dendritiformis* C454 | EHQ61755.1 | ZP_09676931.1 | H3SGM0 |
| *Paenibacillus lactis* 154 | EHB50198.1 | ZP_09004493.1 | G4HNN3 |
| *Paenibacillus* sp. HGF5 | EGG35794.1 | ZP_08280757.1 | F3MA61 |
| *Paenibacillus vortex* V453 | EFU42569.1 | ZP_07898346.1 | E5YSB9 |
| *Paludibacter propionicigenes* (strain DSM 17365/JCM 13257/WB4) | ADQ78301.1 | YP_004041286.1 | E4T0E2 |
| *Parabacteroides distasonis* (strain ATCC 8503/DSM 20701/NCTC 11152) | ABR43801.1 | YP_001303423.1 | A6LDN7 |
| *Parabacteroides* sp. D13 | EEU50458.1 | ZP_05546795.1 | C7XCA8 |
| *Paraprevotella clara* YIT 11840 | EHH00544.1 | ZP_09107765.1 | G5SQZ1 |
| *Paraprevotella xylaniphila* YIT 11841 | EGG54116.1 | ZP_08320615.1 | F3QU31 |
| *Pediococcus acidilactici* DSM 20284 | EFL95888.1 | ZP_07367805.1 | E0NFJ4 |
| *Pediococcus acidilactici* MA18/5M | EFA26407.1 | ZP_06197399.1 | D2EKP7 |
| | EHJ20298.1 | | G6IS05 |
| *Pediococcus pentosaceus* (strain ATCC 25745/183-1w) | ABJ68507.1 | YP_804949.1 | H8G000 |
| | CCG89967.1 | | Q03E65 |
| *Pelobacter propionicus* (strain DSM 2379) | ABL00830.1 | YP_902887.1 | A1AU09 |
| *Peptoniphilus harei* ACS-146-V-Sch2b | EFR32523.1 | ZP_07822609.1 | E4L0C9 |
| *Prevotella bivia* JCVIHMP010 | EFB92152.1 | ZP_06269388.1 | D1Y0N5 |
| | EIM31835.1 | | |
| *Prevotella buccae* ATCC 33574 | EFU30435.1 | ZP_07882963.1 | E6K8D5 |
| *Prevotella buccalis* ATCC 35310 | EFA92524.1 | ZP_06286413.1 | D1W477 |
| *Prevotella dentalis* DSM 3688 | EGQ16303.1 | ZP_08669671.1 | F9D1E1 |
| *Prevotella dentalis* DSM 3688 | EHO56109.1 | | H1MBA2 |
| *Prevotella denticola* (strain F0289) | AEA20475.1 | YP_004329120.1 | F2KTP5 |
| *Prevotella denticola* CRIS 18C-A | EGC84969.1 | ZP_08173659.1 | F0HB58 |
| *Prevotella disiens* FB035-09AN | EFL45598.1 | ZP_07323756.1 | E1KSA6 |

TABLE 1-continued

| Acyl-ACP TEs | | | |
|---|---|---|---|
| Organism | GenBank ID No. | Ref Seq | Uni Prot |
| *Prevotella intermedia* 17 | AFJ08475.1 | YP_006299246.1 | |
| *Prevotela marshii* DSM 16973 | EFM02212.1 | ZP_07365421.1 | E0NRS4 |
| *Prevotella melaninogenica* (strain ATCC 25845/DSM 7089/JCM 6325/VPI 2381/B282) (*Bacteroides melaninogenicus*) | ADK95990.1 | YP_003814035.1 | D9RUL0 |
| *Prevotella multiformis* DSM 16608 | EGC20653.1 | ZP_08135691.1 | F0F5N4 |
| *Prevotella multisaccharivorax* DSM 17128 | EGN58078.1 | ZP_08580508.1 | F8NCP3 |
| *Prevotella nigrescens* ATCC 33563 | EGQ15946.1 | ZP_08672539.1 | F9D9K9 |
| *Prevotella oralis* ATCC 33269 | EFZ37525.1 | ZP_08084447.1 | E7RP82 |
| *Prevotella oris* C735 | EFI48008.1 | ZP_07035544.1 | D7NEM6 |
| *Prevotella ruminicola* (strain ATCC 19189/JCM 8958/23) | ADE82257.1 | YP_003574402.1 | D5ERZ8 |
| *Prevotella salivae* DSM 15606 | EFV04584.1 | ZP_07961907.1 | E6MNZ7 |
| *Prevotella* sp. oral taxon 306 str. F0472 | EID32261.1 | ZP_09968086.1 | I0T9F8 |
| *Prevotella stercorea* DSM 18206 | EHJ38668.1 | ZP_09198687.1 | G6AZ54 |
| *Pseudoramibacter alactolyticus* ATCC 23263 | EFV02259.1 | ZP_07920643.1 | E6MF99 |
| *Rhodothermus marinus* (strain ATCC 43812/DSM 4252/R-10) *Rhodothermus obamensis*) | ACY48916.1 | YP_003291304.1 | D0MKK4 |
| *Rhodothermus marinus* SG0.5JP17-172 | AEN72763.1 | YP_004824600.1 | G2SK07 |
| *Roseburia hominis* (strain DSM 16839/NCIMB 14029/A2-183) | AEN95631.1 | YP_004837563.1 | G2T1Y7 |
| *Roseburia intestinalis* L1-82 | EEV02992.1 | ZP_04741938.1 | C7G5B5 |
| *Roseburia intestinalis* XB6B4 | CBL09912.1 | | D4KSR0 |
| | CBL12214.1 | | D4KXX4 |
| *Ruminococcus albus* (strain ATCC 27210/DSM 20455/JCM 14654/NCDO 2250/7) | ADU24217.1 | YP_004090103.1 | E6UKM1 |
| *Ruminococcus obeum* A2-162 | CBL24676.1 | | D4LV68 |
| *Ruminococcus* sp. SR1/5 | CBL20901.1 | | D4LM40 |
| *Ruminococcus torques* L2-14 | CBL26041.1 | | D4M479 |
| *Salinibacter ruber* (strain DSM 13855/M31) | ABC43900.1 | YP_444210.1 | Q2S6H1 |
| *Salinibacter ruber* (strain M8) | CBH22976.1 | YP_003569928.1 | D5H4M1 |
| *Sphaerochaeta pleomorpha* (strain ATCC BAA-1885/DSM 22778/Grapes) | AEV29849.1 | YP_005062859.1 | G8QR01 |
| *Sphingobacterium spiritovorum* ATCC 33300 | EEI90316.1 | ZP_03970072.1 | C2G3W1 |
| *Sphingobacterium spiritivorum* ATCC 33861 | EFK55869.1 | ZP_07082740.1 | D7VQ18 |
| *Spirochaeta africana* DSM 8902 | AFG37541.1 | YP_005475248.1 | H9UJ48 |
| *Sprochaeta caldaria* (strain ATCC 51460/DSM 7334/H1) | AEJ20927.1 | YP_004699435.1 | F8F2E5 |
| *Sprochaeta caldaria* (strain ATCC 51460/DSM 7334/H1) | AEJ18974.1 | YP_004697482.1 | F8F0B0 |
| *Spirochaeta coccoides* (strain ATCC BAA-1237/DSM 17374/SPN1) | AEC02997.1 | YP_004412379.1 | F4GLV6 |
| *Spirochaeta coccoides* (strain ATCC BAA-1237/DSM 17374/SPN1) | AEC02807.1 | YP_004412189.1 | F4GJR0 |
| *Spirochaeta smaragdinae* (strain DSM 11293/JCM 15392/SEBR 4228) | ADK83104.1 | YP_003805698.1 | E1R9D5 |
| *Spirochaeta smaragdinae* (strain DSM 11293/JCM 15392/SEBR 4228) | ADK82412.1 | YP_003805006.1 | E1RAP4 |
| *Spirochaeta thermophila* (strain ATCC 49972/DSM 6192/RI 19.B1) | ADN01075.1 | YP_003873348.1 | E0RU19 |
| *Spirochaeta thermophila* DSM 6578 | AEJ60373.1 | YP_006044090.1 | G0GBL4 |
| *Spirosoma linguale* (strain ATCC 33905/DSM 75/LMG 10896) | ADB42312.1 | YP_003391111.1 | D2QU30 |
| *Streptococcus anginosus* 1_2_62CV | EFW07929.1 | ZP_08013620.1 | E7GWK1 |
| *Streptococcus anginosus* CGUG 39159 | EID21884.1 | | I0SET1 |
| *Streptococcus anginosus* F0211 | EFU22895.1 | ZP_07863625.1 | E6IZR2 |
| *Streptococcus anginosus* SK52 = DSM 20563 | EGL47971.1 | ZP_08524336.1 | F5TZ42 |
| *Streptococcus australis* ATCC 700641 | EFV99485.1 | ZP_08021412.1 | E7SBM6 |
| | EGU64265.1 | | |
| *Streptococcus canis* FSL Z3-227 | EIQ82096.1 | ZP_10274029.1 | |
| *Streptococcus constellatus* subsp. *constellatus* SK53 | EID22796.1 | | I0SHE3 |
| *Streptococcus constellatus* subsp. *pharyngis* SK1060 = CCUG 46377 | EGV09466.1 | ZP_08762014.1 | F9P6H6 |
| *Streptococcus criceti* HS-6 | EHI74170.1 | ZP_09123331.1 | G5JTU8 |
| *Streptococcus cristatus* ATCC 51100 | EFX53291.1 | ZP_08059281.1 | E8JTL6 |
| | EGU66254.1 | | |

TABLE 1-continued

| Acyl-ACP TEs | | | |
|---|---|---|---|
| Organism | GenBank ID No. | Ref Seq | Uni Prot |
| *Streptococcus downei* F0415 | EFQ56787.1 | ZP_07726381.1 | E3CLH4 |
| *Streptococcus dysgalactiae* subsp. *equisimilis* (strain ATCC 12394/D166B) | ADX24753.1 | YP_006013333.1 | E8QAX7 |
| *Streptococcus dysgalactiae* subsp. *equisimilis* (strain GGS_124) | BAH81730.1 | YP_002996944.1 | C5WH65 |
| *Streptococcus dysgalactiae* subsp. *equismilis* SK1249 | EGL49418.1 | | F5U565 |
| *Streptococcus equi* subsp. *zooepidemicus* (strain ATCC 35246/C74-63) | AEJ25504.1 | | F8IMR8 |
| *Streptococcus equi* subsp. *zooepidemicus* (strain MGCS10565) | ACG62550.1 | YP_002123563.1 | B4U3I3 |
| *Streptococcus equines* ATCC 9812 | EFW88979.1 | ZP_08041402.1 | E8JP85 |
| *Streptococcus gallolyticus* subsp. *gallolyticus* TX20005 | EFM29278.1 | ZP_07464895.1 | E0PL23 |
| *Streptococcus ictaluri* 707-05 | EHI69863.1 | ZP_09126352.1 | G5K2J5 |
| *Streptococcus infantarius* (strain CJ18) | AEZ62572.1 | YP_005204043.1 | H6PBS3 |
| *Streptococcus infantis* ATCC 700779 | EFX36879.1<br>EIG40319.1 | ZP_08061125.1 | E8JZ60 |
| *Streptococcus infantis* SK1076 | EGL85964.1 | ZP_08523541.1 | F5W0Y7 |
| *Streptococcus infantis* SK1302 | EFO55275.1 | ZP_07692775.1 | E1M520 |
| *Streptococcus infantis* SK970 | EGV04542.1 | | F9PUI2 |
| *Streptococcus infantis* X | EGV15183.1 | | F9PB80 |
| *Streptococcus intermedius* SK54 | BAM23377.1<br>EID82512.1 | YP_006469625.1 | I0X1J6 |
| *Streptococcus macacae* NCTC 11558 | EHJ52132.1 | ZP_09134350.1 | G5JVK4 |
| *Streptococcus macedonicus* (strain ACA-DC 198) | CCF02741.1 | YP_005095067.1 | H2A7K5 |
| *Streptococcus mitis* (strain B6) | CBJ21968.1 | YP_003445836.1 | D3H7X6 |
| *Streptococcus mitis* ATCC 6249 | EFM31215.1 | ZP_07462962.1 | E0PS01 |
| *Streptococcus mitis* bv. 2 str. F0392 | EGR93006.1 | | F9P0J2 |
| *Streptococcus mitis* bv. 2 str. SK95 | EGU67810.1 | | F9LW41 |
| *Streptococcus mitis* NCTC 12261 | EFN95948.1 | ZP_07638954.1 | E1M0K5 |
| *Streptococcus mitis* SK1073 | EGP65457.1 | | F9HDJ2 |
| *Streptococcus mitis* SK1080 | EGP70417.1 | | F9HK06 |
| *Streptococcus mitis* SK569 | EGU71416.1 | | F9MHA3 |
| *Streptococcus mitis* SK575 | EID27575.1 | | I0SW22 |
| *Streptococcus mitis* SK579 | EID31778.1 | | I0T825 |
| *Streptococcus mitis* SK597 | EFO00396.1 | ZP_07641986.1 | E1LSZ7 |
| *Streptococcus mitis* SK616 | EID24616.1 | | I0SML3 |
| *Streptococcus oralis* SK10 | EIC79352.1 | | I0QDK0 |
| *Streptococcus oralis* SK100 | EIC76735.1 | | I0Q633 |
| *Streptococcus oralis* SK1074 | EID25784.1 | | I0SQY1 |
| *Streptococcus oralis* SK255 | EGL90926.1 | | F5VTF6 |
| *Streptococcus oralis* SK313 | EGV00858.1 | | F9Q4H5 |
| *Streptococcus oralis* SK610 | EIC75997.1 | | I0Q3Z5 |
| *Streptococcus parasanguinis* F0449 | EIG27302.1 | | |
| *Streptococcus parasanguinis* (strain ATCC 15912/DSM 6778/CIP 104372 LMG 14537) | AEH55709.1 | YP_004621637.1 | F8DI02 |
| *Streptococcus parasanguinis* ATCC 903 | EFX38996.1 | ZP_08063273.1 | E8K5A8 |
| *Streptococcus parasanguinis* F0405 | EFQ55999.1 | ZP_07726902.1 | E3CB49 |
| *Streptococcus parasanguinis* SK236 | EGU65274.1 | | F9M0Q9 |
| *Streptococcus parauberis* (strain KCTC 11537) | AEF25390.1 | YP_004479062.1 | F5ZIR6 |
| *Streptococcus parauberis* NCFD 2020 | EGE54640.1 | ZP_08246038.1 | F1Z1C3 |
| *Streptococcus peroris* ATCC 700780 | EFX40622.1 | ZP_08065211.1 | E8KB51 |
| *Streptococcus pneumoniae* (strain 670-6B) | ADM90954.1<br>EDK68094.1<br>EGI85205.1<br>EHD49693.1<br>EHD63537.1<br>EHD88133.1<br>EHE00949.1<br>EHE60798.1<br>EHZ08811.1<br>EIA01765.1<br>EIA03628.1 | YP_003879054.1<br>ZP_01830980.1 | A5MHD1<br>E0TMA5<br>F3VJ08<br>G6KXZ1<br>G6M938<br>G6NUS3<br>G6QQ59<br>G6VMF7<br>H7K7G8<br>H7NWY1<br>H7P9A4 |
| *Streptococcus pneumoniae* (strain 70585) | ACO16116.1<br>EDK66086.1<br>EHD28957.1<br>EHD89063.1 | YP_002740683.1<br>ZP_01827724.1<br>ZP_04524259.1<br>ZP_04598288.1 | A5M825<br>C1C807<br>G6JBH8<br>G6PTT6 |

TABLE 1-continued

| Acyl-ACP TEs | | | |
|---|---|---|---|
| Organism | GenBank ID No. | Ref Seq | Uni Prot |
| | EHE10731.1 | | G6RMA4 |
| | EHY96087.1 | | H7JGM5 |
| | EHZ58538.1 | | H7MCK4 |
| *Streptococcus pneumoniae* (strain Hungary 19A-6) | ACA37604.1 | YP_001694843.1 | A5MT27 |
| | EDK82213.1 | ZP_01834726.1 | B1ICK8 |
| | EHD56190.1 | | G6LGP3 |
| | EHZ17150.1 | | H7I8B3 |
| | EHZ26304.1 | | H7KWU0 |
| | EHZ51454.1 | | H7LTH4 |
| *Streptococcus pneumoniae* GA05245 | EGI85461.1 | | F3WAV6 |
| | EHE02013.1 | | G6R2M6 |
| | EHZ03819.1 | | H7PKX9 |
| *Streptococcus pneumoniae* GA11663 | EHE76579.1 | | G6P9A5 |
| *Streptococcus pneumoniae* GA13637 | EHD92416.1 | | G6Q076 |
| *Streptococcus pneumoniae* GA40028 | EDT91262.1 | ZP_02710611.1 | B2DHG4 |
| | EHE29264.1 | | G6T4S1 |
| | EHZ39486.1 | | H7NP72 |
| | EHZ97713.1 | | H7QAJ1 |
| *Streptococcus pneumoniae* GA40563 | EHZ44498.1 | | H7LG30 |
| *Streptococcus pneumoniae* GA41688 | EHE25505.1 | | G6SS73 |
| *Streptococcus pneumoniae* GA47373 | EHE36709.1 | | G6TER8 |
| *Streptococcus pneumoniae* GA47439 | EDT95056.1 | ZP_02715455.1 | B2DT86 |
| | EHE39175.1 | | G6TUT3 |
| *Streptococcus pneumoniae* GA47461 | EHZ60517.1 | | H7MHZ6 |
| *Streptococcus pneumoniae* GA47522 | EHD39940.1 | | G6K6A5 |
| | EHZ64825.1 | | H7HCA4 |
| | EHZ94055.1 | | H7MPL4 |
| *Streptococcus pneumoniae* GA47778 | EHD60478.1 | | G6LTP3 |
| | EHE14708.1 | | G6RV07 |
| | EHE17320.1 | | G6RZ73 |
| | EHE42733.1 | | G6U6L7 |
| *Streptococcus pneumoniae* GA49194 | EGJ14922.1 | | F3XKI1 |
| | EHZ72974.1 | | H7J3Y0 |
| | EHZ90787.1 | | H7NER5 |
| *Streptococcus pneumoniae* GA49542 | EDK79250.1 | ZP_01822626.1 | A5LTH7 |
| | EDT92444.1 | ZP_02713772.1 | B2DPR6 |
| | EGI84194.1 | | F3VP30 |
| | EHD76303.1 | | G6NBR6 |
| | EHE37076.1 | | G6TMQ1 |
| | EHE51720.1 | | G6UNS9 |
| | EHE67173.1 | | G6WCE5 |
| | EHZ48988.1 | | H7LJZ9 |
| | EHZ76888.1 | | H7NIU9 |
| *Streptococcus porcinus* str. Jelinkova 176 | EGJ26555.1 | ZP_08398558.1 | F3LB38 |
| *Streptococcus pseudopneumoniae* (strain IS7493) | AEL10828.1 | YP_004768688.1 | G0IAN6 |
| *Streptococcus pseudopneumoniae* SK674 | EID23674.1 | ZP_09992237.1 | I0SJX1 |
| | EID70047.1 | | I0W0Y1 |
| *Streptococcus pseudoporcinus* LQ 940-04 | EFR44687.1 | ZP_07823857.1 | E4L3R5 |
| | EHI65004.1 | | G5KAN5 |
| *Streptococcus pyogenes* HKU QMH11M0907901 | EIK42042.1 | | |
| *Streptococcus pyogenes* Alab49 | AEQ24391.1 | YP_006071945.1 | G4R4C7 |
| *Streptococcus pyogenes* ATCC 10782 | EFM33381.1 | ZP_07460727.1 | E0PWA2 |
| *Streptococcus pyogenes* MGAS1882 | AFC66139.1 | YP_005388837.1 | H8HAK4 |
| | AFC68003.1 | YP_005411534.1 | H8HE06 |
| *Streptococcus pyogenes* serotype M1 | AAZ51384.1 | YP_282129.1 | Q48Z34 |
| *Streptococcus pyogenes* serotype M12 (strain MGAS9429) | ABF32069.1 | YP_596613.1 | Q1JC16 |
| | ABF35892.1 | YP_600436.1 | Q1JM00 |
| *Streptococcus pyogenes* serotype M2 (strain MGAS10270) | ABF33948.1 | YP_598492.1 | Q1JH46 |
| *Streptococcus pyogenes* serotype M28 | AAX71858.1 | YP_280213.1 | Q48TU8 |
| *Streptococcus pyogenes* serotype M4 (strain MGAS10750) | ABF37868.1 | YP_602412.1 | Q1J6W5 |
| *Streptococcus pyogenes* serotype M6 | AAT86926.1 | YP_060109.1 | Q5XCD7 |
| *Streptococcus salivarius* (strain 57.1) | AEJ53614.2 | YP_006068477.1 | F8HDR2 |
| | EGX30167.1 | | G2GSH1 |
| *Streptococcus salivarius* SK126 | EEK10550.1 | ZP_04061476.1 | C2LQT3 |
| *Streptococcus sanguinis* ATCC 49296 | EFU62475.1 | ZP_07888343.1 | E6KNA8 |
| *Streptococcus sanguinis* SK1056 | EGJ39149.1 | | F3UB48 |
| *Streptococcus sanguinis* SK1057 | EGF06788.1 | | F2BSB3 |
| *Streptococcus sanguinis* SK1058 | EGF21443.1 | | F2CLJ1 |
| *Streptococcus sanguinis* SK1087 | EGG40307.1 | | F3SHX4 |
| *Streptococcus sanguinis* SK115 | EGD31794.1 | | F0I7V9 |
| *Streptococcus sanguinis* SK150 | EGD36508.1 | | F0IMN8 |

TABLE 1-continued

| Acyl-ACP TEs | | | |
|---|---|---|---|
| Organism | GenBank ID No. | Ref Seq | Uni Prot |
| *Streptococcus sanguinis* SK160 | EGD38300.1 | | F0IUP5 |
| *Streptococcus sanguinis* SK330 | EGF15598.1 | | F2C6E1 |
| *Streptococcus sanguinis* SK340 | EGJ44393.1 | | F3UHS5 |
| | EGQ20720.1 | | F9E0L5 |
| | EGQ24079.1 | | F9E949 |
| *Streptococcus sanguinis* SK353 | EFX93874.1 | ZP_08087316.1 | E8KPS1 |
| | EGC23179.1 | | F0FDK9 |
| *Streptococcus sanguinis* SK355 | EGJ38546.1 | | F3US14 |
| *Streptococcus sanguinis* SK408 | EGC24921.1 | | F0FJT3 |
| | EGF08624.1 | | F2BIW4 |
| | EGF19580.1 | | F2CDE0 |
| *Streptococcus sanguinis* SK49 | EGJ38526.1 | | F3UY06 |
| *Streptococcus sanguinis* SK678 | EGC27602.1 | | F0FR11 |
| *Streptococcus sanguinis* SK72 | EGD29398.1 | | F0I1T9 |
| *Streptococcus* sp. SK140 | EIF38589.1 | ZP_10038759.1 | |
| *Streptococcus* sp. SK643 | EIF39120.1 | ZP_10040082.1 | |
| *Streptococcus* sp. C300 | EFX56812.1 | ZP_08050022.1 | E9FHQ0 |
| *Streptococcus* sp. M143 | EFA24288.1 | ZP_06198674.1 | D2EQA3 |
| *Streptococcus* sp. M334 | EFX59032.1 | ZP_08050711.1 | E9FKM3 |
| *Streptococcus* sp. oral taxon 056 str. F0418 | EGP66993.1 | ZP_08662553.1 | F9HGU8 |
| *Streptococcus* sp. oral taxon 058 str. F0407 | EHI77041.1 | ZP_09174472.1 | G6C955 |
| *Streptococcus* sp. oral taxon 071 str. 73H25AP | EFM35756.1 | ZP_07458299.1 | E0Q0E1 |
| *Streptococcus thermophilus* (strain ATCC BAA-491/LMD-9) | ABJ66404.1 | YP_006340266.1 | Q03K68 |
| | AFJ83601.1 | YP_820600.1 | |
| *Streptococcus urinalis* 2285-97 | EHJ57402.1 | ZP_09137413.1 | G5KGX7 |
| *Streptococcus vestibularis* ATCC 49124 | EFQ59772.1 | ZP_07722949.1 | E3CNS3 |
| | EFX96303.1 | ZP_08069523.1 | E8KUL8 |
| *Tannerella forsythia* (strain ATCC 43037/JCM 10827/FDC 338) *Bacteroides forsythus* | AEW20074.1 | YP_005013402.1 | G8UKW3 |
| *Tepidanaerobacter acetatoxydans* (strain DSM21804/JCM 16047/RE1) | AEE92466.1 | YP_004461773.1 | F4LT66 |
| *Thermincola potens* (strain JR) | ADG83236.1 | YP_003641137.1 | D5XAN2 |
| *Thermovirga lienii* (strain ATCC BAA-1197/DSM 17291/Cas60314) | AER67504.1 | YP_004933601.1 | G7V8P3 |
| *Treponema* sp. JC4 | EID85541.1 | ZP_10009441.1 | I0XA75 |
| *Turicibacter sanguinis* PC909 | EFF63439.1 | ZP_06622212.1 | D4W6H2 |
| *Turicibacter* sp. HGF1 | EGC92139.1 | ZP_08167528.1 | F0HEZ8 |
| *Victivallis vadensis* ATCC BAA-548 | EFA99410.1 | ZP_06244492.1 | D1N9V2 |
| *Weeksella virosa* (strain ATCC 43766/DSM 16922/JCM 21250/NBRC 16016/NCTC 11634/CL 345/78) | ADX67941.1 | YP_004238519.1 | F0P329 |
| *Weissella confusa* LBAE C39-2 | CCF29905.1 | ZP_10257557.1 | H1X5Q2 |
| *Weissella paramesenteroides* ATCC 33313 | EER75253.1 | ZP_04782492.1 | C5R921 |
| *Weissella thailandensis* fsh4-2 | CCC57018.1 | | G0UGX7 |
| | Eukaryota | | |
| *Arabidopsis lyrata* subsp. *lyrata* (Lyre-leaved rock-cress) | EFH68720.1 | XP_002892461.1 | D7KIS7 |
| *Arabidopsis lyrata* subsp. *lyrata* (Lyre-leaved rock-cress) | EFH61940.1 | XP_002885681.1 | D7L5U9 |
| *Arabidopsis thaliana* (mouse-ear cress) | CAA85388.1 | | Q42562 |
| *Arabidopsis thaliana* (mouse-ear cress) | CAA85387.1 | | Q42558 |
| *Arabidopsis thaliana* (mouse-ear cress) | AEE76980.1 | NP_189147.1 | Q42561 |
| | BAB02069.1 | | |
| | BAD43868.1 | | |
| | CAA85389.1 | | |
| *Arachis hypogaea* (peanut) | ABO38556.1 | | A9P5P3 |
| | ABO38557.1 | | |
| *Arachis hypogaea* (peanut) | ABO38558.1 | | A9P5P5 |
| *Arachis hypogaea* (peanut) | ABO38554.1 | | A9P5P1 |
| *Arachis hypogaea* (peanut) | ABO38555.1 | | A9P5P2 |
| *Brachypodium sylvaticum* (false brome) | ABL85052.1 | | A1YKG2 |
| *Brassica campestris* (field mustard) | AAC49002.1 | | Q39402 |
| *Brassica juncea* (Indian mustard) (*Sinapis juncea*) | CAC14164.1 | | Q9FT16 |
| *Camellia oleifera* | ACQ57189.1 | | C3W2Q2 |
| *Camellia oleifera* | ACQ57190.1 | | C3W2Q3 |
| *Camellia oleifera* | ACQ63293.1 | | C3W2Q1 |
| *Camellia oleifera* | ACQ57188.1 | | C3W2Q0 |
| *Camellia oleifera* | ACQ57187.1 | | C3W2P9 |
| *Capsicum annuum* (bell pepper) | ADH03021.1 | | D7RU32 |

TABLE 1-continued

| Acyl-ACP TEs | | | |
|---|---|---|---|
| Organism | GenBank ID No. | Ref Seq | Uni Prot |
| *Capsicum chinense* (Scotch bonnet) (bonnet pepper) | AAG35064.1 | | Q9FPM5 |
| *Capsicum frutescens* (cayenne papper) (Tabasco pepper) | AEO12091.1 | | G3F052 |
| *Chimonanthus praecox* | ADM18137.1 | | H9L9E6 |
| *Chlamydomonas reinhardtii* (*Chlamydomonas smithii*) | EDP08596.1 | XP_001696619.1 | A8HY17 |
| *Citrus sinensis* (sweet orange) (*Citrus aurantium* var. *sinensis*) | AEX99667.1 | | H2ESB6 |
| *Coccomyxa subellipsoidea* C-169 | EIE27817.1 | | I0ZAZ8 |
| *Cocos nucifera* (coconut) | AEM72519.1 | | G3ESU6 |
| *Cocos nucifera* (coconut) | AEM72520.1 | | G3ESU7 |
| *Cocous nucifera* (coconut) | AEM72521.1 | | G3ESU8 |
| *Cuphea calophylla* subsp. *mesostemon* | ABB71581.1 | | Q2A1N7 |
| *Cuphea calophylla* subsp. *mesostemon* | ABB71579.1 ABB71580.1 | | Q2Q1N8 |
| *Cuphea hookeriana* (cigar plant) | AAC72882.1 | | Q9ZTF8 |
| *Cuphea hookeriana* (cigar plant) | AAC72881.1 | | Q9ZTF9 |
| *Cuphea hookeriana* (cigar plant) | AAC49269.1 | | Q39514 |
| *Cuphea hookeriana* (cigar plant) | AAC72883.1 | | Q9ZTF7 |
| *Cuphea lanceolata* (cigar flower) | CAA54060.1 | | Q39534 |
| *Cuphea lanceolata* (cigar flower) | CAC19933.1 | | Q9FNS8 |
| *Cuphea lanceolata* (cigar flower) | CAC19934.1 | | Q9FNS7 |
| *Cuphea lanceolata* (cigar flower) | CAB60830.1 | | Q9SMI9 |
| *Cuphea palustris* | AAC49180.1 | | Q39555 |
| *Cuphea palustris* | AAC49179.1 | | Q39554 |
| *Cuphea viscosissima* | AEM72523.1 | | G3ESV0 |
| *Cuphea viscosissima* | AEM72524.1 | | G3ESV1 |
| *Cuphea viscosissima* | AEM72522.1 | | G3ESU9 |
| *Cuphea wrightii* (Wright's waxweed) | AAC49784.1 | | Q39663 |
| *Cuphea wrightii* (Wright's waxweed) | AAC49783.1 | | Q39662 |
| *Garcinia mangostana* | AAB51525.1 | | O04794 |
| *Garcinia mangostana* | AAB51524.1 | | O04793 |
| *Garcinia mangostana* | AAB51523.1 | | O04792 |
| *Glycine max* (soybean) (*Glycine hispida*) | ABD91726.1 | NP_001237802.1 | B1MVG6 |
| *Glycine max* (soybean) (*Glycine hispida*) | ABI20759.1 | | Q0GJK0 |
| *Glycine max* (soybean) (*Glycine hispida*) | ABI20760.1 | | Q0GJJ9 |
| *Haematococcus pluvialis* | AEF13160.1 | | G9B653 |
| *Helianthus annuus* (common sunflower) | CAC80371.1 | | Q8VXJ5 |
| *Helianthus annuus* (common sunflower) | AAB88824.1 AAX19377.1 AAX19378.1 AAX19379.1 AAX19380.1 AAX19381.1 AAX19382.1 AAX19383.1 AAX19384.1 AAX19385.1 AAX19386.1 AAX19387.1 | | O48568 |
| *Helianthus annuus* (common sunflower) | AAQ08202.1 | | Q2UZT2 |
| *Helianthus annuus* (common sunflower) | CAC80370.1 | | Q8VXJ6 |
| *Helianthus annuus* (common sunflower) | AAQ08223.1 AAQ08224.1 AAQ08225.1 AAQ08226.1 | | Q2UZT0 |
| *Helianthus annuus* (common sunflower) | AAL79361.1 | | Q6K1M5 |
| *Helianthus annuus* (common sunflower) | AAX54515.1 | | Q4KU00 |
| *Helianthus annuus* (common sunflower) | AAX54514.1 | | Q4KU01 |
| *Helianthus annuus* (common sunflower) | AAX54516.1 AAX54517.1 AAX54518.1 AAX54519.1 AAX54520.1 AAX54521.1 AAX54522.1 | | Q4KTZ8 |

TABLE 1-continued

Acyl-ACP TEs

| Organism | GenBank ID No. | Ref Seq | Uni Prot |
|---|---|---|---|
| | AAX54523.1 | | |
| | AAX54524.1 | | |
| | AAX54525.1 | | |
| | AAX54526.1 | | |
| | AAX54527.1 | | |
| *Iris germanica* (flag) (fleur-de-lis) | AAG43857.1 | | Q9FQY1 |
| *Iris germanica* (flag) (fleur-de-lis) | AAG43858.1 | | Q9FQY0 |
| *Iris germanica* (flag) (fleur-de-lis) | AAG43859.1 | | Q9FQX9 |
| *Iris tectorum* | AAG43860.1 | | Q9FQX8 |
| *Iris tectorum* | AAG43861.1 | | Q9FQX7 |
| *Iris tectorum* | AAL77443.1 | | Q8S9G4 |
| *Jatropha curcas* | ABX82799.3 | | A9UFC5 |
| *Macadamia tetraphylla* | ADA79524.1 | | D2E6T0 |
| *Macadamia tetraphylla* | ACB29661.1 | | D5FFZ2 |
| *Medicago truncatula* (barrel medic) (*Medicago tribuloides*) | AES91389.1 | XP_003609192.1 | G7JU47 |
| *Myristica fragrans* (nutmeg) | AAB71729.1 | | O24419 |
| *Myristica fragrans* (nutmeg) | AAB71730.1 | | Q6I8R5 |
| *Nicotiana tabacum* (common tobacco) | AFE88232.1 | | H9CCH9 |
| *Perilla frutescens* (beefsteak mint) (*Perilla ocymoides*) | AAL77445.1 | | Q8SMI2 |
| *Populus tomentosa* (Chinese white poplar) | ABC47311.1 | | A1XAM4 |
| *Triticum aestivum* (wheat) | CAD32683.1 | | Q8L6B1 |
| *Ulmus americana* (American elm) | AAB71731.1 | | O24420 |
| *Umbellularia californica* (California bay laurel) (*Tetranthera californica*) | AAC49001.1 | | Q41634 | information obtained from www.enzyme.cbirc.iastate.edu (© Iowa State University of Science and Technology; used with permission)

A method of altering the specificity of a plant acyl-ACP TE for at least one of its substrates is also provided. For example, the specificity of a plant acyl-ACP TE for at least one of its substrates can be increased or decreased, even eliminated. The method comprises introducing into the plant acyl-ACP TE a substrate specificity-altering mutation in the region corresponding to amino acids 118-167, such as from about amino acid 118 to about amino acid 167, of the mature amino acid sequence of the *Cuphea viscosissima* acyl-ACP TE encoded by FatB2 (see, SEQ ID NO:3 in FIG. 1, starting at the amino acid position indicated by ▼). Alternatively, the region can correspond to amino acids 110-184, such as from about amino acid 110 to about amino acid 184, of the mature amino acid of the *Cuphea viscosissima* acyl-ACP TE encoded by FatB2. Also, alternatively, the region can correspond to amino acids 110-205, such as from about amino acid 110 to about amino acid 205, of the mature amino acid of the *Cuphea viscosissima* acyl-ACP TE encoded by FatB2. "Corresponding to" is used herein to refer to an amino acid in an acyl-ACP TE, such as a plant acyl-ACP TE, which, when the amino acid sequence of the acyl-ACP TE is aligned with the mature amino acid sequence of the *Cuphea viscosissima* acyl-ACP TE encoded by FatB2, aligns with the position of the amino acid of the *Cuphea viscosissima* acyl-ACP TE to which reference is made by number. The amino acid in the acyl-ACP TE may or may not have the same numbered position as that in the mature amino acid sequence of the *Cuphea viscosissima* acyl-ACP TE encoded by FatB2. The method can comprise mutating at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. Mutating amino acid 133 to phenylalanine (F) or leucine (L) can increase production of C8 fatty acids, mutating amino acid 133 to valine (V) or alanine (A) can increase production of C14/16 fatty acids, mutating amino acid 142 to A and mutating amino acid 143 to serine (S) can increase production of C8 fatty acids, and mutating both of amino acids 142 and 143 to arginine (R) can increase production of C14/16 fatty acids. The method can further comprise mutating at least one amino acid corresponding to an amino acid selected from the group consisting of amino acid 110 and amino acid 184 of the mature amino acid sequence of the *Cuphea viscosissima* acyl-ACP TE encoded by FatB2. Mutating amino acid 110 to F can increase production of C4/6 fatty acids, mutating amino acid 110 to L can increase production of C8 fatty acids, mutating amino acid 110 to V can increase production of C14/16 fatty acids, and mutating amino acid 184 to F can increase production of C8 fatty acids. The method can further comprise altering the level of activity of the plant acyl-ACP TE by a method comprising mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2. Mutating amino acid 173 to F, mutating amino acid 176 to L, mutating amino acid 205 to F, or a combination of two or more of the foregoing can alter the level of activity of the plant acyl-ACP TE, such as increase the level of activity of the plant acyl-ACP TE. Generally speaking, such mutations alter the level of activity of the plant acyl-ACP TE, such as increase the level of activity of the plant acyl-ACP TE, without altering the substrate specificity significantly, if at all. In other words, these mutations can alter the total amount of fatty acids produced, such as increase the total amount of fatty acids produced, but do not significantly alter (if at all) the mol percentage of each fatty acid. Preferably, even desirably, the level of activity of the plant acyl-ACP TE is increased, rather than decreased.

In view of the foregoing, a method of altering the level of activity of a plant acyl-ACP TE is also provided. For example, the activity level, e.g., thioesterase activity level, such as the total amount of fatty acids produced, of the plant acyl-ACP TE can be increased or decreased compared to the activity level of the corresponding wild-type TE. An alteration in the level of activity can be an increase in fatty acid production or a decrease in fatty acid production, irrespective of whether or not the mol percentage of each fatty acid changes or not. Preferably, even desirably, the level of activity of the plant acyl-ACP TE is increased, rather than decreased. The method comprises mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2. Mutating amino acid 173 to F, mutating amino acid 176 to L, mutating amino acid 205 to F, or a combination of two or more of the foregoing can alter the level of activity of the plant acyl-ACP TE, such as increase the level of activity of the plant acyl-ACP TE. The method can further comprise altering the specificity of the plant acyl-ACP TE by a method comprising introducing into the plant acyl-ACP TE a substrate specificity-altering mutation in the region corresponding to amino acids 118-167 of the mature amino acid sequence of the *Cuphea viscosissima* acyl-ACP TE encoded by FatB2. The method can comprise mutating at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. Mutating amino acid 133 to F or L can increase production of C8 fatty acids, mutating amino acid 133 to V or A can increase production of C14/16 fatty acids, mutating amino acid 142 to A and mutating amino acid 143 to S can increase production of C8 fatty acids, and mutating both of amino acids 142 and 143 to R can increase production of C14/16 fatty acids. The method can further comprise mutating at least one amino acid corresponding to an amino acid selected from the group consisting of amino acid 110 and amino acid 184 of the mature amino acid sequence of the *Cuphea viscosissima* acyl-ACP TE encoded by FatB2. Mutating amino acid 110 to F can increase production of C4/6 fatty acids, mutating amino acid 110 to L can increase production of C8 fatty acids, mutating amino acid 110 to V can increase production of C14/16 fatty acids, and mutating amino acid 184 to F can increase production of C8 fatty acids.

Figure 5:
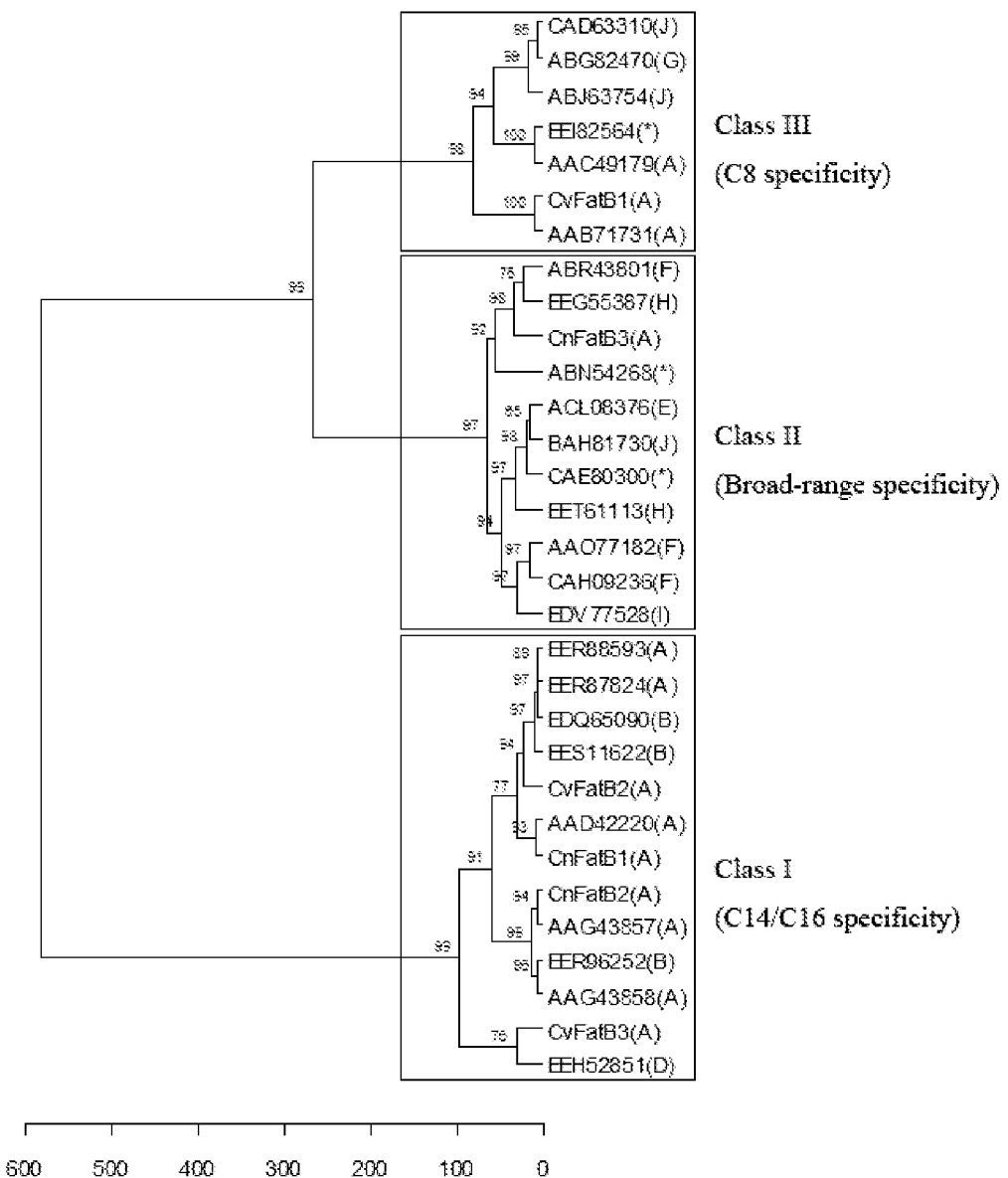
FIG. 5 is a hierarchical clustering dendrogram of acyl-ACP TEs. The acyl-ACP TEs are identified by their GenBank Accessions. Cluster analysis was performed with fatty acid composition data using Euclidean distances and Ward's hierarchical clustering method. The p-values were calculated via multiscale bootstrap resampling with 1,000 replicates. The Subfamily to which each sequence belongs is indicated in parentheses. Non-grouped sequences are indicated by asterisks.

Also in view of the foregoing, an isolated or purified nucleic acid molecule comprising a nucleotide sequence encoding a mutant acyl-ACP TE derived from a wild-type acyl-ACP TE, such as an acyl-ACP TE from FIG. 5, FIG. 9, Table 1, Table 2, or www.enzyme.cbirc.iastate.edu (see, e.g., family TE14; which website is incorporated herein by reference for its teachings regarding acyl-ACP TEs), in particular an acyl-ACP TE from a bacterium, e.g., an acyl-ACP TE from *Bryantella formatexigens*, is also provided. The mutant acyl-ACP TE derived from wild-type *Bryantella formatexigens* acyl-ACP TE comprises two or more amino acid mutations comprising N169Y and S222I, and has increased thioesterase activity compared to wild-type *Bryantella formatexigens* acyl-ACP TE.

Further in view of the foregoing, an isolated or purified nucleic acid molecule comprising a nucleotide sequence encoding a chimeric *Cuphea viscosissima* acyl-ACP TE gene, which comprises a segment of another acyl-ACP TE gene, is provided. Any suitable acyl-ACP TE gene can serve as the source of the segment that is used to replace the segment of the wild-type *Cuphea viscosissima* acyl-ACP TE gene (see, e.g., FIG. 5, FIG. 9, Table 1, Table 2, and www.enzyme.cbirc.iastate.edu (see, e.g., family TE14), which website is hereby incorporated by reference for its teachings regarding acyl-ACP TEs). Preferably, the acyl-ACP TE gene is another *Cuphea viscosissima* acyl-ACP TE gene. The chimeric *Cuphea viscosissima* acyl-ACP TE gene preferably is a chimeric FatB1 gene or a chimeric FatB2 gene. In this regard, preferably the chimeric CvFatB1 gene comprises a segment of the CvFatB2 gene or the chimeric CvFatB2 gene comprises a segment of the CvFatB2 gene.

Still further in view of the foregoing, an isolated or purified nucleic acid molecule comprising a nucleotide sequence encoding a mutant plant acyl-ACP TE, which comprises a substrate specificity-altering mutation in the region corresponding to amino acids 118-167, such as from about amino acid 118 to about amino acid 167, of the mature amino acid sequence of the *Cuphea viscosissima* acyl-ACP TE encoded by FatB2, is provided. Alternatively, the region can correspond to amino acids 110-184, such as from about amino acid 110 to about amino acid 184, of the mature amino acid of the *Cuphea viscosissima* acyl-ACP TE encoded by FatB2. Also, alternatively, the region can correspond to amino acids 110-205, such as from about amino acid 110 to about amino acid 205, of the mature amino acid of the *Cuphea viscosissima* acyl-ACP TE encoded by FatB2. Any suitable plant acyl-ACP TE gene can be mutated (see, e.g., FIG. 5, FIG. 9, Table 1, Table 2, and www.enzyme.cbirc.iastate.edu (see, e.g., family TE14), which website is hereby incorporated by reference for its teachings regarding acyl-ACP TEs). The isolated or purified nucleic acid molecule can be a vector. The encoded mutant plant acyl-ACP TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The encoded mutant plant acyl-ACP TE can further comprise a mutation of at least one amino acid corresponding to an amino acid selected from the group consisting of amino acid 110 and amino acid 184 of the mature amino acid sequence of the *Cuphea viscosissima* acyl-ACP TE encoded by FatB2. The encoded mutant plant acyl-ACP TE can further comprise a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

Still yet another isolated or purified nucleic acid molecule is provided. The isolated or purified nucleic acid molecule comprises a nucleotide sequence encoding a mutant plant acyl-ACP TE, which comprises a level of activity-altering mutation (e.g., a mutation that alters the total amount of fatty acids produced, such as increases the total amount of fatty acids produced) of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2. Any suitable plant acyl-ACP TE gene can be mutated (see, e.g., FIG. 5, FIG. 9, Table 1, Table 2, and www.enzyme.cbirc.iastate.edu (see, e.g., family TE14, which website is hereby incorporated by reference for its teachings regarding acyl-ACP TEs). The isolated or purified nucleic acid molecule can be a vector. The encoded mutant plant acyl-ACP TE can comprise a substrate specificity-altering mutation in the region corresponding to amino acids 118-167, such as from about amino acid 118 to about amino acid 167, of the mature amino acid of the *Cuphea viscosissima* acyl-ACP TE encoded by FatB2. Alternatively, the region can correspond to amino acids 110-184, such as from about amino acid 110 to about amino acid 184, of the mature amino acid of the *Cuphea viscosissima* acyl-ACP TE encoded by FatB2. Also alternatively, the region can correspond to amino acids 110-205, such as from about amino acid 110 to about amino acid 205, of the mature amino acid of the *Cuphea viscosissima* acyl-ACP TE encoded by FatB2. The encoded mutant plant acyl-ACP TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The encoded mutant plant acyl-ACP TE can further comprise a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2.

Mutations, such as substitutions, insertions, deletions, and/or side chain modifications, can be introduced into the nucleotide and amino acid sequences of the acyl-ACP TE using any suitable technique known in the art, including site-directed mutagenesis (Wu, ed., Meth. Enzymol. 217, Academic Press (1993)). Alternatively, domains can be swapped between acyl-ACP TE genes (for example, when creating chimeras). Non-naturally occurring nucleotides and amino acids also can be used. Mutations to the nucleotide sequence should not place the sequence out of reading frame and should not create complementary regions that could produce secondary mRNA structures. The mutant or chimeric acyl-ACP TE may have altered substrate specificity, e.g., reacts with an acyl-ACP substrate that differs in chain length, degree of saturation, or presence/absence of a side group (e.g., methyl group), from that which is acted upon by the wild-type (also referred to as "native") acyl-ACP TE. Alternatively, the mutant or chimeric acyl-ACP TE may have altered relative substrate specificity between two or more substrates, both of which are acted upon by the wild-type acyl-ACP TE. Both types of alterations in substrate specificity are encompassed by references to alterations of substrate specificity and substrate specificity-altering mutations herein. Alternatively or additionally to altered substrate specificity, the mutant or chimeric acyl-ACP TE may have an altered activity level, e.g., level of thioesterase activity, such as the total amount of fatty acids produced, including increased or decreased activity. Altered substrate specificity and altered activity can be detected by expression of the mutant thioesterase in *E. coli*, for example, and assay of enzyme activity.

A nucleotide sequence encoding all or a part of an acyl-ACP TE can be chemically synthesized, such as by the phosphoramidite method (Beaucage et al., Tetrahedron Letters 22: 1859-1869 (1981); and Matthes et al., EMBO J. 3: 801-805 (1984)). Polynucleotides can be synthesized, purified, annealed to their complementary strand, ligated, and then, optionally, cloned into suitable vectors.

The isolated or purified nucleic acid molecule comprising a nucleotide sequence encoding a mutant/chimeric acyl-ACP TE can be a vector. The vector can contain, and preferably does contain, transcription and translation control regions. A promoter can be constitutive or regulatable, such as inducible. Additional sequences that can be present in the vector include pre-processing sequences, such as transit peptide sequences and plastid transit peptide sequences.

The acyl-ACP TEs and mutant/chimeric acyl-ACP TEs identified herein can be used in whole or in part as probes in hybridization assays to identify other TEs that can be used in the methods described herein. The TEs or fragments thereof also can be used as primers to amplify target DNA, such as by polymerase chain reaction (PCR) and other nucleic acid amplification methods. See, e.g., Sambrook et al., Molecular Cloning: A Laboratory Manual, 3$^{rd}$ ed., Cold Spring Harbor Laboratory Press, Cold Spring Harbor, N.Y. (2001); Ausubel et al., eds., Short Protocols in Molecular Biology, 5$^{th}$ ed., John Wiley & Sons (2002).

The nucleic acid molecule comprising a nucleotide sequence encoding an acyl-ACP TE or a mutant/chimeric acyl-ACP TE can be introduced into a host cell or a host organism using any suitable technique as is known in the art. See, e.g., Sambrook et al., Molecular Cloning: A Laboratory Manual, 3$^{rd}$ ed., Cold Spring Harbor Laboratory Press, Cold Spring Harbor, N.Y. (2001); Ausubel et al., eds., Short Protocols in Molecular Biology, 5$^{th}$ ed., John Wiley & Sons (2002). Such methods include microinjection, DNA particle bombardment, electroporation, liposome fusion, *Agrobacterium*-mediated transformation, and methods exemplified herein. Depending on the host cell or the host organism, one method can be preferred over another as readily appreciated by one of ordinary skill in the art. The nucleotide sequence can be codon-optimized for the recipient host cell or organism.

In view of the above, a host cell comprising an above-described isolated or purified nucleic acid molecule is also provided. The host cell or organism can be any suitable host cell or organism. The host cell or organism can be prokaryotic or eukaryotic, unicellular or multicellular, and undifferentiated or differentiated. If large-scale production of short-chain fatty acids is desired, e.g., as a source of biofuel, bacteria (see, e.g., U.S. Pat. App. Pub. No. 2012/0164700, which discloses examples of cyanobacteria, and U.S. Pat. App. Pub. No. 2009/0298143, which discloses methods of expression in bacteria, and both of which are hereby incorporated by reference for their teachings regarding same), yeast (see, e.g., U.S. Pat. App. Pub. No. 2011/0294174, which discloses examples of yeast in Table 26 and other fungi in Table 27 and which is hereby incorporated by reference for its teachings regarding same), and algae (see, e.g., U.S. Pat. App. Pub. No. 2011/0294174, which discloses examples of algae in Table 1 and which is hereby incorporated by reference for its teachings regarding same; also, see U.S. Pat. No. 7,935,515 and U.S. Pat. App. Pub. No. 2012/0164700, which disclose methods of expressing TEs in microalgae and examples of microalgae and which are hereby incorporated by reference for their teachings regarding same; see, also, U.S. Pat. App. Pub. No. 2009/0317878, which is hereby incorporated by reference for its teachings regarding expression of genes in algae) can be preferred. A preferred bacterium is *Escherichia coli*, in particular the strain K27. A preferred yeast is *Saccharomyces cerevisiae*. Alternatively, a crop plant (e.g., maize), such as an oilseed crop plant or a seed cell thereof, can be preferred (see, e.g., U.S. Pat. No. 7,504,563, which discloses expression of a nucleic acid encoding a thioesterase in soybean seed and which is incorporated herein for its teachings regarding same). See, also, U.S. Pat. App. Pub. No. 2010/0154293, which discloses other examples of host cells in paragraph [0080] and which is incorporated herein by reference for its teachings regarding same.

Fatty acids can be harvested, or otherwise collected (e.g., isolation from media containing bacteria that secrete the fatty acids), from host cells or organisms by any convenient method. Cells can be lysed/disrupted (e.g., heat, enzymes, ultrasound, mechanical lysis, osmotic shock, acid/base addition, or infection with a lytic virus), and fatty acids can be separated from cell mass by centrifugation and extraction (e.g., extraction with hydrophobic solvent, liquefaction, supercritical $CO_2$ extraction, or hexane extraction after freeze-drying and pulverization) and further processed/refined as necessary. See, e.g., U.S. Pat. No. 7,935,515 and U.S.

Pat. App. Pub. No. 2012/0135479, which are incorporated specifically by reference for their teachings regarding same.

An isolated or purified mutant acyl-ACP TE derived from a wild-type acyl-ACP TE, such as an acyl-ACP TE from FIG. 5, FIG. 9, Table 1, Table 2, or www.enzyme.cbirc.iastate.edu (see, e.g., family TE14; which website is incorporated by reference herein for its teachings regarding acyl-ACP TEs), in particular an acyl-ACP TE from a bacterium, e.g., an acyl-ACP TE from *Bryantella formatexigens*, is also provided. The mutant acyl-ACP TE derived from wild-type *Bryantella formatexigens* acyl-ACP TE comprises two or more amino acid mutations comprising N169Y and S222I, and has increased thioesterase activity compared to wild-type *Bryantella formatexigens* acyl-ACP TE. Preferably, the mutant acyl-ACP TE derived from wild-type *Bryantella formatexigens* acyl-ACP TE has altered substrate specificity such that it increases production of short-chain fatty acids. Depending on the particular acyl-ACP TE (e.g., an acyl-ACP TE from FIG. 5, FIG. 9, Table 1, Table 2, or www.enzyme.cbirc.iastate.edu (see, e.g., family TE14; which website is incorporated by reference herein for its teachings regarding acyl-ACP TEs), such as acyl-ACP TE from a bacterium) that has been mutated, such mutants can have altered substrate specificity, such as altered substrate specificity that results in increased production of short-chain fatty acids or fatty acids of longer chain length, and/or altered level of activity, e.g., thioesterase activity, such as the total amount of fatty acids produced. Mutants can be derived from wild-type acyl-ACP TEs in accordance with methods known in the art (e.g., site-directed mutagenesis) and exemplified herein. Due to the degeneracy of the genetic code, the same amino acid sequence can be encoded by nucleotide sequences that vary quite a bit.

An isolated or purified chimeric *Cuphea viscosissima* acyl-ACP TE, which comprises a segment of another acyl-ACP TE, is also provided. Any suitable acyl-ACP TE can serve as the source of the segment that is used to replace the segment of the wild-type *Cuphea viscosissima* acyl-ACP TE (see, e.g., an acyl-ACP TE from FIG. 5, FIG. 9, Table 1, Table 2, or www.enzyme.cbirc.iastate.edu (see, e.g., family TE14; which website is incorporated by reference herein for its teachings regarding acyl-ACP TEs). Preferably, the acyl-ACP TE is another *Cuphea viscosissima* acyl-ACP TE. In this regard, the chimera can be made in accordance with methods known in the art, such as at the level of DNA or protein, including synthesis. Preferably, the chimera is a chimera of the TE encoded by a FatB1 gene or a chimera of the TE encoded by a FatB2 gene. In this regard, the chimera can be a chimera of the TE encoded by the CvFatB1 gene comprising a segment of the TE encoded by the CvFatB2 gene or a chimera of the TE encoded by the CvFatB2 gene comprising a segment of the TE encoded by the CvFatB1 gene.

An isolated or purified mutant plant acyl-ACP TE, which comprises a substrate specificity-altering mutation in the region corresponding to amino acids 118-167, such as from about amino acid 110 to about amino acid 167, of the mature amino acid sequence of the *Cuphea viscosissima* acyl-ACP TE encoded by FatB2, is also provided. Alternatively, the region can correspond to amino acids 110-184, such as from about amino acid 110 to about amino acid 184, of the mature amino acid of the *Cuphea viscosissima* acyl-ACP TE encoded by FatB2. Also, alternatively, the region can correspond to amino acids 110-205, such as from about amino acid 110 to about amino acid 205, of the mature amino acid of the *Cuphea viscosissima* acyl-ACP TE encoded by FatB2. The mutant TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The mutant TE can further comprise a mutation of at least one amino acid corresponding to an amino acid selected from the group consisting of amino acid 110 and amino acid 184 of the mature amino acid sequence of the *Cuphea viscosissima* acyl-ACP TE encoded by FatB2. The mutant TE can further comprise a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

Yet another isolated or purified mutant plant acyl-ACP TE is provided. The isolated or purified mutant plant acyl-ACP TE comprises a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2. The mutant TE can further comprise a substrate specificity-altering mutation in the region corresponding to amino acids 118-167, such as from about amino acid 118 to about amino acid 167, of the mature amino acid of the *Cuphea viscosissima* acyl-ACP TE encoded by FatB2. Alternatively, the region can correspond to amino acids 110-184, such as from about amino acid 110 to about amino acid 184, of the mature amino acid of the *Cuphea viscosissima* acyl-ACP TE encoded by FatB2. Also, alternatively, the region can correspond to amino acids 110-205, such as from about amino acid 110 to about amino acid 205, of the mature amino acid of the *Cuphea viscosissima* acyl-ACP TE encoded by FatB2. The mutant TE can comprise a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2. The mutant TE can further comprise a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2.

Once sequenced, polypeptides can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963), and Stewart and Young in *Solid Phase Peptide Syntheses* (2nd Ed., Pierce Chemical Company, 1984). Automated peptide synthesizers are commercially available, as are services that make peptides to order.

EXAMPLES

The following examples serve to illustrate the present disclosure. The examples are not intended to limit the scope of the claimed invention in any way.

Example 1

This example describes the functional characterization of diverse acyl-ACP TEs rationally chosen based on phylogenetic classification of the TEs.

Sequences from Family TE14 (Cantu et al. (2010), supra) in the ThYme database (www.enzyme.cbirc.iastate.edu) were downloaded from the GenBank (Benson et al., Nucleic Acids Res. 39 (suppl. 1): D32-D37 (2011)) and UniProt (UniProt Consortium: The universal protein resource (UniProt) in 2010, Nucleic Acids Res. 38: D142-D148 (2010)) databases. Fragments and incomplete sequences were removed, yielding 360 acyl-ACP TE sequences. A multiple sequence alignment (MSA) was generated from catalytic domains of these sequences using MUSCLE 3.6 (Edgar, Nucleic Acids Res. 32: 1792-1797 (2004)) with default parameters. An unrooted phylogenetic tree based on the MSA was built using Molecular Evolutionary Genetics Analysis 4 (MEGA4) (Tamura et al., Mol. Biol. Evol. 24: 1596-1599 (2007)).

The minimum evolution algorithm was used due to its high effectiveness with large data sets (Desper et al., J. Comput. Biol. 9: 687-705 (2002)), gaps were subjected to pairwise deletion, and an amino acid Jones-Taylor-Thornton (JTT) (Jones et al., Comput. Appl. Biosci. 8: 275-282 (1992)) distance model was chosen. The phylogenetic tree was further verified by a bootstrap test with 1,000 replicates. The bootstrapped consensus tree was qualitatively analyzed and broken into apparent subfamilies. Statistical analysis was conducted to show that all sequences within a subfamily were more closely related to each other than to sequences in other subfamilies. Based on the MSA, JTT distances between all sequences were calculated and arranged into a j×j matrix, where j is the total number of sequences. Inter-subfamily distances and variances were determined using this matrix. For each apparent subfamily, a smaller k×k matrix, where k is the number of sequences in a given subfamily, was calculated. From this, intra-subfamily mean distances and variances were determined. These values were applied to the following equation to determine z:

$$z = \frac{\bar{x}_{ij} - (\bar{x}_{ii} + \bar{x}_{jj})/2}{\sqrt{\frac{\sigma_i^2}{n_{ij}} + \frac{\sigma_{ii}^2}{n_i} + \frac{\sigma_{jj}^2}{n_j}}}$$

where $\bar{x}_{ij}$, $\bar{x}_{ii}$, and $\bar{x}_{jj}$ are the inter- and intra-subfamily mean JTT distances, $n_{ij}$, $n_{ii}$, and $n_{jj}$ are the total number of taxa used for each $\bar{x}$ value, and $\sigma_i^2$, $\sigma_{ii}^2$, and $\sigma_{jj}^2$ are the pooled inter- and intra-subfamily variances (Mertz et al., Biopolymers 79: 197-206 (2005)).

A z-value >3.3 between two subfamilies shows that the difference between them is statistically significant to p<0.001. If a z-value between two apparent subfamilies were <3.3, alternative apparent subfamilies were chosen and/or individual sequences were removed, and the statistical calculations were repeated. Subfamilies were finally defined with a phylogenetic tree in which all z-values exceeded 3.3, sometimes leaving some sequences outside any subfamily (i.e. non-grouped sequences) (see Table 2).

TABLE 2

Total activity of synthesized and cloned acyl-ACP TEs

| Subfamily | ACC No. or Name | Organism | Rationale for synthesis[a] | Total Fatty Acids (nmol/mL)[b] |
|---|---|---|---|---|
| | | Kingdom: Planta | | |
| A | AAC49179[c,d] | Cuphea palustris | A (Bimodal specificity for C8 and C10 substrates) Dehesh et al., Plant Physiol. 110: 203-210 (1996) | 708 ± 45 |
| | AAB71731 | Ulmus Americana | A (Broad specificity; highest activity on C10 and C16) Voelker et al., Plant Physiol. 114: 669-677 (1997) | 1098 ± 62 |
| | AAG43857 | Iris germanica | B | 261 ± 20 |
| | AAG43858 | Iris germanica | B | 14.8 ± 4.6 |
| | EER87824 | Sorghum bicolor | B (Member of a Subfamily A Poeceae TE cluster) | 126 ± 13 |
| | EER88593 | Sorghum bicolor | B (Member of a Subfamily A Poeceae TE cluster) | 90.7 ± 8.0 |
| | CnFatB1 | Cocos nucifera | C | 130 ± 12 |
| | CnFatB2 | Cocos nucifera | C | 572 ± 32 |
| | CnFatB3 | Cocos nucifera | C | 200 ± 11 |
| | CvFatB1 | Cuphea viscosissima | C | 79.2 ± 9.7 |
| | CvFatB2 | Cuphea viscosissima | C | 249 ± 9 |
| | CvFatB3 | Cuphea viscosissima | C | 18.9 ± 2.1 |
| | AAD42220 | Elaeis guineensis | C | 36.7 ± 3.8 |
| B | EDQ65090 | Physcomitrella patens | B (Member of novel plant subfamily) | 380 ± 29 |
| | EER96252 | Sorghum bicolor | B (Member of novel plant subfamily) | 175 ± 11 |
| | EES11622 | Sorghum bicolor | B (Member of novel plant subfamily) | 9.43 ± 2.03 |
| D | EEH52851 | Micromonas pusilla | B | 16.3 ± 1.6 |
| | | Kingdom: Bacteria | | |
| E | ACL08376 | Desulfovibrio vulgaris | D (Medium-chain linear, branched, and hydroxy fatty acids) Ratledge et al., Microbial Lipids, Vol. 1, Academic Press, San Diego, CA (1988) | 330 ± 9 |
| F | CAH09236 | Bacteroides fragilis | D (Hydroxy fatty acids) Ratledge et al., Microbial Lipids, Vol. 1, Academic Press, San Diego, CA (1988) | 215 ± 6 |

TABLE 2-continued

Total activity of synthesized and cloned acyl-ACP TEs

| Subfamily | ACC No. or Name | Organism | Rationale for synthesis[a] | Total Fatty Acids (nmol/mL)[b] |
|---|---|---|---|---|
| | ABR43801 | Parabacteroides distasonis | D (Branched and branched hydroxy fatty acids) Sakamoto et al., Int. J. Syst. Evol. Microbiol. 57: 293-296 (2007) | 70.3 ± 4.4 |
| | AAO77182[e] | Bacteroides thetaiotaomicron | D (Anteiso-branched and hydroxy fatty acids) Ratledge et al., Microbial Lipids, Vol. 1, Academic Press, San Diego, CA (1988) | 60.4 ± 2.9 |
| G | ABG82470 | Clostridium perfringens | D (Medium-chain fatty acids) Moss et al., Appl. Microbiol. 15: 390-397 (1967) | 72.0 ± 9.5 |
| H | EEG55387 | Clostridium asparagiforme | B | 25.9 ± 4.2 |
| | EET61113 | Bryantella formatexigens | B | 381 ± 3 |
| I | EDV77528 | Geobacillus sp. | D (Iso-branched fatty acids) Rahman et al., BMC Microbiol. 2007: 7 (2007) | 64.9 ± 12.0 |
| J | BAH81730 | Streptococcus dysgalactiae | D (Medium-chain and cyclic propane ring fatty acids) Ratledge et al., Microbial Lipids, Vol. 1, Academic Press, San Diego, CA (1988) | 623 ± 14 |
| | ABJ63754 | Lactobacillus brevis | D (Medium-chain and cyclic propane ring fatty acids) Johnsson et al., Appl. Environ. Microb. 61: 4497-4499 (1995) | 710 ± 10 |
| | CAD63310[e] | Lactobacillus plantarum | D (Medium-chain 3'-hydroxy fatty acids) Johnsson et al., Appl. Environ. Microb. 61: 4497-4499 (1995); Sjogren et al., Appl. Environ. Microb. 69: 7554-7557 (2003) | 436 ± 10 |
| Non-grouped | EEI82564 | Anaerococcus tetradius | D (Organism produces butyric acid) Murdoch et al., J. Med. Microbiol. 34: 295-308 (1991) | 1381 ± 146 |
| | CAE80300 | Bdellovibrio bacteriovorus | D (Straight-chain odd-numbered fatty acids) Ratledge et al., Microbial Lipids, Vol. 1, Academic Press, San Diego, CA (1988) | 333 ± 18 |
| | ABN54268 | Clostridium thermocellum | D (Branched-chain fatty acids) Ratledge et al., Microbial Lipids, Vol. 1, Academic Press, San Diego, CA (1988) | 97.7 ± 3.2 |

[a]A: Functionally characterized TEs; B: TE does not group near characterized TEs and/or no organism lipid profile information is available; C: TEs cloned from organisms known to produce MCFAs; D: Organism's lipid profile used and predominant fatty acid constituents identified in the organism are listed in parentheses.
[b]The data are represented as mean ± standard error (n = 4).
[c]All but the three C. nucifera sequences were codon-optimized for expression in E. coli.
[d]Transit peptides were removed from all plant sequences.
[e]Acyl-ACP TEs with known crystal structures.
TEs were expressed in E. coli K27, and free fatty acids (FAs) that accumulated in the medium were analyzed by GC-MS.

All sequences within individual subfamilies were aligned using MUSCLE 3.6, and rooted phylogenetic trees were built in MEGA4 with the same tree and bootstrap parameters as described above. A few sequences from another subfamily (that with the highest z-value) were chosen to root individual subfamily trees.

A total of 360 amino acid sequences belonging to Family TE14 (Cantu et al. (2010), supra) were subjected to phylogenetic analysis and grouped into subfamilies. A subfamily is defined as having at least five sequences from different species, and it must pass the statistical tests described in the experimental procedures. Ten subfamilies met these criteria, accounting for 326 TE sequences; in addition 34 TE sequences could not be grouped into any of these subfamilies. All z-values were >3.4, ranging from 3.41 to 29.7, and mean distances between different subfamilies were larger than those within subfamilies.

Family TE14 contains acyl-ACP TEs that had previously been characterized from plants and classified into two types, FatA and FatB (Jones et al. (1995), supra). Of the ten subfamilies identified, Subfamilies A, B, and C are comprised of acyl-ACP TEs found in plants. All experimentally characterized sequences previously classified as FatB acyl-ACP TEs make up ~25% of Subfamily A, which contains 81 angiosperm-sourced sequences. The coconut and C. viscosissima acyl-ACP TEs identified also belong to this subfamily. Subfamily B, which comprises 21 sequences primarily sourced from angiosperms as well as from the moss Physcomitrella patens, represents a potentially novel plant acyl-ACP TE subfamily with no previous experimental or phylogenetic characterization. Plant FatA acyl-ACP TEs, which act on long-chain acyl-ACP molecules, especially oleoyl-ACP (Jones et al. (1995), supra), belong to the 32-member Subfamily C. As with Subfamily B, the six green algal sequences from Chlamydomonas, Ostreococcus, and Micromonas that comprise Subfamily D have not been experimentally characterized.

Unlike several plant acyl-ACP TEs, no bacterial acyl-ACP TEs had been previously functionally characterized. A total of 186 bacterial acyl-ACP TE sequences were classified into six subfamilies (Subfamily E-Subfamily J). All 17 acyl-ACP TE sequences from gram-negative bacteria are in Subfamily E, which includes sequences from halophilic (*Salinibacter* and *Rhodothermus*), sulfate-reducing (*Desulfovibrio, Desulfohalobium,* and *Desulfonatronospira*), chemo-organotrophic (*Spirosoma*), metal-reducing (*Anaeromyxobacter, Geobacter,* and *Pelobacter*), and marine (*Microscilla*) bacteria. Subfamily F consists of 24 sequences, mainly from *Bacteroides* but also from other related bacteria. Protein Data Bank (PDB) structure 2ESS, obtained from a structural genomic effort, is part of this subfamily. Subfamily G and Subfamily H have 31 and 27 sequences, respectively, primarily from *Clostridium*. Subfamily I is comprised of eight sequences from six genera. Gram-positive lactic acid bacteria, almost completely from the genera *Lactobacillus, Enterococcus,* and *Streptococcus*, are part of Subfamily J (79 sequences). PDB:2OWN, the second bacterial acyl-ACP TE structure obtained from a structural genomic effort, appears in this family. Although the two known Family TE14 crystal structures (PDB:2ESS in Subfamily F and PDB:2OWN in Subfamily J) are from organisms in widely separated subfamilies, they are highly similar, as may be expected since they are members of the same enzyme family.

Some Family TE14 sequences are not grouped into any subfamily because their inclusion decreased z-values below acceptable limits. These include two plant and four moss sequences adjacent to Subfamilies A and C, and 28 bacterial sequences more closely related to Subfamilies E to I. No experimental work had previously been done on any of these sequences.

Upon generating the phylogenetic relationships among the 360 acyl-ACP TE sequences predicted or experimentally placed in Family TE14, 25 were chosen for experimental characterization. Of these, the cDNA for 24 was synthesized, while the cDNA of the *Elaeis guineensis* (oil palm) acyl-ACP TE was isolated from a phage cDNA library previously constructed from mRNA isolated from the developing fruit of Indonesian-sourced oil palm.

The selection of acyl-ACP TEs to characterize was based upon the primary structure-based phylogenetic relationships among the enzymes, along with knowledge of the fatty acid profile of the source organisms of these acyl-ACP TEs. Briefly, at least one TE was characterized from each of the ten subfamilies except for Subfamily C, whose members appear to be specific for oleoyl-ACP substrates. For subfamilies that contain acyl-ACP TEs originating from organisms without any known fatty acid data, or from organisms where acyl-ACP TEs were not previously characterized, acyl-ACP TE sequences that are evolutionarily distant from each other within each subfamily were selected for further investigation. For example, within Subfamily A there are two distinct and separate groupings of acyl-ACP TEs that are derived from the Poaceae family, for which there is no functional characterization (see Table 2). One grouping contains one sorghum acyl-ACP TE sequence (GenBank:EER87824) and the other contains two (GenBank:EER88593 and GenBank:EES04698). To explore this structural divergence as an indicator of potential functional divergence in substrate specificities, one each of these Subfamily A sorghum acyl-ACP TEs (GenBank: EER87824 and GenBank:EER88593) and the two Subfamily B sorghum acyl-ACP TEs were expressed and functionally characterized.

Example 2

This example describes the cloning of acyl-ACP TEs from *Cocus nucifera* (coconut) and *Cuphea viscosissima*.

Coconut fruits of different developmental stages were obtained from the USDA-ARS-SHRS National Germplasm Repository (Miami, Fla., USA). Seeds of *C. viscosissima* were obtained from the North Central Regional Plant Introduction Station (NCRPIS, Ames, Iowa, USA). They were treated overnight with 0.1 mM gibberellic acid and then germinated in a growth chamber (Environmental Growth Chambers, Chagrin Falls, Ohio) with 12 hours of illumination at 25° C. followed by 12 hours of darkness at 15° C. Seedlings were transplanted into soil and cultivated at NCRPIS. Seeds at different developmental stages were collected and flash-frozen in liquid nitrogen.

Acyl-ACP TE cDNAs were cloned from *C. viscosissima* and coconut via a homologous cloning strategy. MSAs of plant TE14 sequences revealed two conserved regions (RYPTWGD [SEQ ID NO: 7] and NQHVNNVK [SEQ ID NO: 8]), from which two degenerate primers, DP-F3 (5'-AGNTAYCCNACNTGGGGNGA-3' [SEQ ID NO: 9]) and DP-R3 (5'-TACTTNACRTTRTTNACRTGYTGRTT-3' [SEQ ID NO: 10]), were designed. RNA was extracted from endosperm of nearly mature coconuts and immature seeds of *C. viscosissima* using the total RNA (plant) kit (IBI Scientific, Peosta, Iowa, USA). RNA was reverse-transcribed to cDNA using the SuperScript™ first-strand synthesis system for RT-PCR kit (Invitrogen, Carlsberg, Calif., USA). PCR was performed in a 50-μL reaction mixture containing 20 ng cDNA, 1×Pfx buffer, 1 mM MgSO$_4$, 0.3 mM dNTP, 5.12 μM DP-F3 and DP-R3 primers, and 0.5 U Pfx polymerase (Invitrogen) using a cycling program of 94° C. for four minutes, 35 cycles of 94° C. for 30 seconds, 52° C. for 30 seconds and 72° C. for 45 seconds, and a final extension step of 72° C. for five minutes. The expected ~350-bp products were identified by agarose gel electrophoresis, and their DNA bands were recovered using the QiaQuick gel extraction kit (Qiagen, Valencia, Calif., USA) and cloned into the pENTR TOPO TA vector (Invitrogen). Using primers designed from the sequences of the cloned 350-bp fragments, the 5'- and 3'-ends of the cDNAs were obtained using the SMARTer RACE (rapid amplification of the cDNA ends) cDNA amplification kit (Takara Bio, Otsu, Japan).

For each acyl-ACP TE sequence, the full-length cDNA, minus the N-terminal chloroplast transit peptide, was amplified by PCR with primers engineered to introduce Bam HI and Eco RI restriction sites at the 5'- and 3'-ends, respectively. The PCR-amplified products were digested with Bam HI and Eco RI and cloned into the corresponding restriction sites of the pUC57 vector, which placed the acyl-ACP TE sequence under the transcriptional control of the lacZ promoter. The sequence of each construct was confirmed by sequencing both strands. Confirmed expression vectors of coconut genes were transformed into *E. coli* strain K27, while sequences of *C. viscosissima* acyl-ACP TEs were synthesized after being codon-optimized for expression in *E. coli* using the OptimumGene codon optimization program provided by GenScript USA (Piscataway, N.J., USA).

MCFAs are abundant in the oil produced in fruits of coconut (i.e., predominantly C12 and C14 and a small amount (0.2-1%) of C6 fatty acids (Kumar et al., J. Food Qual. 32: 158-176 (2009); Kumar et al., Indian Coconut J. 37: 4-14 (2006); and Kumar et al., Trop. Agr. 81: 34-40 (2004)) and seeds of *C. viscosissima* (i.e., predominantly C8 and C10 fatty acids (Phippen et al., Ind. Crop Prod. 24: 52-59 (2006)). Therefore, acyl-ACP TEs in the seeds of these species are predicted to be specific for medium-chain acyl-ACPs. Acyl-ACP TE sequences were isolated from coconut and *C. viscosissima* by a homologous cloning strategy. Using degenerate primers, which were designed from conserved regions of plant TE14 family enzymes, a 350-bp fragment in the middle of the mRNAs was amplified from cDNA generated from both developing coconut endosperm and *C. viscosissima* seeds. Sequencing of cloned PCR products identified three new acyl-ACP TE sequences each from coconut and *C. viscosissima*. The full-length cDNA sequences were obtained by RACE for three acyl-ACP TEs [CnFatB1 (JF338903), CnFatB2 (JF338904), and CnFatB3 (JF338905)] from coconut and three [CvFatB1 (JF338906), CvFatB2 (JF338907), and CvFatB3 (JF338908)] from *C. viscosissima*.

The predicted open reading frames of coconut and *C. viscosissima* acyl-ACP TE cDNAs were identified. They encode pre-proteins of 412 to 423 amino acids, with calculated molecular weights of 45.8 to 46.5 kDa and theoretical pIs of 6.4 to 8.8. Plant acyl-ACP TEs are nuclear-encoded, plastid-targeted proteins with an N-terminal plastid-targeting peptide extension (Voelker et al. (1992), supra). For each of the cloned coconut and *C. viscosissima* acyl-ACP TEs, the putative plastid-targeting peptide cleavage site was located on the N-terminal side of the conserved sequence LPDW, as proposed for many other plant acyl-ACP TEs (Jones et al. (1995), supra; Sanchez-Garcia (2010), supra; Dormann et al. (1995), supra; Jha et al., Plant Physiol. Biochem. 44: 645-655 (2006); and Moreno-Perez et al., Plant Physiol. Biochem. 49: 82-87 (2011)). These yield predicted mature proteins of 323 to 331 amino acid residues (Huynh et al., Plant Physiol. Biochem. 40:1-9 (2002)), with calculated molecular weights of 36.6 to 37.5 kDa and theoretical pIs of 5.4 to 7.3. Alignment of the deduced amino acid sequences of coconut and *C. viscosissima* acyl-ACP TE cDNAs showed that, except for the plastid-targeting peptide sequences and very near the C-terminus, the sequences are co-linear and share very high identity (63-86%) within a species. These sequences cluster within Subfamily A.

Example 3

This example describes in vivo activity assays.

*E. coli* strain K27 contains a mutation in the fadD gene impairing 13-oxidation of fatty acids, which results in the accumulation of free fatty acids in the growth medium (Klein et al., Eur. J. Biochem. 19: 442-450 (1971); and Overath et al., Eur. J. Biochem. 7: 559-574 (1969)). Each TE was expressed in *E. coli* K27, and free fatty acids that accumulated in the medium were extracted and analyzed. Four colonies for each construct were independently cultured in 2 mL LB medium supplemented with 100 mg/L carbicillin in 17-mL culture tubes. When the culture reached an $OD_{600}$ of ~0.7, the growth medium was replaced with 3 mL of M9 minimal medium (47.7 mM $Na_2HPO_4$, 22.1 mM $KH_2PO_4$, 8.6 mM NaCl, 18.7 mM $NH_4Cl$, 2 mM $MgSO_4$, and 0.1 mM $CaCl_2$) supplemented with 0.4% glucose and 100 mg/l carbicillin, and 10 µM isopropyl-β-D-thiogalactopyranoside (IPTG) was added to induce acyl-ACP TE expression. After 40 hours of cultivation, cells were pelleted, and free fatty acids in the supernatant were extracted essentially following a previously described method (Voelker et al., J. Bacteriol. 176: 7320-7327 (1994); and Mayer et al., BMC Plant Biol. 2007: 7 (2007)). Briefly, 2 mL of culture supernatant was supplemented with 10 µg heptanoic acid (7:0), 10 µg undecanoic acid (11:0), and 20 µg heptadecanoic acid (17:0) (Sigma-Aldrich, St. Louis, Mo., USA) as internal standards. The mixture was acidified with 20 µL of 1 M HCl, and 4 mL chloroform-methanol (1:1 vol/vol) was used to recover the fatty acids from the medium. After vortexing for 10 minutes and centrifuging at 1000×g for four minutes, the lower chloroform phase was transferred to a new tube and evaporated under a stream of $N_2$ gas until the samples were concentrated to ~300 µL. Samples (1 µL) were analyzed on an Agilent Technologies (Santa Clara, Calif., USA) 6890 Series gas chromatograph (GC) system used with an Agilent 5973 mass selective detector equipped with an Agilent CP-Wax 58 FFAP CB column (25 mm×0.15 mm×0.39 mm). The GC program followed an initial temperature of 70° C. for two minutes, ramped to 150° C. at 10° C./minute and held for three minutes, ramped to 260° C. at 10° C./minute, and held for 14 minutes. Final quantification analysis was performed with AMDIS software (National Institute of Standards and Technology). Determination of C4 to C8, C10 to C12, and >C12 fatty acid concentrations was based on the fatty acid internal standards 7:0, 11:0, and 17:0, respectively. The total concentration of fatty acids produced by each acyl-ACP TE was obtained by subtracting the concentration of fatty acid produced by *E. coli* expressing a control plasmid (pUC57) lacking a TE from that produced by *E. coli* expressing a given acyl-ACP TE sequence from the same vector. The three most abundant fatty acids produced by the control strain were 8:0 (2.0 nmol/ml), 14:0 (3.5 nmol/ml), and 16:0 (3.1 nmol/ml), and their levels were minimal compared to strains expressing acyl-ACP TEs. Compared to GC analyses of fatty acids after derivatization (e.g., methylation or butylation), the GC-MS method used non-derivatized free fatty acids, which is better optimized for analyzing short-chain fatty acids (e.g., 4:0, 6:0, 8:0, 10:0, 12:0, and 14:0). However, this method may be less sensitive for longer-chain fatty acids (e.g., 18:0 and 18:1).

Analysis of free fatty acids revealed possible peaks characteristic of 2-tridecanone. To further confirm this identification, retention times and MS spectra of the peaks in each sample were compared to a 2-tridecanone standard (Sigma-Aldrich).

All isolated acyl-ACP TE cDNAs were expressed in *E. coli* strain K27. Secreted fatty acids were analyzed with GC-MS, and the total fatty acid yield in the medium was used to represent the in vivo activities of these enzymes on acyl-ACPs, though it remains possible that some of these enzymes might also hydrolyze acyl-CoAs (Othman et al., Biochem. Soc. Trans. 28: 619-622 (2000)).

A total of 13 acyl-ACP TEs from Subfamily A were characterized, including single acyl-ACP TEs from *Cuphea palustris* (GenBank:AAC49179), *U. americana* (GenBank: AAB71731), and oil palm (*E. guineensis*, GenBank: AAD42220), two each from *Iris germanica* (GenBank: AAG43857 and GenBank:AAG43858) and *Sorghum bicolor* (GenBank:EER87824 and GenBank:EER88593), and three each from coconut and *C. viscosissima*. Total fatty acid concentrations produced by these acyl-ACP TEs are listed in Table 1, and the resulting fatty acid compositions are shown in FIG. 2. Acyl-ACP TEs from *C. palustris* and *U. americana*, which have previously been functionally characterized in vitro (Dehesh et al. (1996), supra; and Voelker et al. (1997), supra), were studied as controls.

*C. palustris* acyl-ACP TE produced 97 mol % 8:0 and only 0.8 mol % 10:0 fatty acids (FIG. 2A), while *U. americana* acyl-ACP TE made 44 mol % 8:0 and 23 mol % 10:0 fatty acids (FIG. 2B). *E. guineensis* acyl-ACP TE produced mainly 14:0 (47 mol %) and 16:1 (26 mol %) fatty acids (FIG. 2C). The acyl-ACP TEs from *I. germanica* and *S. bicolor* have similar substrate specificities, producing mainly 14:0 (30-46 mol %), 16:0 (11-23 mol %), and 16:1 (31-44 mol %) fatty acids (FIG. 2B). CnFatB1 (JF338903) and CnFatB2 (JF338904) made predominantly 14:0 (36-44 mol %) and 16:1 (31-44 mol %) fatty acids, whereas CnFatB3 (JF338905) made mainly 12:0 (34 mol %) and 14:1 (22 mol %) fatty acids (FIG. 2C). Finally, CvFatB1 (JF338906) produced mainly 8:0

(51 mol %) and 10:0 (25 mol %), and CvFatB2 (JF338907) made mainly 14:0 (46 mol %), 16:0 (25 mol %) and 16:1 (20 mol %) fatty acids (FIG. 2A). In contrast, CvFatB3 (JF338908) has narrower substrate specificity, producing predominantly 14:0 fatty acid (84 mol %).

The CvFatB1 and CvFatB3 TEs, for which corresponding cDNAs were isolated from the developing seeds of *C. viscosissima* produced MCFAs in *E. coli*, and CvFatB1 shows substrate specificity consistent with the fatty acid constituents present in the seed oil. The relative distributions of 8:0 and 10:0 fatty acids differ; CvFatB1 produced twice as much 8:0 compared to 10:0 fatty acid, whereas there is ~fourfold more 10:0 fatty acid within *C. viscosissima* seed oil (Phippen et al., Ind. Crop Prod. 24: 52-59 (2006)).

Three acyl-ACP TEs from plant sources belonging to Subfamily B, including those from *P. patens* (GenBank: EDQ65090) and *S. bicolor* (GenBank:EER96252 and GenBank:EES11622), and one acyl-ACP TE from Subfamily D sourced from the alga *Micromonas pusilla* (GenBank: EEH52851), were similarly characterized. Total activity in *E. coli* expressing these acyl-ACP TEs varied from 9 to 380 nmol/mL (Table 1). These four acyl-ACP TEs showed similar substrate specificities, producing predominantly 14:0 (34-65 mol %) and 16:1 (23-37 mol %) fatty acids (FIG. 2D).

Figure 3:
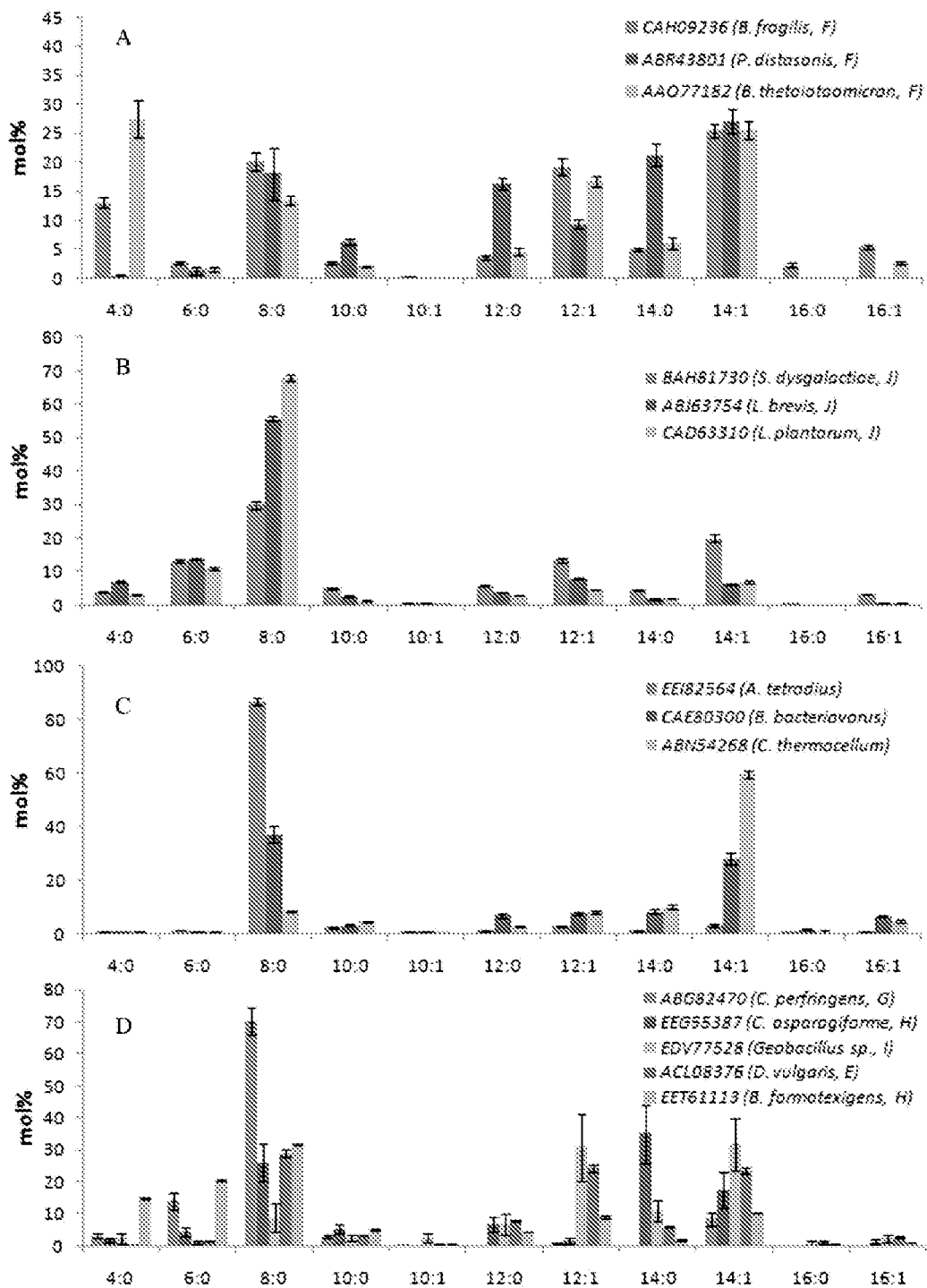
FIG. 3a is a bar graph showing the fatty acid composition of *E. coli* K27 cultures expressing acyl-ACP TEs from *B. fragilis, P. distasonis*, or *B. thetaiotaomicron* (Subfamily F). In parentheses are the organism and the subfamily to which each sequence belongs. Error bars represent standard errors.
FIG. 3b is a bar graph showing the fatty acid composition of *E. coli* K27 cultures expressing acyl-ACP TEs from *S. dysgalactiae, L. brevis*, or *L. plantarum* (Subfamily J). In parentheses are the organism and the subfamily to which each sequence belongs. Error bars represent standard errors.
FIG. 3c is a bar graph showing the fatty acid composition of *E. coli* K27 cultures expressing acyl-ACP TEs from *A. tetradius, B. Bacteriovorus*, or *C. thermocellum* (non-grouped). In parentheses is the organism for each sequence. Error bars represent standard errors.
FIG. 3d is a bar graph showing the fatty acid composition of an *E. coli* K27 culture expressing *C. perfringens* (Subfamily G), *C. asparagiforme* (Subfamily H), *Geobacillus* sp. (Subfamily I), *D. vulgaris* (Subfamily E), or *B. formatexigens* (Subfamily H). In parentheses are the organism and the subfamily to which each sequence belongs. Error bars represent standard errors.

Eleven acyl-ACP TE sequences from Subfamilies E to J sourced from bacteria and three bacterial sequences that were not placed in any subfamily were characterized (Table 1 and FIG. 3). Based on their substrate specificities, these acyl-ACP TEs were classified into two groups. One group produced primarily SCFAs and MCFAs (>75 mol % 4:0 to 8:0 fatty acids). This group included acyl-ACP TEs from *Anaerococcus tetradius* (GenBank:EEI82564, no subfamily, 87% 8:0), *Clostridium perfringens* (GenBank:ABG82470, Subfamily G, 14% 6:0 and 70% 8:0), *Lactobacillus brevis* (GenBank: ABJ63754, Subfamily J, 7% 4:0, 14% 6:0, and 55% 8:0), and *Lactobacillus plantarum* (GenBank:CAD63310, Subfamily J, 11% 6:0 and 68% 8:0) (FIG. 3). The other group showed broad- and binary-range substrate specificities. The binary-range activities were centered on C8 and C12/C14 substrates (FIG. 3).

Figure 4:
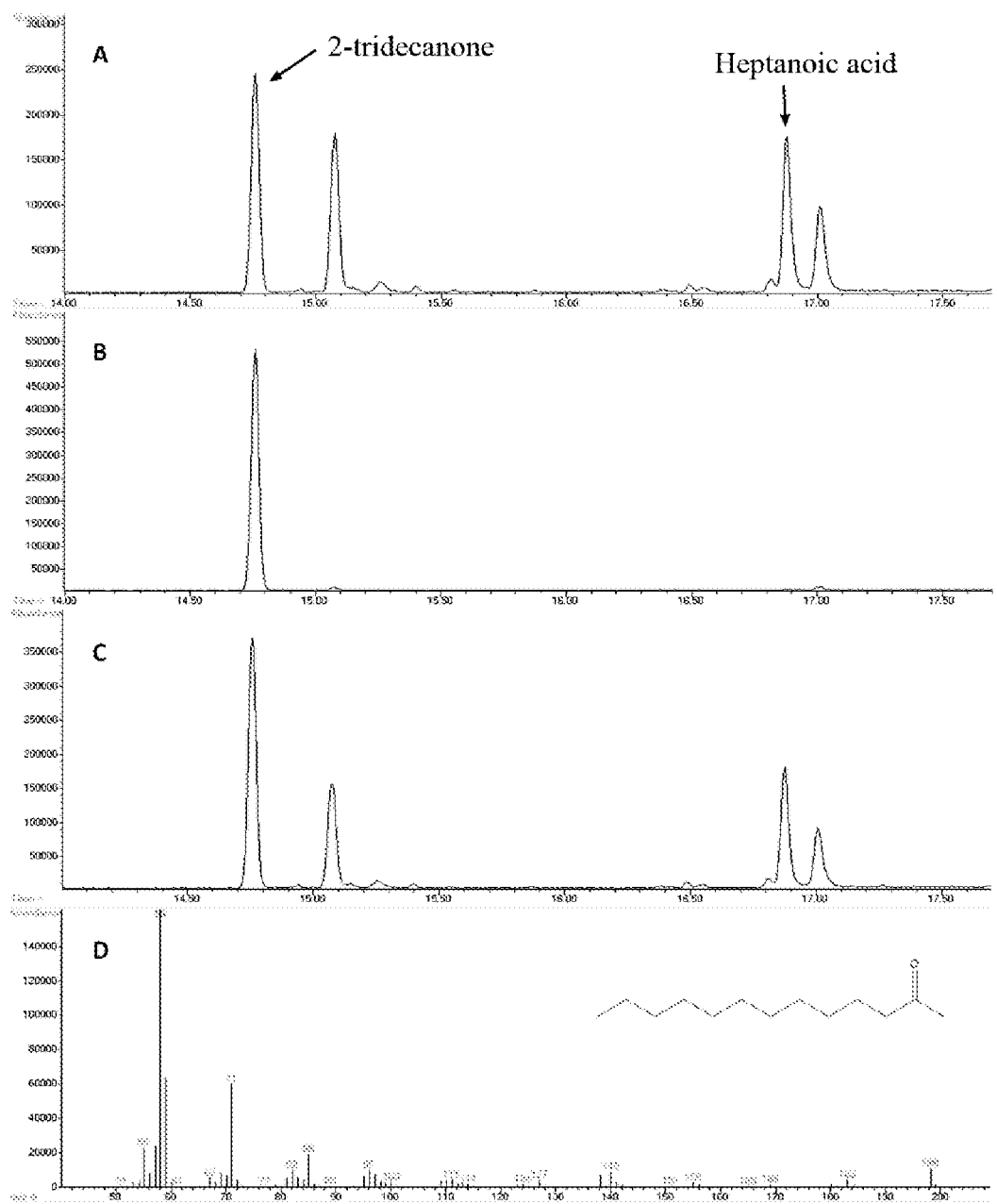
FIG. 4a is a gas chromatogram of an extract from *E. coli* K27 culture expressing a bacterial TE (*Bdellovibrio bacteriovorus*, GenBank:CAE80300).
FIG. 4b is a gas chromatogram of the 2-tridecanone standard.
FIG. 4c is a gas chromatogram of a mixture of the extract of FIG. 4a and the standard of FIG. 4b.
FIG. 4d is a mass spectrum of 2-tridecanone.

Interestingly, many bacterial acyl-ACP TEs, such as those from *Desulfovibrio vulgaris* (GenBank:ACL08376, Subfamily E), *L. brevis* (GenBank:ABJ63754, Subfamily J), *L. plantarum* (GenBank:CAD63310, Subfamily J), and *Bdellovibrio bacteriovorus* (GenBank:CAE80300, no subfamily), are part of the pathway that produces noticeable amounts of the methylketone 2-tridecanone through enzymatic hydrolysis of 3-keto-tetradecanoyl-ACP followed by chemical decarboxylation. *B. bacteriovorus* acyl-ACP TE produced the highest concentration of 2-tridecanone, 9.4 nmol/mL (FIG. 4), which was 3 mol % of the fatty acids produced.

The accumulation of both unsaturated fatty acids and saturated fatty acids observed is consistent with the previous conclusion that the heterologously expressed acyl-ACP TEs can intercept both saturated and unsaturated intermediates of fatty acid biosynthesis of *E. coli* (Magnuson et al., Microbiol. Rev. 57: 522-542 (1993)). Interestingly, in the *E. coli* heterologous expression system used, six bacterial-sourced acyl-ACP TEs and three plant-sourced acyl-ACP TEs produced noticeable amounts (>1 nmol/mL) of methylketones, largely 2-tridecanone. The acyl-ACP TE from *B. bacteriovorus* (GenBank: CAE80300) produced the highest concentration of 2-tridecanone (9.4 nmol/mL).

Methylketones, such as 2-tridecanone, occur in the wild tomato species *Solanum habrochaites* subsp. *Glabratum* (Antonious, J. Environ. Sci. Health B 36: 835-848 (2001)), and their biosynthesis is catalyzed by two sequentially-acting methylketone synthases, MKS1 and MKS2. MKS2 is a thioesterase that catalyzes the hydrolysis of the 3-ketoacyl-ACP intermediate in fatty acid biosynthesis, and MKS1 catalyzes the decarboxylation of the released 3-keto acid to produce a methylketone (Ben-Israel et al., Plant Physiol. 151: 1952-1964 (2009); and Yu et al., Plant Physiol. 154: 67-77 (2010)). Heterologous expression of MKS2 in *E. coli* yields many methylketones, including 2-tridecanone (Yu et al. (2010), supra). However, MKS2 is not included in Family TE14; rather, it is included in Family TE9 (Cantu et al. (2010), supra). Although some Family TE14 members share very low, if any, significant sequence similarity (i.e., <15% identity) to MKS2, the data indicate that at least nine acyl-ACP TEs (e.g., *B. bacteriovorus*, GenBank:CAE80300) can catalyze the same reaction as MKS2 (i.e, hydrolysis of the thioester bond of 3-ketoacyl-ACP), and that the resulting product (3-keto acid) is further chemically or enzymatically decarboxylated to generate the methylketone.

Example 4

This example describes statistical cluster analysis.

To classify acyl-ACP TEs based on their in vivo activities, the fatty acid composition data obtained from the in vivo expression of all TE sequences studied were used to perform statistical clustering analysis. The distance matrix was calculated using Euclidean distances, and Ward's method (Ward, J. Am. Stat. Assoc. 58: 236 (1963)) was used to perform agglomerative hierarchical clustering. The p-values were calculated via multiscale bootstrap re-sampling with 1,000 replicates (Suzuki et al., Bioinformatics 22: 1540-1542 (2006)).

All acyl-ACP TEs that were characterized were clustered into three classes: 1) Class I contains acyl-ACP TEs that mainly act on C14 and C16 substrates; 2) Class II has acyl-ACP TEs that have broad substrate specificities, with major activities toward C8 and C14 substrates; and 3) Class III comprises acyl-ACP TEs that predominantly act on C8 substrate (FIG. 5). Class I consists of thirteen plant acyl-ACP TEs from Subfamilies A, B, and D. Class II contains eleven acyl-ACP TEs, ten from bacteria in Subfamilies E, F, H, I, and J, and a non-grouped sequence, and only one from a plant (CnFatB3) in Subfamily A. Class III includes seven acyl-ACP TEs, of which three are from plants in Subfamily A and four are from bacteria in Subfamilies G and J and a non-grouped sequence. Considering the previously characterized class of oleoyl-ACP TEs in Subfamily C, TE14 members may now be sorted into four classes based on their substrate specificities.

Comparison between the specificity-based classification and the sequence-based phylogenetic tree indicates that the two classifications are not necessarily consistent with each other. Three phenomena were observed in this study. First, diverged sequences (variants in primary structure) from the same species do not necessarily differ in function. Second, similar sequences may have different substrate specificities. Third, sequences that belong to different subfamilies because they share low sequence identity can have very similar substrate specificities. Therefore, it is not reasonable to infer the substrate specificity of one acyl-ACP TE based on its sequence-based classification within the same subfamily. It is conceivable, therefore, that the change of substrate specificity is most likely caused by changes of only a few amino acid residues, and that many different combinations of residue changes could result in changed specificities (Jones (1995), supra). Bacterial orthologs provide access to additional functional diversity, both relative to acyl chain length specificity (e.g., shorter acyl chains, as short as four carbon atoms), as well as acyl chains that contain additional chemical functionalities (e.g., unsaturated acyl chains and acyl chains containing carbonyl groups).

Example 5

This example describes the generation of random mutants and site-directed mutants of acyl-ACP TE EET61113.

DNA sequences for the wild-type acyl-ACP TE EET61113 was synthesized and cloned into pUC57 vector as previously. The random mutants were generated by error-prone PCR using primers designed on pUC57 vector (pUC57F: 5'-CTG-CAAGGCGATTAAGTTGGGTAAC-3' [SEQ ID NO: 11]; pUC57R: 5'-CGGCTCGTATGTTGTGTGGAAT-3' [SEQ ID NO: 12]). The PCR was conducted in 40 tubes of reaction mixture (15 µl), which contained 1×PCR buffer, 0.2 mM dATP and dGTP, 1 mM dCTP and dTTP, 7 mM $MgCl_2$, 0.1 mM $MnCl_2$, 0.5 µl of each primers, 1.5 ng plasmid containing the thioesterase gene, and 0.15 U Taq DNA polymerase (Invitrogen), using a cycling program of 94° C. for 4 minutes, 31 cycles of 94° C. for 30 seconds, 52° C. for 30 seconds, and 72° C. for 1 minute, and a final extension step of 72° C. for 5 minutes. The PCR products were pooled together, purified with the QiaQuick gel extraction kit (Qiagen, Valencia, Calif., USA), digested with Bam HI and Eco RI, and then cloned into the corresponding restriction sites of the pUC57 vector. The constructed vectors containing mutant genes were transformed into *E. coli* K27 by electroporation.

Site-directed mutations were also introduced into wild-type acyl-ACP TE EET61113. Specifically, a mutant (designated TE20-N169Y), which contains a single N→Y mutation at amino acid position 169, and another mutant (designated TE20-S222I), which contains a single S→I mutation at amino acid position 222, were generated.

Example 6

This example describes the initial screening of acyl-ACP TE mutants generated in Example 5.

Mutants were screened on Neutral Red-containing media, which was M9 minimal medium (47.7 mM $Na_2HPO_4$, 22.1 mM $KH_2PO_4$, 8.6 mM NaCl, 18.7 mM $NH_4Cl$, 2 mM $MgSO_4$, and 0.1 mM $CaCl_2$) solidified by 15 g/L agar and supplemented with 0.4% glucose, 100 mg/L carbicillin, 1 mM IPTG, and 40 ppm Neutral Red. This screening method is based on pH change in the media. Mutants with higher acyl-ACP TE activity will produce more free fatty acids, which decrease the pH of the colonies and generate a more intense red color. Briefly, after electroporation, an appropriate amount of culture was spread on the Neutral Red plates so that each plate would contain 100-200 colonies. The plates were incubated at 30° C. for two days, and then at room temperature for another 3-5 days. Eventually, the colonies that are more intensely red were selected for further characterization with GC-MS.

Example 7

This example describes the further characterization of those mutants that were identified in Example 6 as producing more fatty acids.

Colonies that were more intensely red on the Neutral Red plate were assumed to produce more fatty acids. The activity and composition of the mutants were characterized as described above with slight modification. Instead of 20 µl of 1 M HCl, 200 µl of 1 M HCl were used to acidify the cell culture supernatant, which allowed recovery of more butanoic acid from the sample. Thus, the activity of wild-type thioesterase EET61113 in this Example was higher than the production in the above Examples.

Figure 6:
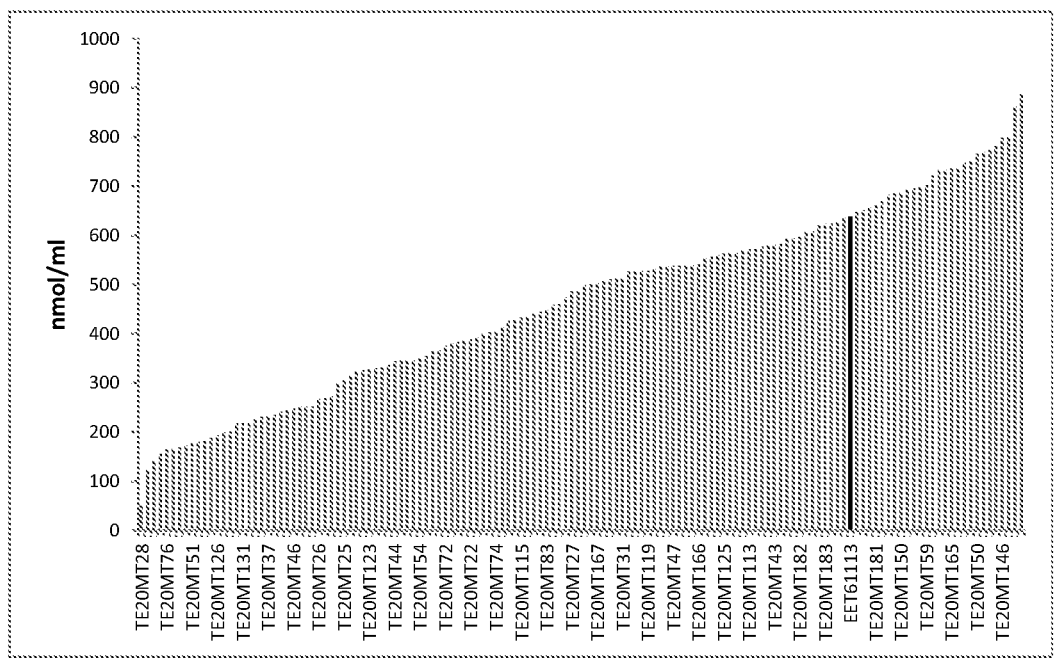
FIG. 6 is a bar graph showing total activity of wild-type acyl-ACP thioesterase from *Bryantella formatexigens* (EET61113) and mutants thereof. The data of all mutants (blue bars) were from single analyses, while the activity of wild-type was the average of 16 replicates.

The in vivo activities of 139 mutants have been determined so far. Their total activitys are shown in FIG. 6. The data of all mutants (blue bars) were from single analysis, while the activity of EET61113 (red bar) was presented as the average of 16 replicates. A total of 27 mutants showed higher acyl-ACP TE activity than wild-type, among which 8 mutants showed more than 20% increase and 2 mutants (TE20MT156 and TE20MT180) had ~40% increase. While activity increased slightly in the site-directed mutants TE20-N169Y and TE20-S222I as compared to wild-type EET61113, activity increased dramatically in a random mutant (designated TE20MT9) containing the N169Y and S222I mutations. Thus, surprisingly the double mutation had a synergistic effect, as opposed to an additive effect, on activity by the mutant acyl-ACP TE. While the wild-type TE produced approximately 50 nmol/ml culture of 4:0 fatty acids and approximately 110 nmol/ml culture of 6:0 fatty acids, the mutant designated TE20MT9 produced approximately 45 nmol/ml culture of 4:0 fatty acids and approximately 230 nmol/ml culture of 6:0 fatty acids.

Example 8

This example describes the construction of chimeric TEs.

Figure 7:
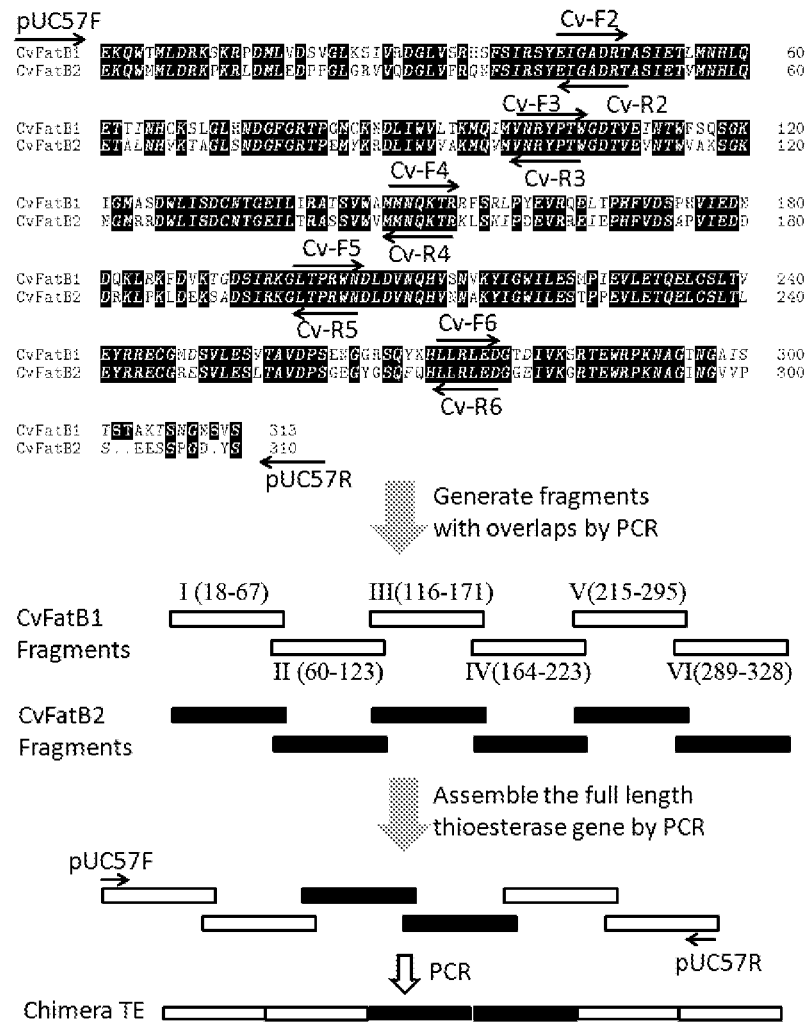
FIG. 7 is a sequence alignment of deduced amino acid sequences of *C. viscosissima* (Cv) (CvFatB1 [amino acids 107-408 of SEQ ID NO: 2], CvFatB2 [amino acids 103-404 of SEQ ID NO: 3] and the strategy to generate chimeric TEs. Arrows indicate the positions where the primers were designed. Sequences for these primers are listed in Table 2. The fragments I-VI are defined by the amino acid numbers in parentheses.

CvFatB1 and CvFatB2 share 72% identity in their amino acid sequences, but have very different substrate specificities: CvFatB1 mainly produces C8 and C10 fatty acids, while CvFatB2 produces C14 and C16 fatty acids. Chimeric TEs were constructed using these two sequences to locate the region(s) that determine the substrate specificity of acyl-ACP TEs. Previously, CvFatB1 and CvFatB2 genes were codon-optimized, synthesized, and cloned into the pUC57 vector. Using the primers listed in Table 3, six fragments (I, II, III, IV, V, and VI) for each TE gene were generated (see FIG. 7).

TABLE 3

Primers for amplification of the fragments I through VI

| Fragments | Forward primer | Reverse primer |
| --- | --- | --- |
| I | pUC57R (5'-CGGCTCGTATGTTGTGTGGAAT-3') [SEQ ID NO: 12] | Cv-R2 (5'-GGTACGATCCGCGCCGATTTC-3') [SEQ ID NO: 18] |
| II | Cv-F2 (5'-GAAATCGGCGCGGATCGTACC-3') [SEQ ID NO: 13] | Cv-R3 (5'-CCAGGTCGGATAACGATTGAC-3') [SEQ ID NO: 19] |
| III | Cv-F3 (5'-GTCAATCGTTATCCGACCTGG-3') [SEQ ID NO: 14] | Cv-R4 (5'-CGGGTTTTCTGGTTCATCAT-3') [SEQ ID NO: 20] |

TABLE 3-continued

Primers for amplification of the fragments I through VI

| Fragments | Forward primer | Reverse primer |
|---|---|---|
| IV | Cv-F4 (5'-ATGATGAACCAGAAAACCCG-3')<br>[SEQ ID NO: 15] | Cv-R5 (5'-TCGTTCCAACGCGGCGTCAGACC-3')<br>[SEQ ID NO: 21] |
| V | Cv-F5 (5'-GGTCTGACGCCGCGTTGGAACGA-3')<br>[SEQ ID NO: 16] | Cv-R6 (5'-ATCTTCCAGACGCAGCAG-3')<br>[SEQ ID NO: 22] |
| VI | Cv-F6 (5'-CTGCTGCGTCTGGAAGAT-3')<br>[SEQ ID NO: 17] | pUC57F (5'-CTGCAAGGCGATTAAGTTGGGTAAC-3')<br>[SEQ ID NO: 11] |

The chimeric TEs were constructed by re-assembling the six fragments to recreate the full-length thioesterase gene sequence by PCR, using a combination of fragments from either CvFatB1 or CvFatB2. PCR was performed in a 50-µL reaction mixture containing 10 ng of each fragment, 1× Phusion buffer, 0.2 mM dNTP, 0.5 µM pUC57F and pUC57R primers, and 1 Unit of Phusion high-fidelity DNA polymerase (New England Biolabs) using a cycling program of 98° C. for 2 minutes, 32 cycles of 98° C. for 10 seconds, 50° C. for 15 seconds, and 72° C. for 20 seconds, and a final extension step of 72° C. for 5 minutes. The expected full-length gene products were identified by agarose gel electrophoresis, recovered from the gel using the QiaQuick gel extraction kit (Qiagen, Valencia, Calif.) and cloned into the pUC57 vector using the Bam HI and Eco RI restriction sites. The sequence of each construct was confirmed by sequencing using primers pUC57F and pUC57R.

Example 9

This example describes the use of sequence alignments to identify residues that may affect substrate specificity.

A total of 27 representative acyl-ACP TE sequences, including both plant and bacterial TEs that were previously functionally characterized, were aligned using Vector NTI software (Invitrogen) with the default parameters. While Cysteine 264 was previously proposed to be a catalytic residue by Mayer et al. (J. Biol. Chem. 280: 3621-3627 (2005)), Cys264 was not conserved among these 27 TE sequences. The adjacent glutamic acid (Glu263), however, was conserved and predicted to be a catalytic residue. Multiple sequence alignment and phylogenetic analysis resulted in the identification of another nine residues that also may affect substrate specificities, namely residue 110 in Fragment II, residues 133 and 139 in Fragment III, and residues 173, 176, 184, 192, 198, and 205 in Fragment IV (see FIG. 9, which lists the amino acid present at a given position for the indicated organism). The presence of leucine (L) or valine (V) at position 110, phenylalanine (F) or leucine (L) at position 133, isoleucine (I) at position 139, phenylalanine (F) or leucine (L) at position 173, leucine (L) at position 176, isoleucine (I), phenylalanine (F) or leucine (L) at position 184, proline (P) at position 192, asparagine (N) or serine (S) at position 198, and phenylalanine (F) at position 205 were associated with the production of mainly C8 fatty acids. The production of mainly C14/16 fatty acids was associated with the presence of valine (V) or leucine (L) at position 110, valine (V) or alanine (A) at position 133, asparagine (N) at position 139, leucine (L) at position 173, isoleucine (I), phenylalanine (F), valine (V), or methionine (M) at position 176, isoleucine (I; or, in one instance, leucine (L)) at position 184, threonine (T), serine (S), valine (V), alanine (A), proline (P), or aspartic acid (D) at position 192, aspartic acid (D) at position 198, and leucine (L) at position 205. Site-directed mutagenesis and fatty acid profiling were used for verification.

Example 10

This example describes the use of site-directed mutagenesis to verify residues that may affect substrate specificity.

Figure 10:
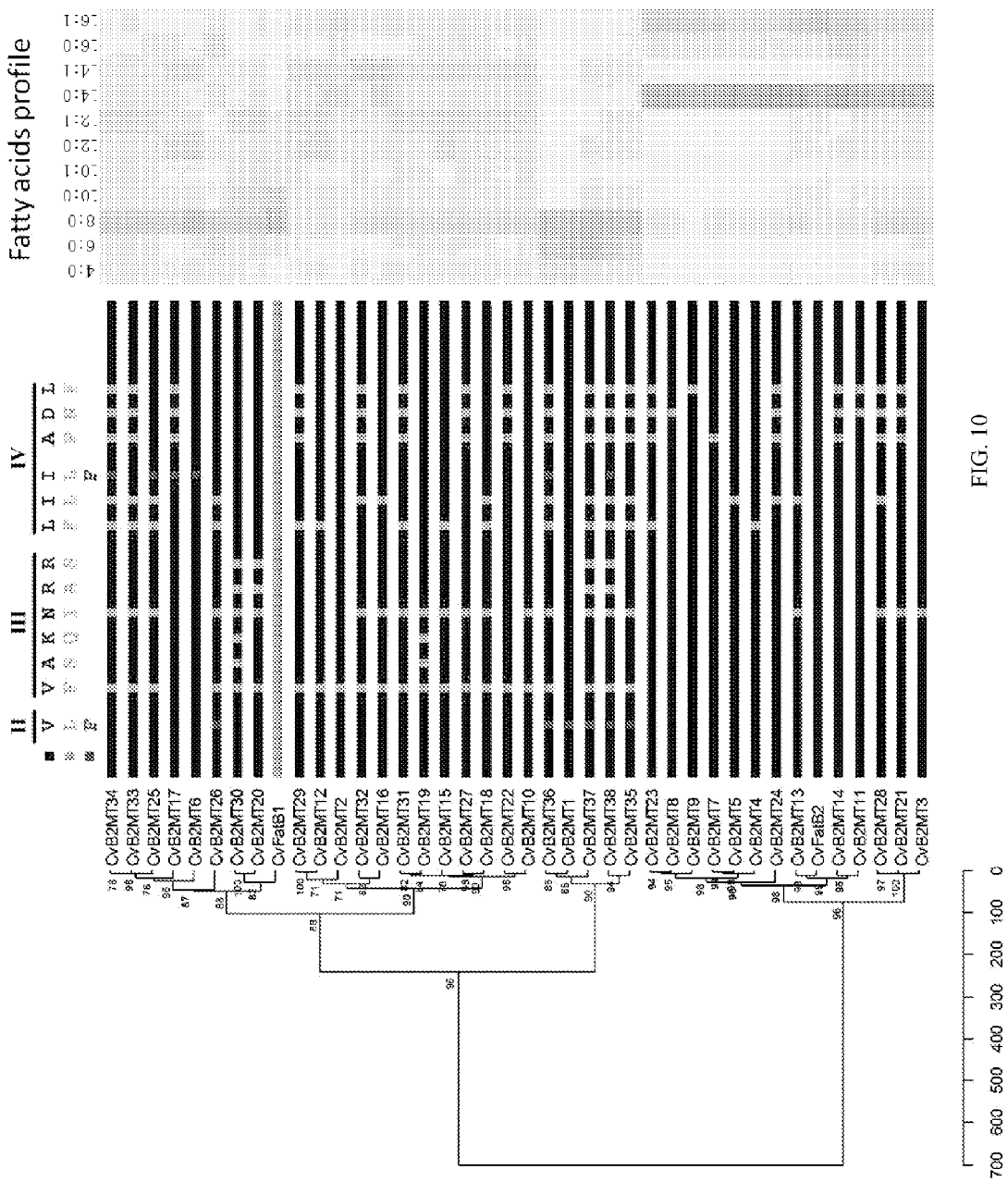
FIG. 10 shows the fatty acid profiles of TE mutants on the right, wherein the green color highlights the major fatty acids produced by the TEs, the cluster analysis of the fatty acid profiles on the left, and the point mutations in each TE mutant in the middle. The wild-type enzyme is CvFatB2, which is shown in the color blue. The color orange indicates residues that have been mutated to the amino acid present at the corresponding position in CvFatB1. Red points indicate residues that have been mutated to amino acids that are not present in CvFatB1 or CvFatB2.

Point mutants were generated from CvFatB2 with the QuikChange II site-directed mutagenesis kit (Agilent Technologies) according to manufacturer's instructions in order to test whether the predicted residues, which were identified in Example 9, affected the substrate specificity of acyl-ACP TEs. The residues of CvFatB2 were mutated to the corresponding residues in CvFatB1 with the exception of residues valine 110 (V110) and isoleucine 184 (I184), which were mutated to the bulkier residue, phenylalanine. The point mutations were introduced sequentially for the mutants that harbored multiple amino acid changes. All mutants were confirmed by sequencing. The results are shown in FIG. 10, which shows the fatty acid profiles of the mutants on the right (wherein the green color highlights the major fatty acids produced by the TEs), the cluster analysis of the fatty acid profiles on the left, and the point mutations in each mutant in the middle. The wild-type enzyme is CvFatB2, which is shown in the color blue. The color orange indicates residues that have been mutated to the amino acid present at the corresponding position in CvFatB1. Red points indicate residues that have been mutated to amino acids that are not present in CvFatB1 or CvFatB2.

Example 11

This example describes the production of fatty acids in vivo by TE variants.

Figure 8A:
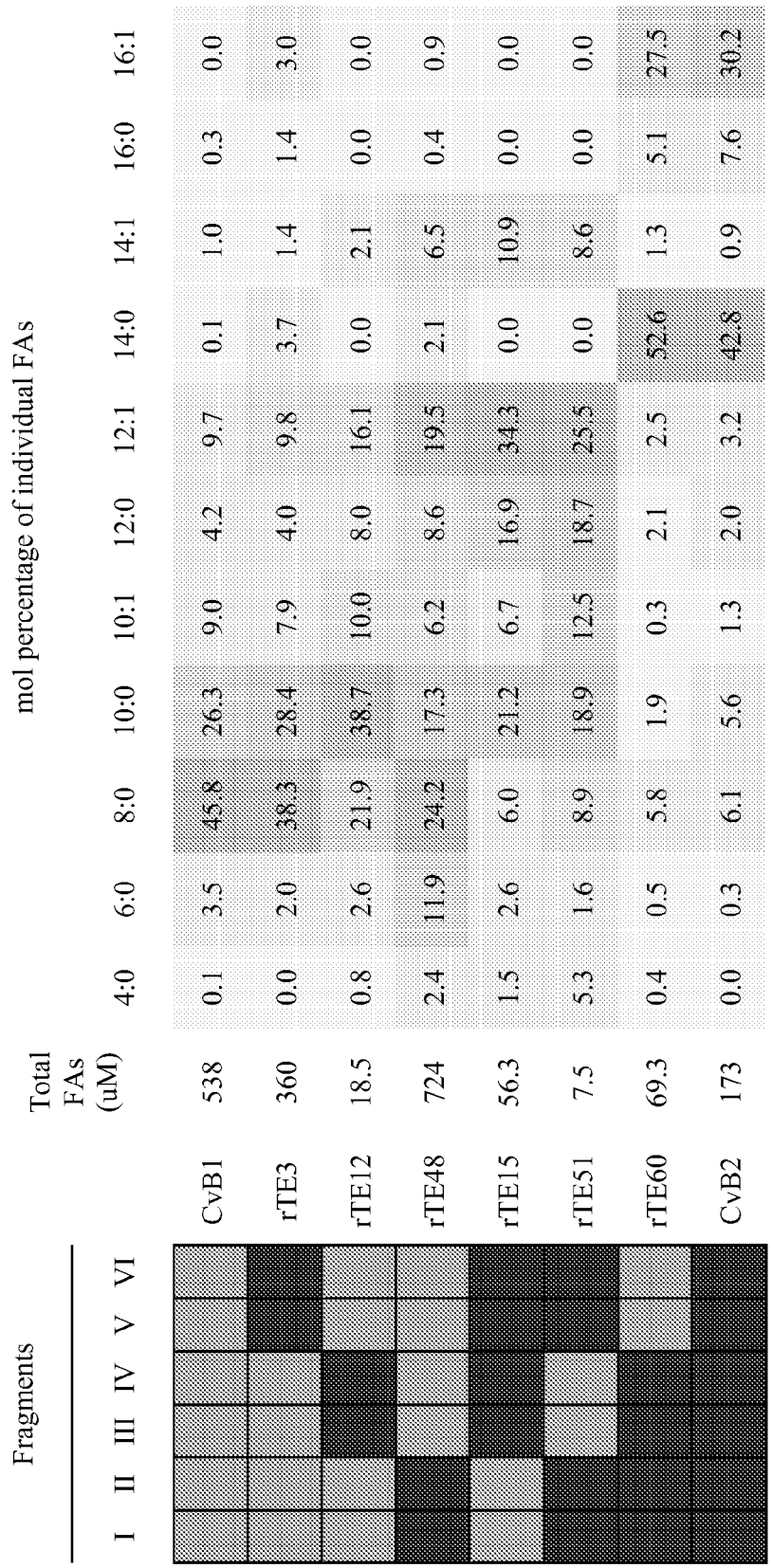
FIG. 8a shows the mole percentage of individual fatty acids (FAs) from 4:0 to 16:1 as well as the total FAs (μM) for each of six chimeric TEs (i.e., rTE3, rTE12, rTE48, rTE15, rTE51, and rTE60) and *C. viscosissima* FatB1 (CvB1) and FatB2 (CvB2).

TE variants were analyzed in accordance with the method of Example 3. The results are shown in FIGS. 8a and 8b. As shown in FIGS. 8a and 8b, the biggest variances among the chimeric TEs were observed for 8:0 and 14:0 fatty acids. The mole percentages of 8:0 and 14:0 fatty acids for all chimeric TEs were plotted, and it was determined that the replacement of Fragment III changed the fatty acid profile most dramatically. Thus, Fragment III was determined to contain the most important residues for substrate specificity, although Fragments I, II, and IV also affected substrate specificity.

Thus, in view of the above, the present invention provides the following:

A. A method of increasing production of fatty acids in a host cell or organism, which method comprises introducing into the host cell or organism and expressing therein a nucleic acid molecule comprising a nucleotide sequence encoding an acyl-acyl carrier protein (ACP) thioesterase (TE) from *Bry-* antella formatexigens, whereupon the production of fatty acids in the host cell or organism is increased.

B. The method of A, wherein the host cell or organism is a bacterium, a yeast, an alga, or a crop plant.

C. A method of increasing production of short-chain fatty acids in a host cell or organism, which method comprises introducing into the host cell or organism and expressing therein a nucleic acid molecule comprising a nucleotide sequence encoding a mutant acyl-ACP TE derived from wild-type *Bryantella formatexigens* acyl-ACP TE, whereupon the production of short-chain fatty acids in the host cell or organism is increased and wherein the mutant acyl-ACP TE produces more short-chain fatty acids in the host cell or organism than the corresponding wild-type acyl-ACP TE.

D. The method of C, wherein the mutant acyl-ACP TE differs from wild-type *Bryantella formatexigens* acyl-ACP TE by two or more amino acid mutations comprising N169Y and S222I and wherein the mutant acyl-ACP TE has increased thioesterase activity compared to wild-type *Bryantella formatexigens* acyl-ACP TE.

E. The method of C, wherein the host cell or organism is a bacterium, a yeast, an alga, or a crop plant.

F. The method of D, wherein the host cell or organism is a bacterium, a yeast, an alga, or a crop plant.

G. A method of making a mutant *Bryantella formatexigens* acyl-ACP TE, which method comprises making a mutant *Bryantella formatexigens* acyl-ACP TE comprising two or more amino acid mutations comprising N169Y and S222I, whereupon a mutant *Bryantella formatexigens* acyl-ACP TE is made.

H. The method of G, wherein the mutant *Bryantella formatexigens* acyl-ACP TE has increased thioesterase activity compared to a corresponding wild-type *Bryantella formatexigens* acyl-ACP TE.

I. An isolated or purified nucleic acid molecule comprising a nucleotide sequence encoding a mutant acyl-ACP TE, which is derived from wild-type *Bryantella formatexigens* acyl-ACP TE, comprises two or more amino acid mutations comprising N169Y and S222I, and has increased thioesterase activity compared to wild-type *Bryantella formatexigens* acyl-ACP TE, wherein the isolated or purified nucleic acid molecule can be a vector.

J. A host cell or organism comprising the isolated or purified nucleic acid molecule of I.

K. The host cell or organism of J, wherein the host cell or organism is a bacterium, a yeast, an alga, or a crop plant.

L. An isolated or purified mutant acyl-ACP TE, which is derived from wild-type *Bryantella formatexigens* acyl-ACP TE, comprises two or more amino acid mutations comprising N169Y and S222I, and has increased thioesterase activity compared to wild-type *Bryantella formatexigens* acyl-ACP TE.

M. A method of making a chimeric *Cuphea viscosissima* acyl-ACP TE, which method comprises replacing a segment of a wild-type *Cuphea viscosissima* acyl-ACP TE with a segment of another acyl-ACP TE, whereupon a chimeric *Cuphea viscosissima* acyl-ACP TE is made.

N. The method of M, wherein the segment of another acyl-ACP TE gene is a segment of another *Cuphea viscosissima* acyl-ACP TE.

O. The method of M, which method comprises replacing a segment of a wild-type *Cuphea viscosissima* FatB1 (CvFatB1) gene with a segment of another acyl-ACP TE gene to produce a chimeric CvFatB1 gene or replacing a segment of a wild-type *Cuphea viscosissima* FatB2 (CvFatB2) gene with a segment of another acyl-ACP TE gene to produce a chimeric CvFatB2 gene.

P. The method of O, which method comprises replacing a segment of a wild-type CvFatB1 gene with a segment of a CvFatB2 gene to produce a chimeric CvFatB1 gene or replacing a segment of a wild-type CvFatB2 gene with a segment of a CvFatB1 gene to produce a chimeric CvFatB2 gene.

Q. The method of M, wherein the chimeric *Cuphea viscosissima* acyl-ACP TE (i) has a substrate specificity that differs from the corresponding wild-type *Cuphea viscosissima* acyl-ACP TE, (ii) produces a total amount of fatty acids that differs from the total amount of fatty acids produced by the corresponding wild-type *Cuphea viscosissima* acyl-ACP TE, or (iii) has a substrate specificity and produces a level of a fatty acid, both of which differ from the corresponding wild-type *Cuphea viscosissima* acyl-ACP TE.

R. An isolated or purified nucleic acid molecule comprising a nucleotide sequence encoding a chimeric *Cuphea viscosissima* acyl-ACP TE gene, which comprises a segment of another acyl-ACP TE gene, wherein the isolated or purified nucleic acid molecule can be a vector.

S. The isolated or purified nucleic acid molecule of R, wherein the segment of another acyl-ACP TE gene is a segment of another *Cuphea viscosissima* acyl-ACP TE gene.

T. The isolated or purified nucleic acid molecule of R, wherein the chimeric *Cuphea viscosissima* acyl-ACP TE gene is a chimeric FatB1 gene or a chimeric FatB2 gene.

U. The isolated or purified nucleic acid molecule of T, wherein the chimeric *Cuphea viscosissima* acyl-ACP TE gene is a chimeric FatB1 gene comprising a segment of a *Cuphea viscosissima* FatB2 gene or the chimeric *Cuphea viscosissima* acyl-ACP TE gene is a chimeric FatB2 gene comprising a segment of a *Cuphea viscosissima* FatB1 gene.

V. A host cell or organism comprising the isolated or purified nucleic acid molecule of R-µ.

W. An isolated or purified chimeric *Cuphea viscosissima* acyl-ACP TE, which comprises a segment of another acyl-ACP TE.

X. The isolated or purified chimeric *Cuphea viscosissima* acyl-ACP TE of W, wherein the segment of another acyl-ACP TE is a segment of another *Cuphea viscosissima* acyl-ACP TE.

Y. The isolated or purified chimeric *Cuphea viscosissima* acyl-ACP TE of W, which is a chimera of the TE encoded by a FatB1 gene or a chimera of the TE encoded by a FatB2 gene.

Z. The isolated or purified chimeric *Cuphea viscosissima* acyl-ACP TE of Y, which is a chimera of the TE encoded by a FatB1 gene comprising a segment of the TE encoded by a FatB2 gene or a chimera of the TE encoded by a FatB2 gene comprising a segment of the TE encoded by a FatB1 gene.

AA. A method of altering the specificity of a plant acyl-ACP TE for at least one of its substrates, which method comprises introducing into the plant acyl-ACP TE a substrate specificity-altering mutation in the region corresponding to amino acids 118-167 of the mature amino acid sequence of the *Cuphea viscosissima* acyl-ACP TE encoded by FatB2, whereupon the specificity of the plant acyl-ACP TE for at least one of its substrates is altered.

AB. The method of AA, which comprises mutating at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2.

AC. The method of AB, which further comprises mutating at least one amino acid corresponding to an amino acid selected from the group consisting of amino acid 110 and amino acid 184 of the mature amino acid sequence of the *Cuphea viscosissima* acyl-ACP TE encoded by FatB2.

AD. The method of AA, which further comprises altering the level of activity of the plant acyl-ACP TE by a method comprising mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2, whereupon the level of activity of the plant acyl-ACP TE is altered.

AE. The method of AB, which further comprises altering the level of activity of the plant acyl-ACP TE by a method comprising mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2, whereupon the level of activity of the plant acyl-ACP TE is altered.

AF. The method of AC, which further comprises altering the level of activity of the plant acyl-ACP TE by a method comprising mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2, whereupon the level of activity of the plant acyl-ACP TE is altered.

AG. A method of altering the level of activity of a plant acyl-ACP TE, which method comprises mutating at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2, whereupon the level of activity of the plant acyl-ACP TE is altered.

AH. The method of AG, which further comprises altering the specificity of the plant acyl-ACP TE for at least one of its substrates by a method comprising introducing into the plant acyl-ACP TE a substrate specificity-altering mutation in the region corresponding to amino acids 118-167 of the mature amino acid sequence of the *Cuphea viscosissima* acyl-ACP TE encoded by FatB2, whereupon the specificity of the plant acyl-ACP TE for at least one of its substrates is altered.

AI. The method of AH, which comprises mutating at least one amino acid selected from the group consisting of amino acid 133, amino acid 142, and amino acid 143 of the mature amino acid sequence of the *Cuphea viscosissima* acyl-ACP TE encoded by FatB2.

AJ. The method of AI, which further comprises mutating at least one amino acid corresponding to an amino acid selected from the group consisting of amino acid 110 and amino acid 184 of the mature amino acid sequence of the *Cuphea viscosissima* acyl-ACP TE encoded by FatB2.

AK. An isolated or purified nucleic acid molecule comprising a nucleotide sequence encoding a mutant plant acyl-ACP TE, which comprises a substrate specificity-altering mutation in the region corresponding to amino acids 118-167 of the mature amino acid sequence of the *Cuphea viscosissima* acyl-ACP TE encoded by FatB2, wherein the isolated or purified nucleic acid molecule can be a vector.

AL. The isolated or purified nucleic acid molecule of AK, wherein the mutant plant acyl-ACP TE comprises a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2.

AM. The isolated or purified nucleic acid molecule of AL, wherein the mutant plant acyl-ACP TE further comprises a mutation of at least one amino acid corresponding to an amino acid selected from the group consisting of amino acid 110 and amino acid 184 of the mature amino acid sequence of the *Cuphea viscosissima* acyl-ACP TE encoded by FatB2.

AN. The isolated or purified nucleic acid molecule of AK-AM, wherein the mutant plant acyl-ACP TE further comprises a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

AO. An isolated or purified nucleic acid molecule comprising a nucleotide sequence encoding a mutant plant acyl-ACP TE, which comprises a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2, wherein the isolated or purified nucleic acid molecule can be a vector.

AP. The isolated or purified nucleic acid molecule of AO, wherein the mutant plant acyl-ACP TE further comprises a substrate specificity-altering mutation in the region corresponding to amino acids 118-167 of the mature amino acid of the *Cuphea viscosissima* acyl-ACP TE encoded by FatB2.

AQ. The isolated or purified nucleic acid molecule of AP, wherein the mutant plant acyl-ACP TE comprises a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2.

AR. The isolated or purified nucleic acid molecule of AQ, wherein the mutant plant acyl-ACP TE further comprises a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2.

AS. A host cell or organism comprising the isolated or purified nucleic acid molecule of AK-AR.

AT. An isolated or purified mutant plant acyl-ACP TE, which comprises a substrate specificity-altering mutation in the region corresponding to amino acids 118-167 of the mature amino acid sequence of the *Cuphea viscosissima* acyl-ACP TE encoded by FatB2.

AU. The isolated or purified mutant plant acyl-ACP TE of AT, which comprises a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2.

AV. The isolated or purified mutant plant acyl-ACP TE of AU, which further comprises a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2.

AW. The isolated or purified mutant plant acyl-ACP TE of AT-AV, which further comprises a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

AX. An isolated or purified mutant plant acyl-ACP TE, which comprises a level of activity-altering mutation of at least one amino acid corresponding to an amino acid selected from the group consisting of amino acid 173, amino acid 176, and amino acid 205 of the mature amino acid sequence of the *Cuphea viscosissima* acyl-ACP TE encoded by FatB2.

AY. The isolated or purified mutant plant acyl-ACP TE of claim AX, which further comprises a substrate specificity-altering mutation in the region corresponding to amino acids 118-167 of the mature amino acid of the *Cuphea viscosissima* acyl-ACP TE encoded by FatB2.

AZ. The isolated or purified mutant plant acyl-ACP TE of claim AY, which comprises a mutation of at least one amino acid corresponding to an amino acid selected from the group consisting of amino acid 133, amino acid 142, and amino acid 143 of the mature amino acid sequence of the *Cuphea viscosissima* acyl-ACP TE encoded by FatB2.

BA. The isolated or purified mutant plant acyl-ACP TE of claim AZ, which further comprises a substrate specificity-altering mutation of at least one amino acid corresponding to an amino acid selected from the group consisting of amino acid 110 and amino acid 184 of the mature amino acid sequence of the *Cuphea viscosissima* acyl-ACP TE encoded by FatB2.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of increasing production of short-chain fatty acids in a host cell or organism, which method comprises introducing into the host cell or organism and expressing therein a nucleic acid molecule comprising a nucleotide sequence encoding a mutant acyl-acyl carrier protein (ACP) thioesterase (TE) acyl-ACP TE), which is derived from wild-type Bryantella formatexigens acyl-ACP TE having the amino acid sequence of SEQ ID NO:24, comprises two amino acid mutations comprising N169Y and S222I, and has increased thioesterase activity compared to wild-type Bryantella formatexigens acyl-ACP TE having the amino acid sequence of SEQ ID NO:24, whereupon the production of short-chain fatty acids in the host cell or organism is increased and wherein the mutant acyl-ACP TE produces more short-chain fatty acids in the host cell or organism than the corresponding wild-type acyl-ACP TE.

2. The method of claim 1, wherein the host cell or organism is a bacterium, a yeast, an alga, or a crop plant.

3. The method of claim 2, wherein the bacterium is *E. coli*.

* * * * *

SEQUENCE LISTING

```
<160> NUMBER OF SEQ ID NOS: 24

<210> SEQ ID NO 1
<211> LENGTH: 412
<212> TYPE: PRT
<213> ORGANISM: Cuphea viscosissima

<400> SEQUENCE: 1

Met Val Ala Ala Ala Ser Ser Ala Phe Phe Ser Phe Pro Thr Pro
1               5                   10                  15

Gly Thr Ser Pro Lys Pro Gly Lys Phe Gly Asn Trp Pro Ser Ser Leu
                20                  25                  30

Ser Ile Pro Phe Asn Pro Lys Ser Asn His Asn Gly Gly Ile Gln Val
            35                  40                  45

Lys Ala Asn Ala Ser Ala His Pro Lys Ala Asn Gly Ser Ala Val Ser
        50                  55                  60

Leu Lys Ala Gly Ser Leu Glu Thr Gln Glu Asp Thr Ser Ser Pro Ser
65                  70                  75                  80

Pro Pro Pro Arg Thr Phe Ile Ser Gln Leu Pro Asp Trp Ser Met Leu
                85                  90                  95

Val Ser Ala Ile Thr Thr Val Phe Val Ala Ala Glu Lys Gln Trp Thr
            100                 105                 110

Met Leu Asp Arg Lys Ser Lys Arg Pro Asp Val Leu Val Glu Pro Phe
        115                 120                 125

Val Gln Asp Gly Val Ser Phe Arg Gln Ser Phe Ser Ile Arg Ser Tyr
    130                 135                 140

Glu Ile Gly Val Asp Arg Thr Ala Ser Ile Glu Thr Leu Met Asn Ile
145                 150                 155                 160

Phe Gln Glu Thr Ser Leu Asn His Cys Lys Ser Leu Gly Leu Leu Asn
                165                 170                 175

Asp Gly Phe Gly Arg Thr Pro Glu Met Cys Lys Arg Asp Leu Ile Trp
            180                 185                 190

Val Val Thr Lys Met Gln Ile Glu Val Asn Arg Tyr Pro Thr Trp Gly
```

```
                195                 200                 205
Asp Thr Ile Glu Val Thr Thr Trp Val Ser Glu Ser Gly Lys Asn Gly
210                 215                 220

Met Ser Arg Asp Trp Leu Ile Ser Asp Cys His Ser Gly Glu Ile Leu
225                 230                 235                 240

Ile Arg Ala Thr Ser Val Trp Ala Met Met Asn Gln Lys Thr Arg Arg
                245                 250                 255

Leu Ser Lys Ile Pro Asp Glu Val Arg Gln Glu Ile Val Pro Tyr Phe
            260                 265                 270

Val Asp Ser Ala Pro Val Ile Glu Asp Asp Arg Lys Leu His Lys Leu
        275                 280                 285

Asp Val Lys Thr Gly Asp Ser Ile Arg Asn Gly Leu Thr Pro Arg Trp
    290                 295                 300

Asn Asp Phe Asp Val Asn Gln His Val Asn Asn Val Lys Tyr Ile Ala
305                 310                 315                 320

Trp Leu Leu Lys Ser Val Pro Thr Glu Val Phe Glu Thr Gln Glu Leu
                325                 330                 335

Cys Gly Leu Thr Leu Glu Tyr Arg Arg Glu Cys Arg Arg Asp Ser Val
            340                 345                 350

Leu Glu Ser Val Thr Ala Met Asp Pro Ser Lys Glu Gly Asp Arg Ser
        355                 360                 365

Leu Tyr Gln His Leu Leu Arg Leu Glu Asn Gly Ala Asp Ile Ala Leu
    370                 375                 380

Gly Arg Thr Glu Trp Arg Pro Lys Asn Ala Gly Ala Thr Gly Ala Val
385                 390                 395                 400

Ser Thr Gly Lys Thr Ser Asn Gly Asn Ser Val Ser
                405                 410

<210> SEQ ID NO 2
<211> LENGTH: 419
<212> TYPE: PRT
<213> ORGANISM: Cuphea viscosissima

<400> SEQUENCE: 2

Met Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
                20                  25                  30

Ser Pro Thr Phe Lys Pro Lys Ser Ile Pro Asn Gly Gly Phe Gln Val
            35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg His Ser Phe Ser
    130                 135                 140

Ile Arg Ser Tyr Glu Ile Gly Ala Asp Arg Thr Ala Ser Ile Glu Thr
145                 150                 155                 160
```

```
Leu Met Asn His Leu Gln Glu Thr Thr Ile Asn His Cys Lys Ser Leu
                    165                 170                 175

Gly Leu His Asn Asp Gly Phe Gly Arg Thr Pro Gly Met Cys Lys Asn
                180                 185                 190

Asp Leu Ile Trp Val Leu Thr Lys Met Gln Ile Met Val Asn Arg Tyr
            195                 200                 205

Pro Thr Trp Gly Asp Thr Val Glu Ile Asn Thr Trp Phe Ser Gln Ser
        210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
                260                 265                 270

Thr Pro His Phe Val Asp Ser Pro His Val Ile Glu Asp Asn Asp Gln
            275                 280                 285

Lys Leu Arg Lys Phe Asp Val Lys Thr Gly Asp Ser Ile Arg Lys Gly
        290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
                340                 345                 350

Gly Met Asp Ser Val Leu Glu Ser Val Thr Ala Val Asp Pro Ser Glu
            355                 360                 365

Asn Gly Gly Arg Ser Gln Tyr Lys His Leu Leu Arg Leu Glu Asp Gly
        370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser

<210> SEQ ID NO 3
<211> LENGTH: 412
<212> TYPE: PRT
<213> ORGANISM: Cuphea viscosissima

<400> SEQUENCE: 3

Thr Ala Ala Ser Ser Ala Phe Phe Pro Val Pro Ser Ala Asp Thr Ser
1               5                   10                  15

Ser Arg Pro Gly Lys Leu Gly Asn Gly Pro Ser Ser Phe Ser Pro Leu
                20                  25                  30

Lys Pro Lys Ser Ile Pro Asn Gly Gly Leu Gln Val Lys Ala Ser Ala
            35                  40                  45

Ser Ala Pro Pro Lys Ile Asn Gly Ser Ser Val Gly Leu Lys Ser Gly
        50                  55                  60

Gly Leu Lys Thr His Asp Asp Ala Pro Ser Ala Pro Pro Pro Arg Thr
65                  70                  75                  80

Phe Ile Asn Gln Leu Pro Asp Trp Ser Met Leu Leu Ala Ala Ile Thr
                85                  90                  95

Thr Ala Phe Leu Ala Ala Glu Lys Gln Trp Met Met Leu Asp Arg Lys
                100                 105                 110
```

```
Pro Lys Arg Leu Asp Met Leu Glu Asp Pro Phe Gly Leu Gly Arg Val
            115                 120                 125

Val Gln Asp Gly Leu Val Phe Arg Gln Asn Phe Ser Ile Arg Ser Tyr
        130                 135                 140

Glu Ile Gly Ala Asp Arg Thr Ala Ser Ile Glu Thr Val Met Asn His
145                 150                 155                 160

Leu Gln Glu Thr Ala Leu Asn His Val Lys Thr Ala Gly Leu Ser Asn
                165                 170                 175

Asp Gly Phe Gly Arg Thr Pro Glu Met Tyr Lys Arg Asp Leu Ile Trp
            180                 185                 190

Val Val Ala Lys Met Gln Val Met Val Asn Arg Tyr Pro Thr Trp Gly
        195                 200                 205

Asp Thr Val Glu Val Asn Thr Trp Val Ala Lys Ser Gly Lys Asn Gly
210                 215                 220

Met Arg Arg Asp Trp Leu Ile Ser Asp Cys Asn Thr Gly Glu Ile Leu
225                 230                 235                 240

Thr Arg Ala Ser Ser Val Trp Val Met Met Asn Gln Lys Thr Arg Lys
                245                 250                 255

Leu Ser Lys Ile Pro Asp Glu Val Arg Arg Glu Ile Glu Pro His Phe
            260                 265                 270

Val Asp Ser Ala Pro Val Ile Glu Asp Asp Arg Lys Leu Pro Lys
        275                 280                 285

Leu Asp Glu Lys Ser Ala Asp Ser Ile Arg Lys Gly Leu Thr Pro Arg
290                 295                 300

Trp Asn Asp Leu Asp Val Asn Gln His Val Asn Asn Ala Lys Tyr Ile
305                 310                 315                 320

Gly Trp Ile Leu Glu Ser Thr Pro Pro Glu Val Leu Glu Thr Gln Glu
                325                 330                 335

Leu Cys Ser Leu Thr Leu Glu Tyr Arg Arg Glu Cys Gly Arg Glu Ser
            340                 345                 350

Val Leu Glu Ser Leu Thr Ala Val Asp Pro Ser Gly Glu Gly Tyr Gly
        355                 360                 365

Ser Gln Phe Gln His Leu Leu Arg Leu Glu Asp Gly Gly Glu Ile Val
370                 375                 380

Lys Gly Arg Thr Glu Trp Arg Pro Lys Asn Ala Gly Ile Asn Gly Val
385                 390                 395                 400

Val Pro Ser Glu Glu Ser Ser Pro Gly Asp Tyr Ser
                405                 410

<210> SEQ ID NO 4
<211> LENGTH: 423
<212> TYPE: PRT
<213> ORGANISM: Cuphea nucifera

<400> SEQUENCE: 4

Met Val Ala Ser Ile Ala Ala Ser Ala Phe Phe Pro Thr Pro Ser Ser
1               5                   10                  15

Ser Ser Ser Ala Ala Ser Ala Lys Ala Ser Lys Thr Ile Gly Glu Gly
                20                  25                  30

Pro Gly Ser Leu Asp Val Arg Gly Ile Val Ala Lys Pro Thr Ser Ser
            35                  40                  45

Ser Ala Ala Met Gln Glu Lys Val Lys Val Gln Pro Val Pro Lys Ile
        50                  55                  60

Asn Gly Ala Lys Val Gly Leu Lys Val Glu Thr Gln Lys Ala Asp Glu
65                  70                  75                  80
```

Glu Ser Ser Pro Ser Ser Ala Pro Arg Thr Phe Tyr Asn Gln Leu Pro
            85                  90                  95

Asp Trp Ser Val Leu Leu Ala Ala Val Thr Thr Ile Phe Leu Ala Ala
            100                 105                 110

Glu Lys Gln Trp Thr Leu Leu Asp Trp Lys Pro Arg Arg Pro Asp Met
            115                 120                 125

Leu Ala Asp Ala Phe Gly Leu Gly Lys Ile Val Gln Asp Gly Leu Val
130                 135                 140

Phe Lys Gln Asn Phe Ser Ile Arg Ser Tyr Glu Ile Gly Ala Asp Arg
145                 150                 155                 160

Thr Ala Ser Ile Glu Thr Leu Met Asn His Leu Gln Glu Thr Ala Leu
                165                 170                 175

Asn His Val Lys Ser Ala Gly Leu Met Gly Asp Gly Phe Gly Ala Thr
            180                 185                 190

Pro Glu Met Ser Lys Arg Asn Leu Ile Trp Val Val Thr Lys Met Arg
            195                 200                 205

Val Leu Ile Glu Arg Tyr Pro Ser Trp Gly Asp Val Val Glu Val Asp
            210                 215                 220

Thr Trp Val Gly Pro Thr Gly Lys Asn Gly Met Arg Arg Asp Trp His
225                 230                 235                 240

Val Arg Asp His Arg Ser Gly Gln Thr Ile Leu Arg Ala Thr Ser Val
                245                 250                 255

Trp Val Met Met Asn Lys Asn Thr Arg Lys Leu Ser Lys Val Pro Glu
            260                 265                 270

Glu Val Arg Ala Glu Ile Gly Pro Tyr Phe Val Glu Arg Ala Ala Ile
            275                 280                 285

Val Asp Glu Asp Ser Arg Lys Leu Pro Lys Leu Asp Glu Asp Thr Thr
290                 295                 300

Asp Tyr Ile Lys Lys Gly Leu Thr Pro Arg Trp Gly Asp Leu Asp Val
305                 310                 315                 320

Asn Gln His Val Asn Asn Val Lys Tyr Ile Gly Trp Ile Leu Glu Ser
                325                 330                 335

Ala Pro Ile Ser Ile Leu Glu Asn His Glu Leu Ala Ser Met Ser Leu
            340                 345                 350

Glu Tyr Arg Arg Glu Cys Gly Arg Asp Ser Val Leu Gln Ser Leu Thr
            355                 360                 365

Ala Val Ser Asn Asp Leu Thr Asp Gly Leu Val Glu Ser Gly Ile Glu
370                 375                 380

Cys Gln His Leu Leu Gln Leu Glu Cys Gly Thr Glu Leu Val Lys Gly
385                 390                 395                 400

Arg Thr Glu Trp Arg Pro Lys His Ser Pro Ala Leu Gly Asn Met Gly
                405                 410                 415

Pro Thr Pro Gly Gly Ser Ala
            420

<210> SEQ ID NO 5
<211> LENGTH: 417
<212> TYPE: PRT
<213> ORGANISM: Cuphea nucifera

<400> SEQUENCE: 5

Met Val Ala Ser Val Ala Ala Ser Ala Phe Phe Pro Thr Pro Ser Phe
1               5                   10                  15

Ser Ser Thr Ala Ser Ala Lys Ala Ser Lys Thr Ile Gly Glu Gly Ser

```
            20                  25                  30
Glu Ser Leu Asp Val Arg Gly Ile Val Ala Lys Pro Thr Ser Ser Ser
         35                  40                  45

Ala Ala Met Gln Gly Lys Val Lys Ala Gln Ala Val Pro Lys Ile Asn
     50                  55                  60

Gly Thr Lys Val Gly Leu Lys Thr Glu Ser Gln Lys Ala Glu Glu Asp
 65                  70                  75                  80

Ala Ala Pro Ser Ser Ala Pro Arg Thr Phe Tyr Asn Gln Leu Pro Asp
                 85                  90                  95

Trp Ser Val Leu Leu Ala Ala Val Thr Thr Ile Phe Leu Ala Ala Glu
            100                 105                 110

Lys Gln Trp Thr Leu Leu Asp Trp Lys Pro Arg Arg Pro Asp Met Leu
        115                 120                 125

Thr Asp Ala Phe Ser Leu Gly Lys Ile Val Gln Asp Gly Leu Ile Phe
    130                 135                 140

Arg Gln Asn Phe Ser Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Arg Asn Ala Gly Leu Leu Gly Asp Gly Phe Gly Ala Thr Pro
            180                 185                 190

Glu Met Ser Lys Arg Asn Leu Ile Trp Val Val Thr Lys Met Gln Val
        195                 200                 205

Leu Val Glu His Tyr Pro Ser Trp Gly Asp Val Val Glu Val Asp Thr
    210                 215                 220

Trp Val Gly Ala Ser Gly Lys Asn Gly Met Arg Arg Asp Trp His Val
225                 230                 235                 240

Arg Asp Tyr Arg Thr Gly Gln Thr Ile Leu Arg Ala Thr Ser Val Trp
                245                 250                 255

Val Met Met Asn Lys His Thr Arg Lys Leu Ser Lys Met Pro Glu Glu
            260                 265                 270

Val Arg Ala Glu Ile Gly Pro Tyr Phe Val Glu His Ala Ala Ile Val
        275                 280                 285

Asp Glu Asp Ser Arg Lys Leu Pro Lys Leu Asp Asp Thr Ala Asp
    290                 295                 300

Tyr Ile Lys Trp Gly Leu Thr Pro Arg Trp Ser Asp Leu Asp Val Asn
305                 310                 315                 320

Gln His Val Asn Asn Val Lys Tyr Ile Gly Trp Ile Leu Glu Ser Ala
                325                 330                 335

Pro Ile Ser Ile Leu Glu Asn His Glu Leu Ala Ser Met Thr Leu Glu
            340                 345                 350

Tyr Arg Arg Glu Cys Gly Arg Asp Ser Val Leu Gln Ser Leu Thr Ala
        355                 360                 365

Ile Ser Asn Asp Cys Thr Gly Gly Leu Pro Glu Ala Ser Ile Glu Cys
    370                 375                 380

Gln His Leu Leu Gln Leu Glu Cys Gly Ala Glu Ile Val Arg Gly Arg
385                 390                 395                 400

Thr Gln Trp Arg Pro Arg Arg Ala Ser Gly Pro Thr Ser Ala Gly Ser
                405                 410                 415

Ala

<210> SEQ ID NO 6
<211> LENGTH: 414
```

<212> TYPE: PRT
<213> ORGANISM: Cuphea nucifera

<400> SEQUENCE: 6

```
Met Val Ala Ser Val Ala Ala Ser Ser Ser Phe Phe Pro Val Pro Ser
1               5                   10                  15

Ser Ser Ser Ser Ala Ser Ala Lys Ala Ser Arg Gly Ile Pro Asp Gly
            20                  25                  30

Leu Asp Val Arg Gly Ile Val Ala Lys Pro Ala Ser Ser Ser Gly Trp
        35                  40                  45

Met Gln Ala Lys Ala Ser Ala Arg Ala Ile Pro Lys Ile Asp Asp Thr
    50                  55                  60

Lys Val Gly Leu Arg Thr Asp Val Glu Glu Asp Ala Ala Ser Thr Ala
65                  70                  75                  80

Arg Arg Thr Ser Tyr Asn Gln Leu Pro Asp Trp Ser Met Leu Leu Ala
                85                  90                  95

Ala Ile Arg Thr Ile Phe Ser Ala Ala Glu Lys Gln Trp Thr Leu Leu
            100                 105                 110

Asp Ser Lys Lys Arg Gly Ala Asp Ala Val Ala Asp Ala Ser Gly Val
        115                 120                 125

Gly Lys Met Val Lys Asn Gly Leu Val Tyr Arg Gln Asn Phe Ser Ile
    130                 135                 140

Arg Ser Tyr Glu Ile Gly Val Asp Lys Arg Ala Ser Val Glu Ala Leu
145                 150                 155                 160

Met Asn His Phe Gln Glu Thr Ser Leu Asn His Cys Lys Cys Ile Gly
                165                 170                 175

Leu Met His Gly Gly Phe Gly Cys Thr Pro Glu Met Thr Arg Arg Asn
            180                 185                 190

Leu Ile Trp Val Val Ala Lys Met Leu Val His Val Glu Arg Tyr Pro
        195                 200                 205

Trp Trp Gly Asp Val Val Gln Ile Asn Thr Trp Ile Ser Ser Ser Gly
    210                 215                 220

Lys Asn Gly Met Gly Arg Asp Trp His Val His Asp Cys Gln Thr Gly
225                 230                 235                 240

Leu Pro Ile Met Arg Gly Thr Ser Val Trp Val Met Met Asp Lys His
                245                 250                 255

Thr Arg Arg Leu Ser Lys Leu Pro Glu Glu Val Arg Ala Glu Ile Thr
            260                 265                 270

Pro Phe Phe Ser Glu Arg Asp Ala Val Leu Asp Asp Asn Gly Arg Lys
        275                 280                 285

Leu Pro Lys Phe Asp Asp Ser Ala Ala His Val Arg Arg Gly Leu
    290                 295                 300

Thr Pro Arg Trp His Asp Phe Asp Val Asn Gln His Val Asn Asn Val
305                 310                 315                 320

Lys Tyr Val Gly Trp Ile Leu Glu Ser Val Pro Val Trp Met Leu Asp
                325                 330                 335

Gly Tyr Glu Val Ala Thr Met Ser Leu Glu Tyr Arg Arg Glu Cys Arg
            340                 345                 350

Met Asp Ser Val Val Gln Ser Leu Thr Ala Val Ser Ser Asp His Ala
        355                 360                 365

Asp Gly Ser Pro Ile Val Cys Gln His Leu Leu Arg Leu Glu Asp Gly
    370                 375                 380

Thr Glu Ile Val Arg Gly Gln Thr Glu Trp Arg Pro Lys Gln Gln Ala
385                 390                 395                 400
```

Arg Asp Leu Gly Asn Met Gly Leu His Pro Thr Glu Ser Lys
            405                 410

<210> SEQ ID NO 7
<211> LENGTH: 7
<212> TYPE: PRT
<213> ORGANISM: Artificial
<220> FEATURE:
<223> OTHER INFORMATION: Synthetic

<400> SEQUENCE: 7

Arg Tyr Pro Thr Trp Gly Asp
1               5

<210> SEQ ID NO 8
<211> LENGTH: 8
<212> TYPE: PRT
<213> ORGANISM: Artificial
<220> FEATURE:
<223> OTHER INFORMATION: Synthetic

<400> SEQUENCE: 8

Asn Gln His Val Asn Asn Val Lys
1               5

<210> SEQ ID NO 9
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n can be a, c, g, or t
<220> FEATURE:
<221> NAME/KEY: misc_feature
<222> LOCATION: (9)..(9)
<223> OTHER INFORMATION: n can be a, c, g, or t
<220> FEATURE:
<221> NAME/KEY: misc_feature
<222> LOCATION: (12)..(12)
<223> OTHER INFORMATION: n can be a, c, g, or t
<220> FEATURE:
<221> NAME/KEY: misc_feature
<222> LOCATION: (18)..(18)
<223> OTHER INFORMATION: n can be a, c, g, or t

<400> SEQUENCE: 9
agntayccna cntggggnga                                              20

<210> SEQ ID NO 10
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n can be a, c, g, or t
<220> FEATURE:
<221> NAME/KEY: misc_feature
<222> LOCATION: (15)..(15)
<223> OTHER INFORMATION: n can be a, c, g, or t

<400> SEQUENCE: 10
tacttnacrt trttnacrtg ytgrtt                                       26

```
<210> SEQ ID NO 11
<211> LENGTH: 25
<212> TYPE: DNA
<213> ORGANISM: Artificial
<220> FEATURE:
<223> OTHER INFORMATION: Synthetic

<400> SEQUENCE: 11
ctgcaaggcg attaagttgg gtaac                                        25

<210> SEQ ID NO 12
<211> LENGTH: 22
<212> TYPE: DNA
<213> ORGANISM: Artificial
<220> FEATURE:
<223> OTHER INFORMATION: Synthetic

<400> SEQUENCE: 12
cggctcgtat gttgtgtgga at                                           22

<210> SEQ ID NO 13
<211> LENGTH: 21
<212> TYPE: DNA
<213> ORGANISM: Artificial
<220> FEATURE:
<223> OTHER INFORMATION: Synthetic

<400> SEQUENCE: 13
gaaatcggcg cggatcgtac c                                            21

<210> SEQ ID NO 14
<211> LENGTH: 21
<212> TYPE: DNA
<213> ORGANISM: Artificial
<220> FEATURE:
<223> OTHER INFORMATION: Synthetic

<400> SEQUENCE: 14
gtcaatcgtt atccgacctg g                                            21

<210> SEQ ID NO 15
<211> LENGTH: 20
<212> TYPE: DNA
<213> ORGANISM: Artificial
<220> FEATURE:
<223> OTHER INFORMATION: Synthetic

<400> SEQUENCE: 15
atgatgaacc agaaaacccg                                              20

<210> SEQ ID NO 16
<211> LENGTH: 23
<212> TYPE: DNA
<213> ORGANISM: Artificial
<220> FEATURE:
<223> OTHER INFORMATION: Synthetic

<400> SEQUENCE: 16
ggtctgacgc cgcgttggaa cga                                          23

<210> SEQ ID NO 17
<211> LENGTH: 18
<212> TYPE: DNA
<213> ORGANISM: Artificial
<220> FEATURE:
<223> OTHER INFORMATION: Synthetic
```

```
<400> SEQUENCE: 17
ctgctgcgtc tggaagat                                                   18

<210> SEQ ID NO 18
<211> LENGTH: 21
<212> TYPE: DNA
<213> ORGANISM: Artificial
<220> FEATURE:
<223> OTHER INFORMATION: Synthetic

<400> SEQUENCE: 18
ggtacgatcc gcgccgattt c                                               21

<210> SEQ ID NO 19
<211> LENGTH: 21
<212> TYPE: DNA
<213> ORGANISM: Artificial
<220> FEATURE:
<223> OTHER INFORMATION: Synthetic

<400> SEQUENCE: 19
ccaggtcgga taacgattga c                                               21

<210> SEQ ID NO 20
<211> LENGTH: 20
<212> TYPE: DNA
<213> ORGANISM: Artificial
<220> FEATURE:
<223> OTHER INFORMATION: Synthetic

<400> SEQUENCE: 20
cgggttttct ggttcatcat                                                 20

<210> SEQ ID NO 21
<211> LENGTH: 23
<212> TYPE: DNA
<213> ORGANISM: Artificial
<220> FEATURE:
<223> OTHER INFORMATION: Synthetic

<400> SEQUENCE: 21
tcgttccaac gcggcgtcag acc                                             23

<210> SEQ ID NO 22
<211> LENGTH: 18
<212> TYPE: DNA
<213> ORGANISM: Artificial
<220> FEATURE:
<223> OTHER INFORMATION: Synthetic

<400> SEQUENCE: 22
atcttccaga cgcagcag                                                   18

<210> SEQ ID NO 23
<211> LENGTH: 717
<212> TYPE: DNA
<213> ORGANISM: Bryantella formatexigens

<400> SEQUENCE: 23
atgatttata tggcatatca ataccgcagc cgcatccgct acagcgaaat tggcgaggac      60
aaaaagctta cgctgcccgg tctggtgaat tatttccagg actgcagcac cttccagtcg     120
gaggcactcg gcatagggct ggacacgctg ggagcgcgcc agcgggcatg gcttctggcg     180
tcctggaaaa ttgtaataga caggctgccg cggcttgggg aggaggttgt gacggagacc     240
```

```
tggccatatg gctttaaggg cttccaggga aaccgcaact tccgtatgct ggaccaggag    300
ggacatacac tggctgcagc ggcatccgtc tggatttatt taaatgtgga aagcgggcat    360
ccgtgccgga ttgacgggga tgttctggag gcatatgagc tggaagagga gctgccgctc    420
ggtccgtttt cgcgcaagat tccggttccg gaggaaagca cggagcggga cagctttctg    480
gtgatgcgca gtcacctgga caccaatcac catgtcaaca acgggcagta tatactgatg    540
gcggaggaat atctgccgga gggctttaaa gtaaagcaga tacgcgtgga gtaccgcaaa    600
gccgccgttc tgcacgatac gattgtgccg tttgtgtgca cagagccgca gcgctgcacg    660
gtcagccttt gcggaagtga tgaaaagccg tttgccgtcg tagaattttc ggaataa      717
```

<210> SEQ ID NO 24
<211> LENGTH: 238
<212> TYPE: PRT
<213> ORGANISM: Bryantella formatexigens

<400> SEQUENCE: 24

```
Met Ile Tyr Met Ala Tyr Gln Tyr Arg Ser Arg Ile Arg Tyr Ser Glu
1               5                   10                  15

Ile Gly Glu Asp Lys Lys Leu Thr Leu Pro Gly Leu Val Asn Tyr Phe
            20                  25                  30

Gln Asp Cys Ser Thr Phe Gln Ser Glu Ala Leu Gly Ile Gly Leu Asp
        35                  40                  45

Thr Leu Gly Ala Arg Gln Arg Ala Trp Leu Leu Ala Ser Trp Lys Ile
    50                  55                  60

Val Ile Asp Arg Leu Pro Arg Leu Gly Glu Glu Val Val Thr Glu Thr
65                  70                  75                  80

Trp Pro Tyr Gly Phe Lys Gly Phe Gln Gly Asn Arg Asn Phe Arg Met
                85                  90                  95

Leu Asp Gln Glu Gly His Thr Leu Ala Ala Ala Ser Val Trp Ile
            100                 105                 110

Tyr Leu Asn Val Glu Ser Gly His Pro Cys Arg Ile Asp Gly Asp Val
        115                 120                 125

Leu Glu Ala Tyr Glu Leu Glu Glu Leu Pro Leu Gly Pro Phe Ser
    130                 135                 140

Arg Lys Ile Pro Val Pro Glu Glu Ser Thr Glu Arg Asp Ser Phe Leu
145                 150                 155                 160

Val Met Arg Ser His Leu Asp Thr Asn His His Val Asn Asn Gly Gln
                165                 170                 175

Tyr Ile Leu Met Ala Glu Glu Tyr Leu Pro Glu Gly Phe Lys Val Lys
            180                 185                 190

Gln Ile Arg Val Glu Tyr Arg Lys Ala Ala Val Leu His Asp Thr Ile
        195                 200                 205

Val Pro Phe Val Cys Thr Glu Pro Gln Arg Cys Thr Val Ser Leu Cys
    210                 215                 220

Gly Ser Asp Glu Lys Pro Phe Ala Val Val Glu Phe Ser Glu
225                 230                 235
```